(12) United States Patent
Disney et al.

(10) Patent No.: US 10,220,031 B2
(45) Date of Patent: Mar. 5, 2019

(54) TOXIC RNA INHIBITORS SELF-ASSEMBLED IN SITU

(71) Applicants: Matthew D. Disney, Jupiter, FL (US); Suzanne G. Rzuczek, Jupiter, FL (US)

(72) Inventors: Matthew D. Disney, Jupiter, FL (US); Suzanne G. Rzuczek, Jupiter, FL (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 15/327,117

(22) PCT Filed: Jul. 17, 2015

(86) PCT No.: PCT/US2015/040902
§ 371 (c)(1),
(2) Date: Jan. 18, 2017

(87) PCT Pub. No.: WO2016/011348
PCT Pub. Date: Jan. 21, 2016

(65) Prior Publication Data
US 2017/0143703 A1   May 25, 2017

Related U.S. Application Data

(60) Provisional application No. 62/026,266, filed on Jul. 18, 2014.

(51) Int. Cl.
| | |
|---|---|
| *A61K 31/496* | (2006.01) |
| *A61K 31/702* | (2006.01) |
| *A61K 38/07* | (2006.01) |
| *A61K 38/08* | (2019.01) |
| *A61K 47/54* | (2017.01) |
| *A61K 47/55* | (2017.01) |

(52) U.S. Cl.
CPC .......... *A61K 31/496* (2013.01); *A61K 31/702* (2013.01); *A61K 38/07* (2013.01); *A61K 38/08* (2013.01); *A61K 47/549* (2017.08); *A61K 47/55* (2017.08); *A61K 47/557* (2017.08)

(58) Field of Classification Search
None
See application file for complete search history.

(56) References Cited

U.S. PATENT DOCUMENTS 9,150,612 B2 * 10/2015 Disney ................ C07K 14/001

* cited by examiner

*Primary Examiner* — James S Ketter
(74) *Attorney, Agent, or Firm* — Geoffrey K. Cooper; Thomas Fitting

(57) ABSTRACT

Potent modulators of RNA function can be assembled in cellulo by using the cell as a reaction vessel and a disease-causing RNA as a catalyst. When designing small molecule effectors of function, a balance between permeability and potency must be struck. Low molecular weight compounds are more permeable while higher molecular weight compounds are more potent. The advantages of both types of compounds could be synergized if low molecular weight molecules could be transformed into potent, multivalent ligands via a reaction catalyzed by binding to a target in cells expressing a genetic defect. We demonstrate that this approach is indeed viable in cellulo. Small molecule modules with precisely positioned alkyne and azide moieties bind adjacent internal loops in $r(CCUG)^{exp}$, the causative agent of myotonic dystrophy type 2 (DM2), and are transformed into oligomeric, potent inhibitors of DM2 RNA dysfunction via a 1,3 Huisgen dipolar cycloaddition reaction, a variant of click chemistry. Additionally, we show that this approach is applicable to the r(CUG) repeating RNA that causes myotonic dystrophy type 1 (DM1). The click chemistry approach also allows for FRET sensors to be synthesized on-site by using r(CUG) repeats as a catalyst. Furthermore it is shown that small molecule binding sites in patient-derived cells can be identified by using reactive approaches termed Chem-CLIP and Chem-CLIP-Map. Lastly, it is shown that small molecules that target r(CUG) expansions can be designed to cleave this RNA by appending a small molecule with a nucleic acid cleaving module.

6 Claims, 42 Drawing Sheets

Specification includes a Sequence Listing.

SEQUENCE LISTING

<160> NUMBER OF SEQ ID NOS: 18

<210> SEQ ID NO 1
<211> LENGTH: 20
<212> TYPE: DNA
<213> ORGANISM: Artificial sequence
<220> FEATURE:
<223> OTHER INFORMATION: Synthetic sequence

<400> SEQUENCE: 1
cattcaccac attggtgtgc                                              20

<210> SEQ ID NO 2
<211> LENGTH: 22
<212> TYPE: DNA
<213> ORGANISM: Artificial sequence
<220> FEATURE:
<223> OTHER INFORMATION: Synthetic sequence

<400> SEQUENCE: 2
aagtgatcct agactagccg cc                                           22

<210> SEQ ID NO 3

<211> LENGTH: 20
<212> TYPE: DNA
<213> ORGANISM: Artificial sequence
<220> FEATURE:
<223> OTHER INFORMATION: Synthetic sequence

<400> SEQUENCE: 3
gtgagtttgg ggacccttga                                      20

<210> SEQ ID NO 4
<211> LENGTH: 20
<212> TYPE: DNA
<213> ORGANISM: Artificial sequence
<220> FEATURE:
<223> OTHER INFORMATION: Synthetic sequence

<400> SEQUENCE: 4
caccctgaaa actttgcccc                                      20

<210> SEQ ID NO 5
<211> LENGTH: 20
<212> TYPE: DNA
<213> ORGANISM: Artificial sequence
<220> FEATURE:
<223> OTHER INFORMATION: Synthetic sequence

<400> SEQUENCE: 5
gtaacccgtt gaaccccatt                                      20

<210> SEQ ID NO 6
<211> LENGTH: 20
<212> TYPE: DNA
<213> ORGANISM: Artificial sequence
<220> FEATURE:
<223> OTHER INFORMATION: Synthetic sequence

<400> SEQUENCE: 6
ccatccaatc ggtagtagcg                                      20

<210> SEQ ID NO 7
<211> LENGTH: 21
<212> TYPE: DNA
<213> ORGANISM: Artificial sequence
<220> FEATURE:
<223> OTHER INFORMATION: Synthetic sequence

<400> SEQUENCE: 7
gctgcccaat accaggtcaa c                                    21

<210> SEQ ID NO 8
<211> LENGTH: 21
<212> TYPE: DNA
<213> ORGANISM: Artificial sequence
<220> FEATURE:
<223> OTHER INFORMATION: Synthetic sequence

<400> SEQUENCE: 8
tggtgggaga aatgctgtat g                                    21

<210> SEQ ID NO 9
<211> LENGTH: 48
<212> TYPE: RNA
<213> ORGANISM: Artificial Sequence
<220> FEATURE:
<223> OTHER INFORMATION: Synthetic sequence

<400> SEQUENCE: 9

-continued ccugccugcc ugccugccug ccugccugcc ugccugccug ccugccug        48

<210> SEQ ID NO 10
<211> LENGTH: 54
<212> TYPE: RNA
<213> ORGANISM: Artificial Sequence
<220> FEATURE:
<223> OTHER INFORMATION: Synthetic Sequence

<400> SEQUENCE: 10
gcgccugccu gccugccugc cugccugccu gccugccugc ugccugccu gcgc        54

<210> SEQ ID NO 11
<211> LENGTH: 42
<212> TYPE: RNA
<213> ORGANISM: Artificial Sequence
<220> FEATURE:
<223> OTHER INFORMATION: Synthetic Sequence

<400> SEQUENCE: 11
gcgcugcugc ugcugcugcu gcugcugcug cugcugcugc gc        42

<210> SEQ ID NO 12
<211> LENGTH: 60
<212> TYPE: RNA
<213> ORGANISM: Artificial Sequence
<220> FEATURE:
<223> OTHER INFORMATION: Synthetic Sequence

<400> SEQUENCE: 12
auucuauucu auucuauucu auucuauucu auucuauucu auucuauucu auucuauucu        60

<210> SEQ ID NO 13
<211> LENGTH: 42
<212> TYPE: RNA
<213> ORGANISM: Artificial Sequence
<220> FEATURE:
<223> OTHER INFORMATION: Synthetic Sequence

<400> SEQUENCE: 13
gcgcggcggc ggcggcggcg gcggcggcgg cggcggcggc gc        42

<210> SEQ ID NO 14
<211> LENGTH: 42
<212> TYPE: RNA
<213> ORGANISM: Artificial Sequence
<220> FEATURE:
<223> OTHER INFORMATION: Synthetic Sequence

<400> SEQUENCE: 14
gcgcagcagc agcagcagca gcagcagcag cagcagcagc gc        42

<210> SEQ ID NO 15
<211> LENGTH: 40
<212> TYPE: RNA
<213> ORGANISM: Artificial Sequence
<220> FEATURE:
<223> OTHER INFORMATION: Synthetic Sequence

<400> SEQUENCE: 15
gggagagggu uuaauuacga aaguaauugg auccgcaagg        40

<210> SEQ ID NO 16
<211> LENGTH: 42
<212> TYPE: RNA

```
<213> ORGANISM: Artificial Sequence
<220> FEATURE:
<223> OTHER INFORMATION: Synthetic Sequence

<400> SEQUENCE: 16
cugcugcugc ugcugcugcu gcugcugcug cugcugcugc ug                    42

<210> SEQ ID NO 17
<211> LENGTH: 36
<212> TYPE: RNA
<213> ORGANISM: Artificial Sequence
<220> FEATURE:
<223> OTHER INFORMATION: Synthetic Sequence

<400> SEQUENCE: 17
cugcugcugc ugcugcugcu gcugcugcug cugcug                           36

<210> SEQ ID NO 18
<211> LENGTH: 54
<212> TYPE: RNA
<213> ORGANISM: Artificial Sequence
<220> FEATURE:
<223> OTHER INFORMATION: Synthetic Sequence

<400> SEQUENCE: 18
cugcugcugc ugcugcugcu gcugcugcug cugcugcugc ugcugcugcu gcug       54
```

TOXIC RNA INHIBITORS SELF-ASSEMBLED IN SITU

CROSS-REFERENCE TO RELATED APPLICATION

This application claims the priority of U.S. provisional application Ser. No. 62/026,266, filed Jul. 18, 2014, the disclosure of which is incorporated by reference herein in its entirety.

BACKGROUND

RNA dysfunction causes disease through various mechanisms, including microRNA silencing of pro-apoptotic proteins,[1] translation of aberrant protein,[2] and gain-of-function.[3] It has been difficult, however, to design small molecule chemical probes of RNA function or lead therapeutics. If broadly applicable methods were developed to drug non-ribosomal RNAs with small molecules, it could have important applications in chemical biology and medicinal chemistry.[4] One class of RNA-mediated diseases is caused by expanded repeating RNAs, or microsatellite disorders. There are >20 known microsatellite disorders, including myotonic dystrophy (DM) and amyotrophic lateral sclerosis (Lou Gehrig's Disease; ALS).[5] The cellular consequences of repeats are varied and can include alterations at the protein, RNA, and DNA levels. Myotonic dystrophy type 2 (DM2) is caused by a toxic gain-of-function by a r(CCUG) repeat expansion (r(CCUG)$^{exp}$. Myotonic dystrophy type 1 (DM1) is caused by a toxic gain-of-function by a r(CUG) repeat expansion (r(CUG)$^{exp}$).

SUMMARY

We have designed inhibitors or modulators of the RNA that causes myotonic dystrophy type 2 (DM2) based on RNA motif-small molecule interactions.[6] DM2 is caused by a toxic gain-of-function by a r(CCUG) repeat expansion (r(CCUG)$^{exp}$) located in intron 1 of the zinc finger protein 9 (ZNF9) pre-mRNA.[7] The RNA folds into a hairpin structure that contains repeating units of 5'CCUG/3'GUCC (2×2 nucleotide internal loops) in the stem. The loops form high affinity binding sites for muscleblind-like 1 protein (MBNL1), a regulator of alternative pre-mRNA splicing, which is inactivated upon binding (FIG. 1A). Our designed inhibitors of r(CCUG)$^{exp}$ are based on a kanamycin A derivative, which is acylated at the 6' position, that binds 5'C CUG/3'GUCC with high affinity. Notably, acylation of the 6' amine ablates binding to rRNA.[8] Indeed, the kanamycin derivative and modularly assembled (or multivalent) compounds thereof improve DM2-associated defects in a cellular model.[6a] As observed for other repeat expansions, modularly assembled compounds are more potent inhibitors of cellular dysfunction, presumably due to their high affinities, selectivities, and the larger surface areas they sequester on the target.[6a] Even though multivalent compounds are more potent and selective in vitro, in some cases in cellulo potency decreases as a function of valency because they are less cell permeable.[9] Thus, a careful balance must be struck between ligand size, potency, and permeability.

We have also used a similar approach to design inhibitors or modulators of the RNA that causes myotonic dystrophy type 1 (DM1). In this case, DM1 is caused by a toxic gain-of-function by a r(CUG) repeat expansion (r(CUG)$^{exp}$) that is located in the 3' untranslated region (UTR) of the dystophia myotonica protein kinase (DMPK) mRNA.[7]

Other aspects of this invention for DM1 include: (i) design of optimized dimeric compounds that target r(CUG)$^{exp}$; (ii) covalent small molecules that target r(CUG)$^{exp}$ and allow for target validation (RNAs bound) and the sites in the RNAs that bind the small molecules; (iii) use of in cellulo click chemistry to synthesize inhibitors on-site that are highly potent and selective; (iv) fluorescence resonance energy transfer (FRET) approaches to use r(CUG)$^{exp}$ as a catalyst to synthesize FRET sensors; and (v) design of small molecules targeting r(CUG)$^{exp}$ that cleave r(CUG)$^{exp}$ in patient-derived cells.

The invention provides, in various embodiments, a method of forming, within a living cell, a modulator of RNA function, comprising exposing the cell to one or two small molecule modules to which the cell is permeable, a single module bearing both alkyne and azide groups, or the two modules comprising respectively alkyne and azide moieties that bind adjacent internal loops in r(CCUG)$^{exp}$ or r(CUG)$^{exp}$, the causative agent of myotonic dystrophy type 2 (DM2) and type 1 (DM1) (Day, J. W., and Ranum, L. P. (2005) RNA pathogenesis of the myotonic dystrophies, Neuromuscul. Disord. 15, 5-16; Miller, J. W., Urbinati, C. R., Teng-Umnuay, P., Stenberg, M. G., Byrne, B. J., Thornton, C. A., and Swanson, M. S. (2000) Recruitment of human muscleblind proteins to (CUG)(n) expansions associated with myotonic dystrophy, EMBO J. 19, 4439-4448; Mankodi, A., Takahashi, M. P., Jiang, H., Beck, C. L., Bowers, W. J., Moxley, R. T., Cannon, S. C., and Thornton, C. A. (2002) Expanded CUG repeats trigger aberrant splicing of Clcn-1 chloride channel pre-mRNA and hyperexcitability of skeletal muscle in myotonic dystrophy, Mol. Cell 10, 35-44), respectively, such that the one module, or the two modules are transformed by condensation of the alkyne and azide group in a 1,3 Huisgen dipolar cycloaddition reaction into oligomeric, potent inhibitors of DM1 or DM2 RNA dysfunction via a 1,3 Huisgen dipolar cycloaddition reaction. Thus, the monomeric precursors of the oligomeric modulator can either be single compounds that display azide and alkyne units on the same molecule can bind to adjacent sites and undergo a 1,3 Huisgen dipolar cycloaddition reaction, or a pair of molecular structures, one of which bears an alkyne group and the other of which bears an azide group.

The invention also provides, in various embodiments, a method of forming, within a living cell, a modulator of RNA function, comprising exposing the cell to small molecule modules to which the cell is permeable in which the module contains both alkyne and azide moieties. The invention further provides, in various embodiments, modulators of RNA function, formed by exposing a cell containing RNA expanded repeat sequences r(CCUG)$^{exp}$ or r(CUG)$^{exp}$, the causative agent of myotonic dystrophy type 2 (DM2) and type 1 (DM1) respectively, to one or more RNA extended repeat binding modules to which the cell is permeable, the two modules comprising respectively alkyne and azide moieties that can condense via a Huisgen 1,3-dipolar cycloaddition reaction to form an oligomeric modulator that interferes with the function of the toxic RNAs. For the r(CCUG)$^{exp}$ modulator for treatment of DM2, the cell-permeable modules can comprise kanamycin analogs. For the r(CUG)$^{exp}$ modulator for treatment of DM1, the cell-permeable modules can comprise bis-benzimidazoles or other heteroaryl compounds.

indicates p<0.01; "***" indicates p<0.001 as determined by a two-tailed Student t-test (n≥3).

Figure 15:
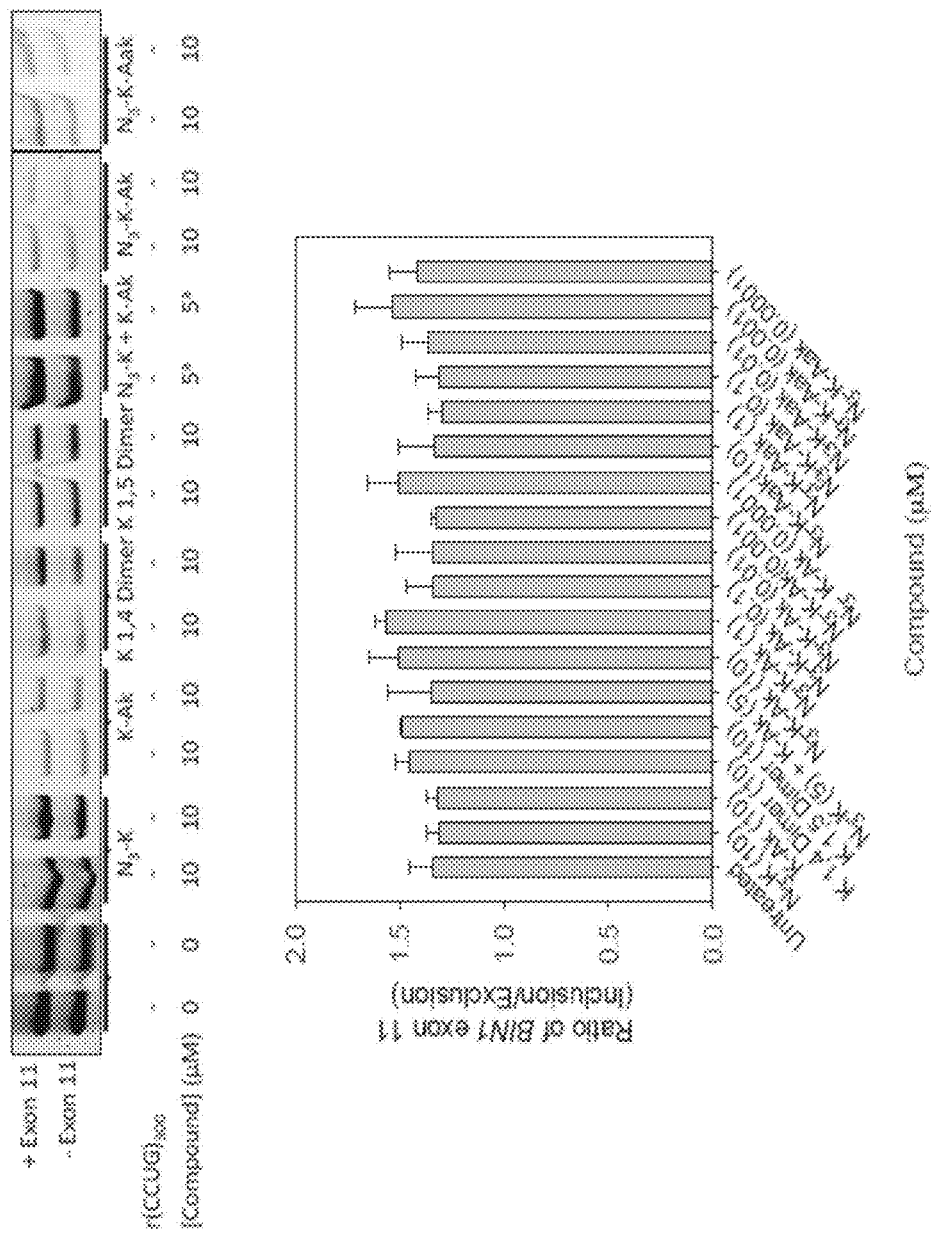

FIG. 15. Top, Representative gel images showing that K derivatives do not affect BIN1 splicing patterns in cells that do not express $r(CCUG)_{300}$. Bottom, Quantification of BIN1 splicing patterns in cells that do not express $r(CCUG)_{300}$. None of the compounds evaluated had a statistically significant effect on BIN1 pre-mRNA splicing patterns in the absence of $r(CCUG)_{300}$ as determined by a two-tailed Student t-test (n≥3). The concentration of compound tested is provided in parentheses (mM).

Figure 16:
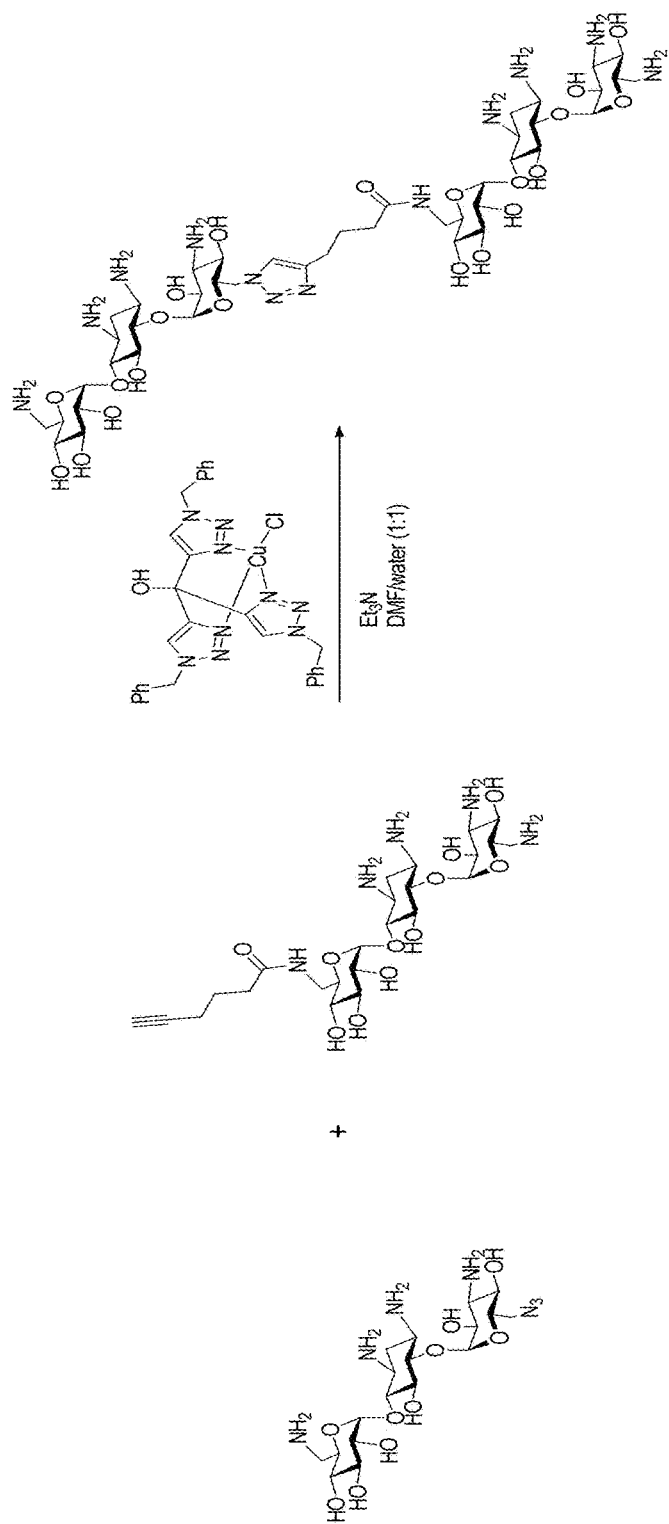

FIG. 16 shows the scheme for synthesis of the K 1,4 Dimer.

Figure 17:
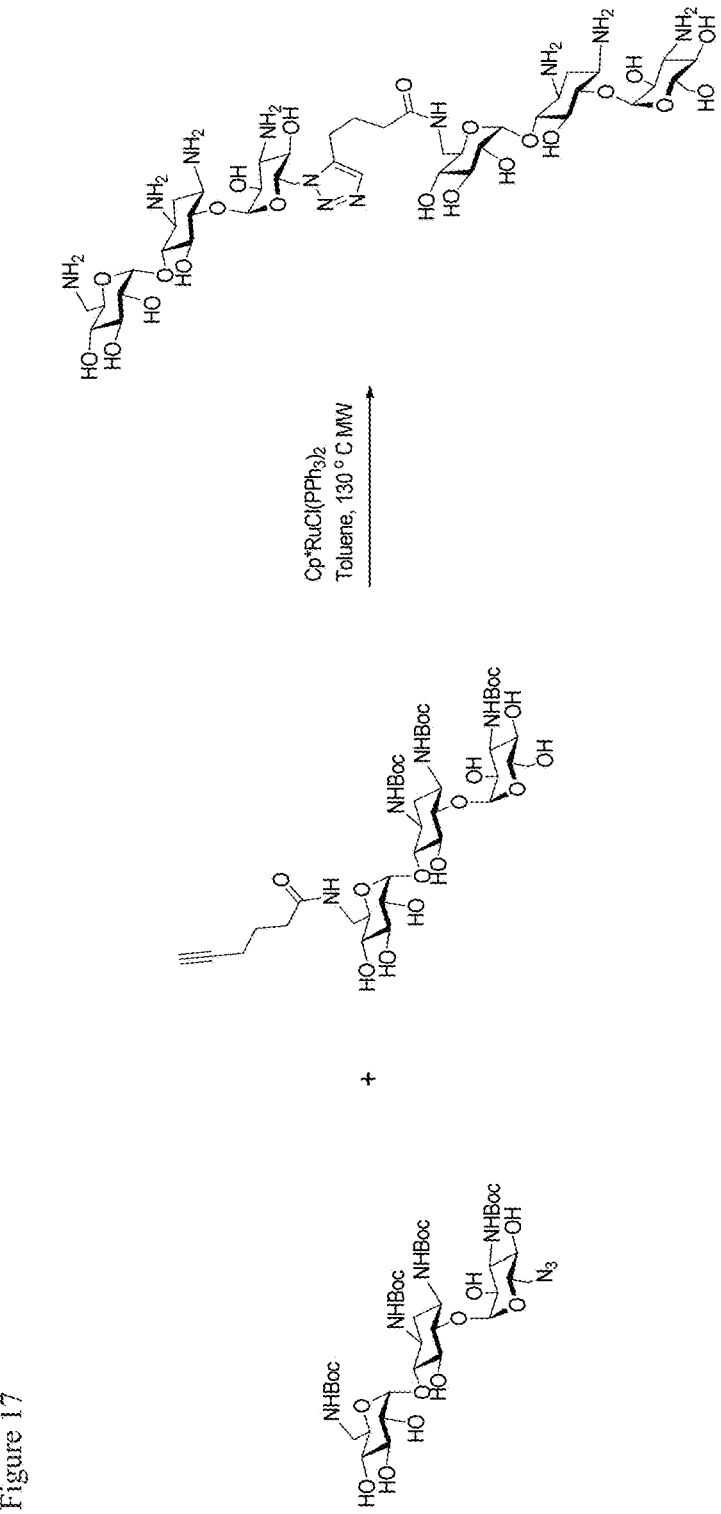

FIG. 17 shows the scheme for synthesis of the K 1,5 Dimer.

Figure 18:
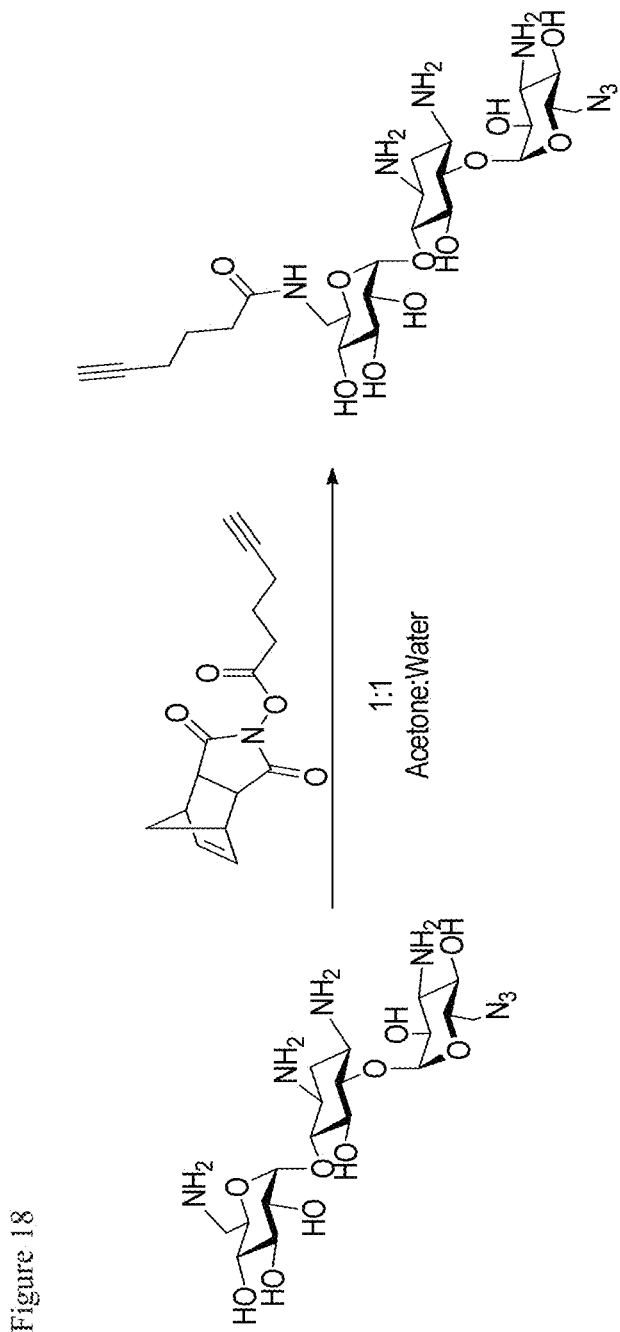

FIG. 18 shows the scheme for synthesis of $N_3$-K-Ak.

Figure 19:
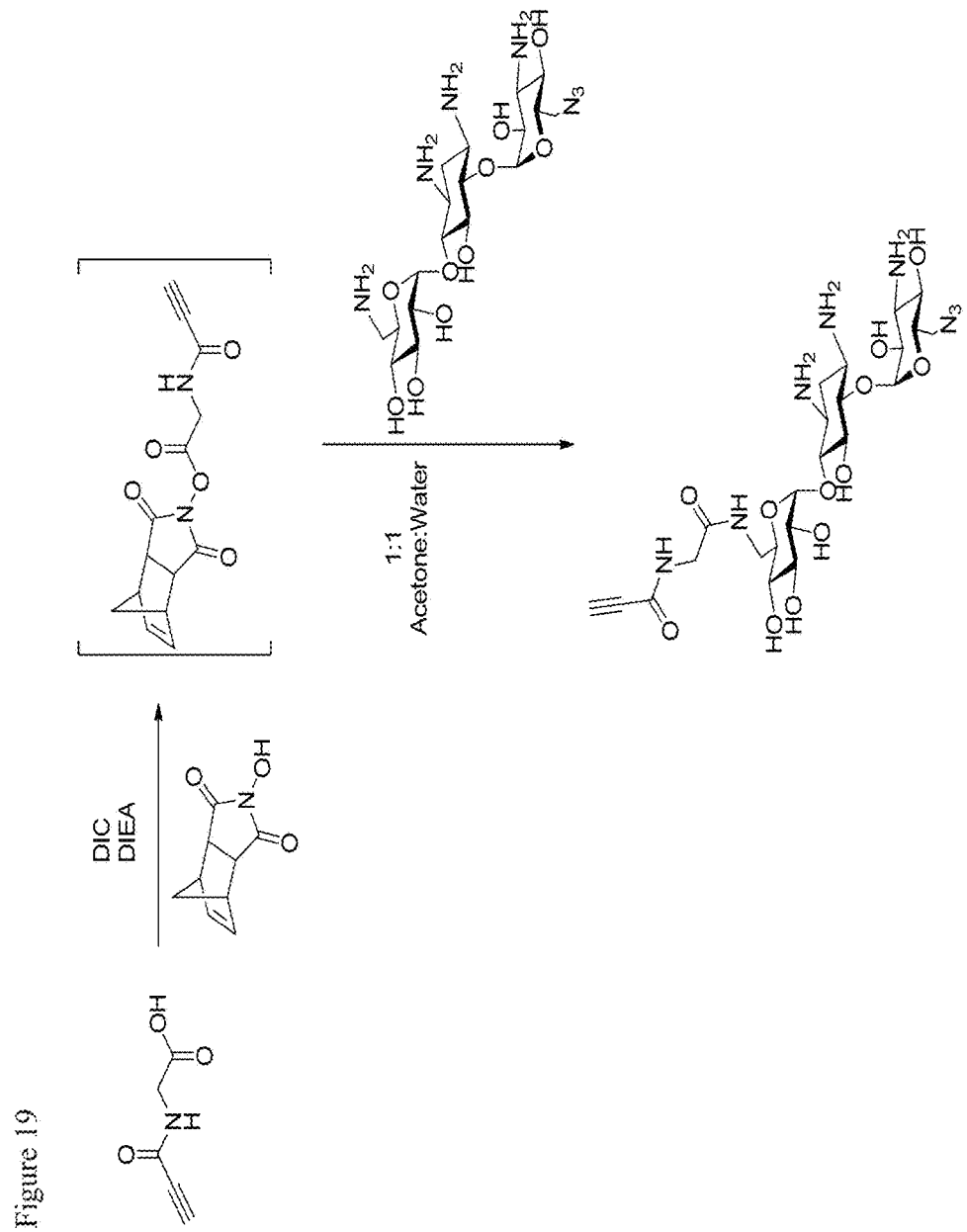

FIG. 19 shows the scheme for synthesis of $N_3$-K-Aak.

Figure 20:
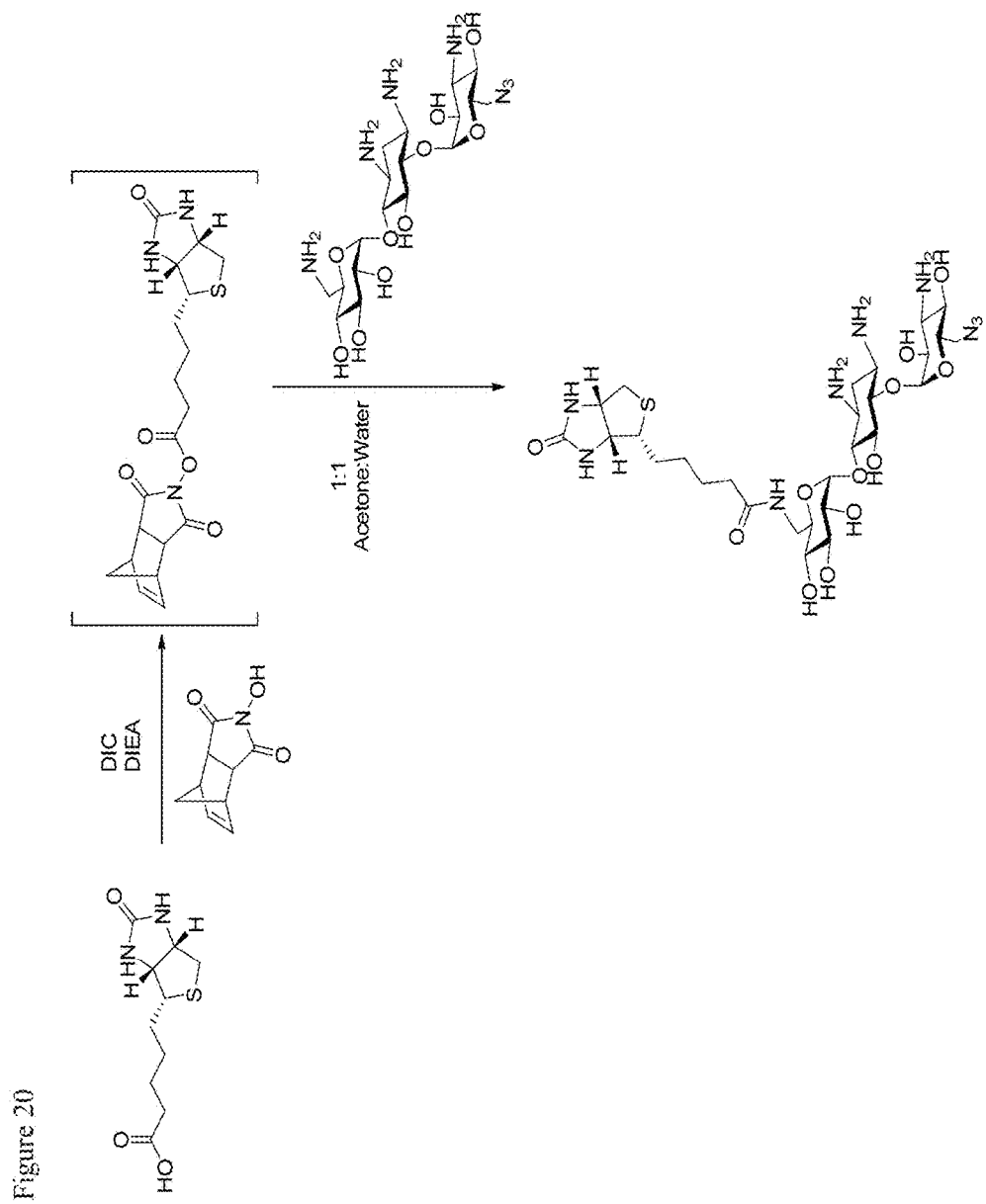

FIG. 20 shows the scheme for synthesis of $N_3$-K-Biotin.

Figure 21:
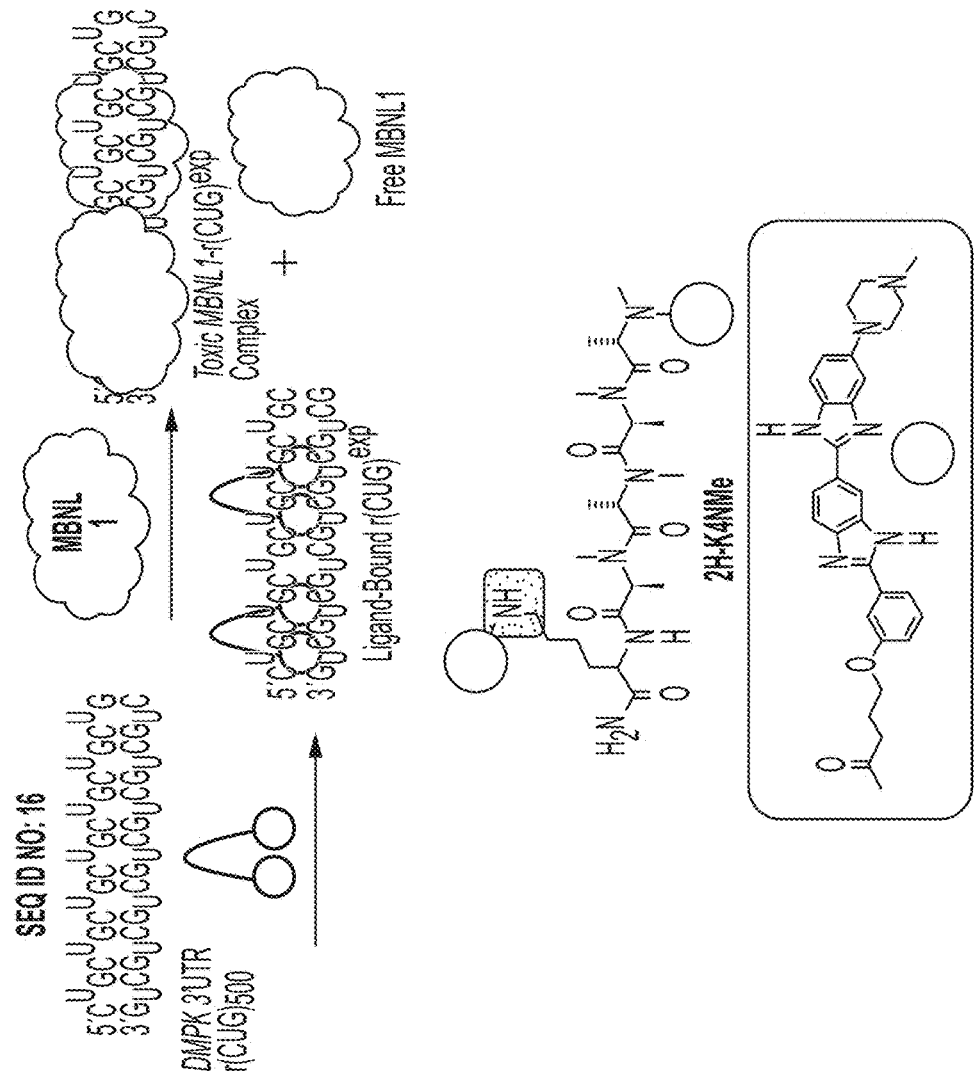

FIG. 21. The toxic RNA-protein complex causative of DM1 and designer small molecules that are used to ameliorate and study disease-associated cellular dysfunction and in cellulo target selectivity.

Figure 22:
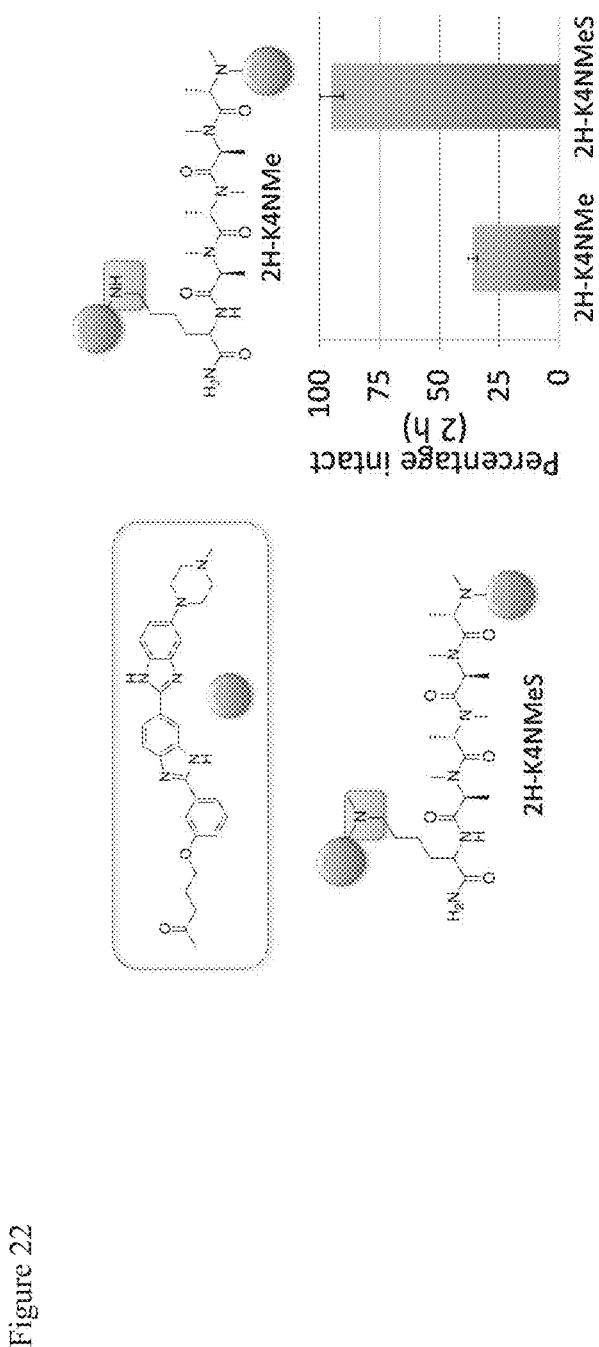

FIG. 22. Lead optimization of compounds for metabolic stability. Compound 2H-K4NMe is unstable in microsomes (bottom right plot) and instability was traced to the imino proton, which was removed by N-methylation to provide 2H-K4NMeS, which is stable in microsomes.

Figure 23:
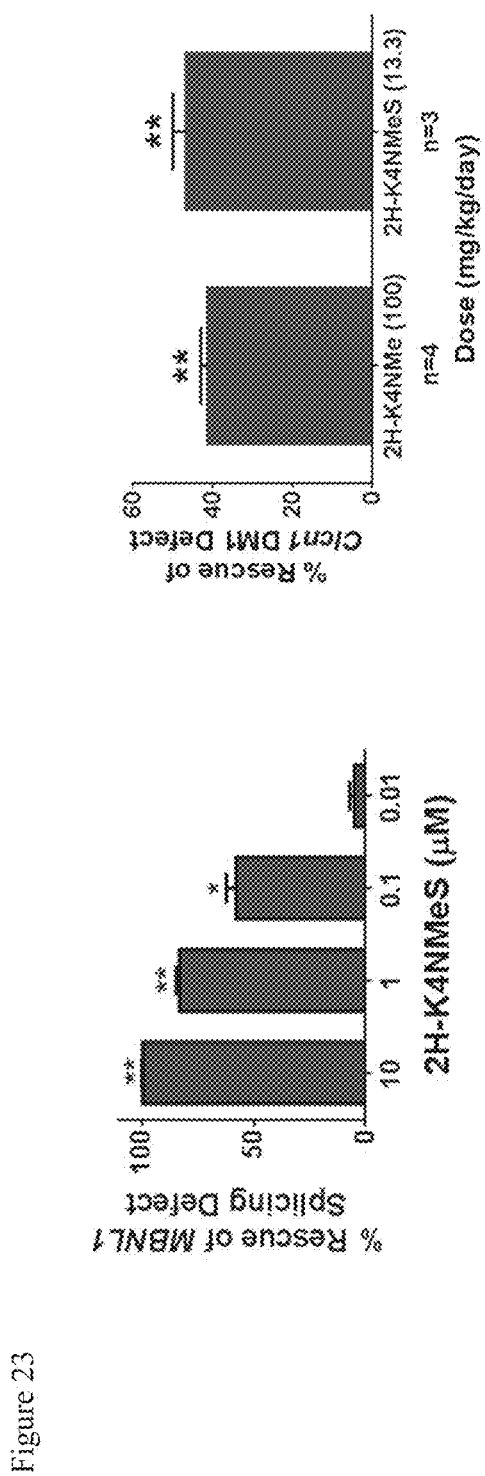

FIG. 23. Designer small molecule 2H-K4NMeS improves DM1-associated pre-mRNA splicing defects in patient-derived cell lines (left) and in a DM1 mouse model (right). Mankodi, A., Logigian, E., Callahan, L., McClain, C., White, R., Henderson, D., Krym, M., and Thornton, C. A. (2000) Myotonic dystrophy in transgenic mice expressing an expanded CUG repeat. Science 289, 1769-1773.

Figure 24:
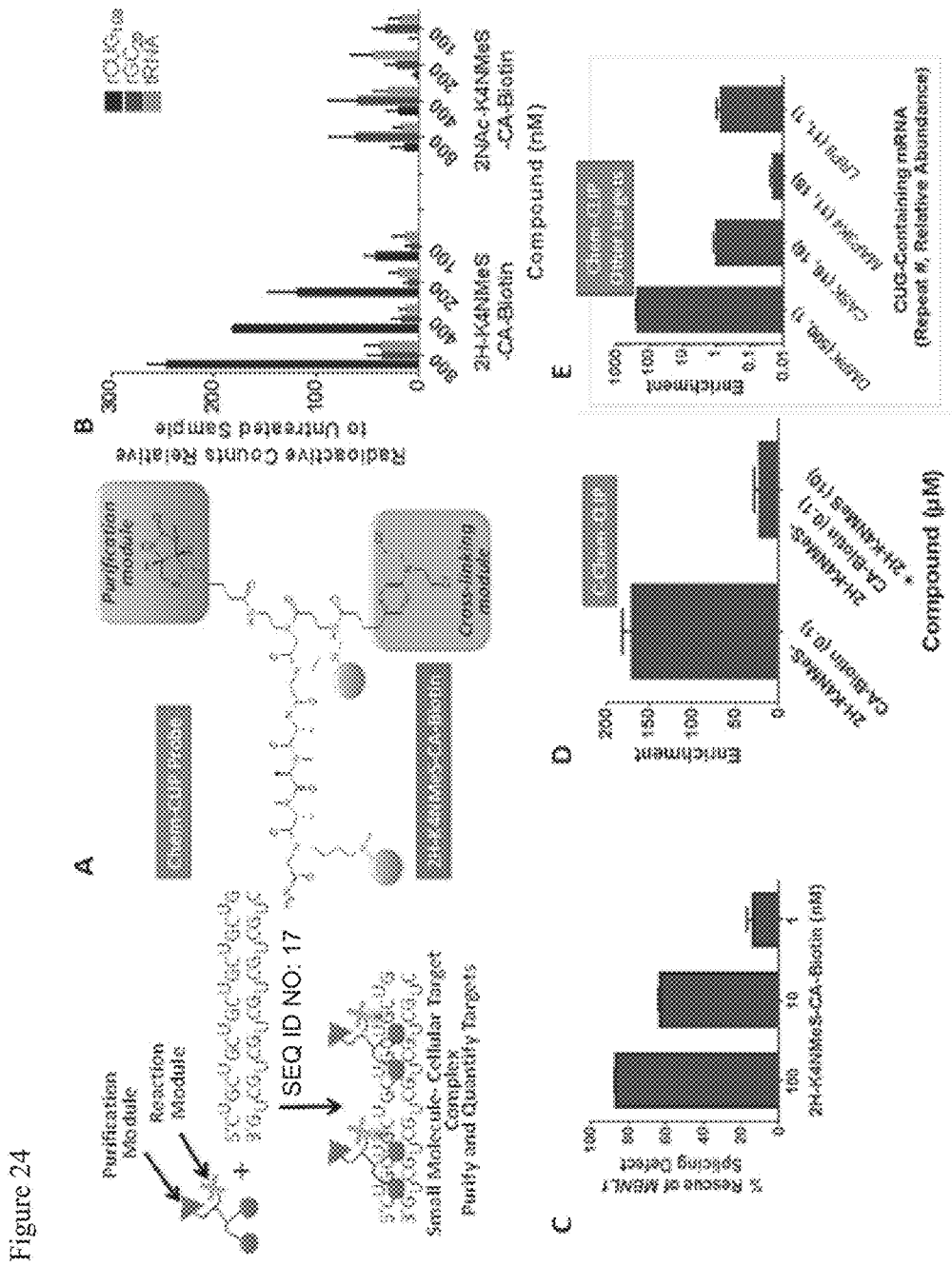

FIG. 24. The designer small molecule 2H-K4NMeS is appended with a reactive module (CA) and a purification tag (biotin) to produce 2H-K4NMeS-CA-Biotin. This compound forms a cross-link (covalent bond) with bound RNAs in cells and allows them to be purified and quantified to validate the targets of the small molecules by using an approach termed Chemical Cross-Linking and Isolation by Pull Down (Chem-CLIP) A, The structure of the probe compound. B, In vitro data showing that the probe selectively reacts with $r(CUG)^{exp}$. C, 2H-K4NMeS-CA-Biotin improves DM1-associated pre-mRNA splicing defects in cells. D, The non-covalent compound 2H-K4NMeS can compete 2H-K4NMeS-CA-Biotin from reaction with the $r(CUG)^{exp}$ target as determined by Competitive Chem-CLIP (C-Chem-CLIP). E, Pull-down of the RNA targets by 2H-K4NMeS-CA-Biotin shows the compound binds to disease-causing expanded transcripts and not other RNAs with shorter (non-pathogenic length) r(CUG) repeats.

Figure 25:
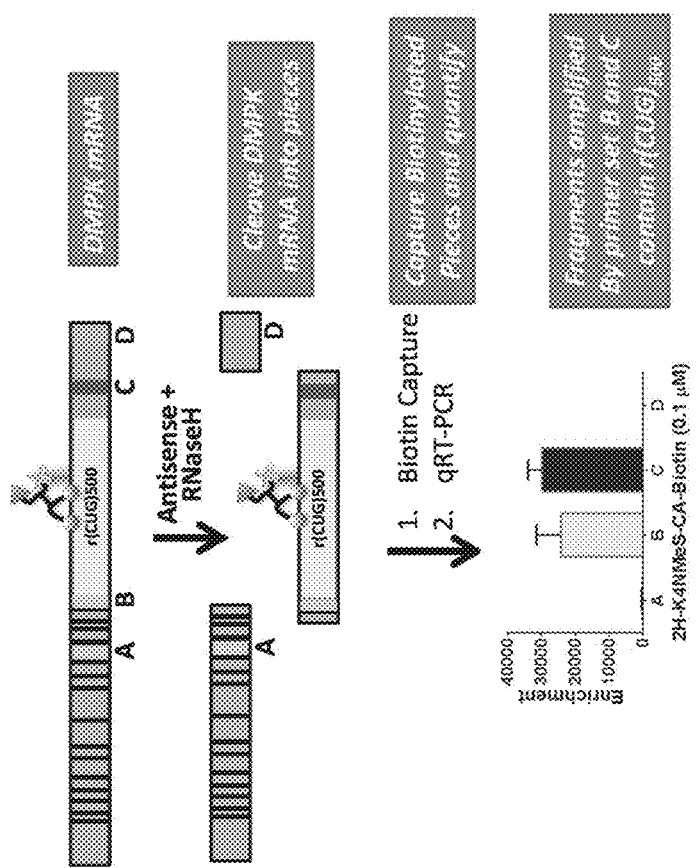

FIG. 25. Chemical Cross-Linking and Isolation by Pull Down and Ligand Binding-Site Mapping (Chem-CLIP-Map). The DMPK mRNA that reacted with 2H-K4NMeS-CA-Biotin was site specifically digested with RNase H by using oligonucleotides complementary to different regions in the mRNA. After digestion, regions of the RNA that reacted with 2H-K4NMeS-CA-Biotin were captured on a streptavidin resin and quantified by using qRT-PCR. Data shows that 2H-K4NMeS-CA-Biotin binds to $r(CUG)^{exp}$ in DMPK mRNA.

Figure 26:
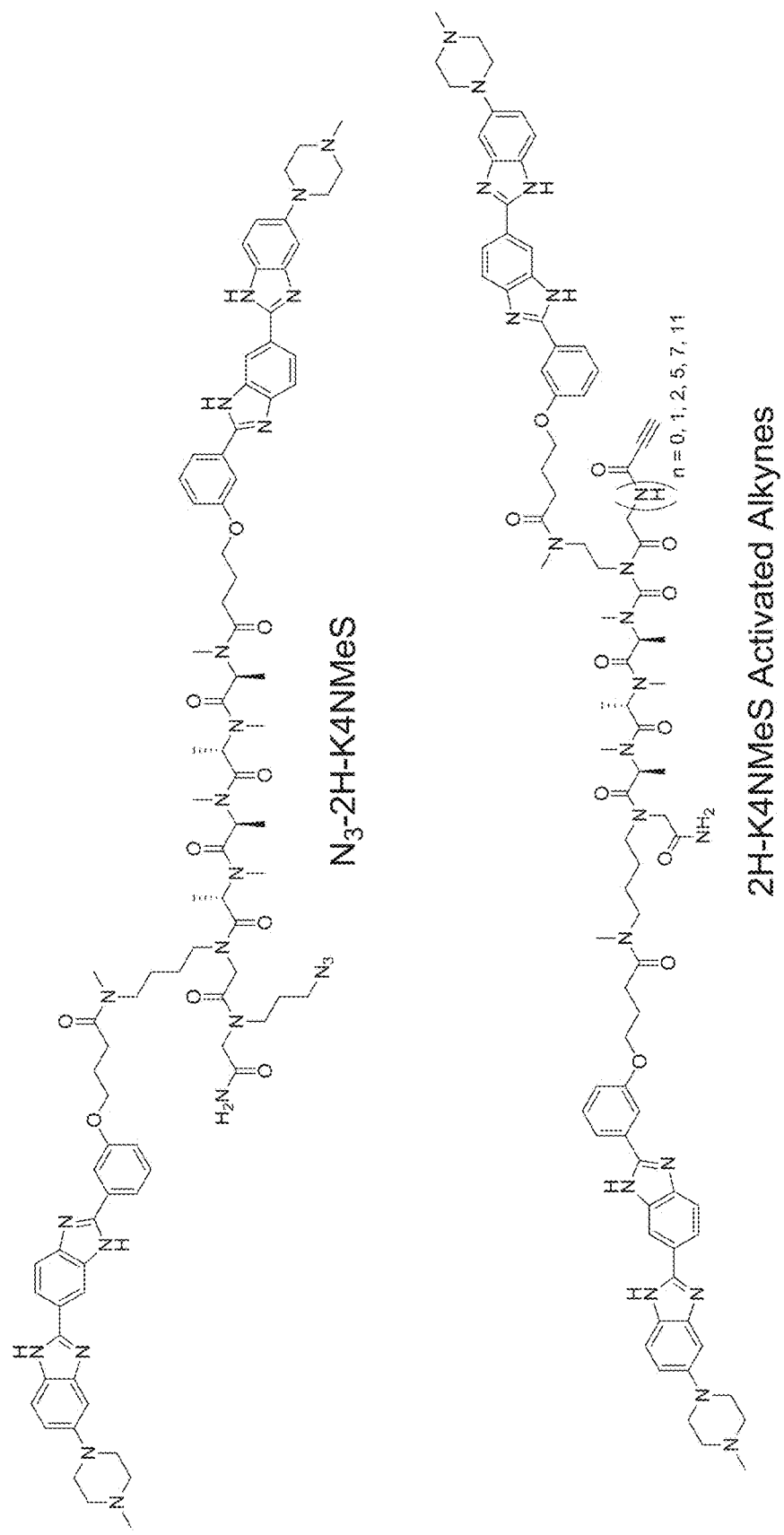

FIG. 26. The structures of the compounds that were tested for validating the on-site drug synthesis in vitro.

Figure 27:
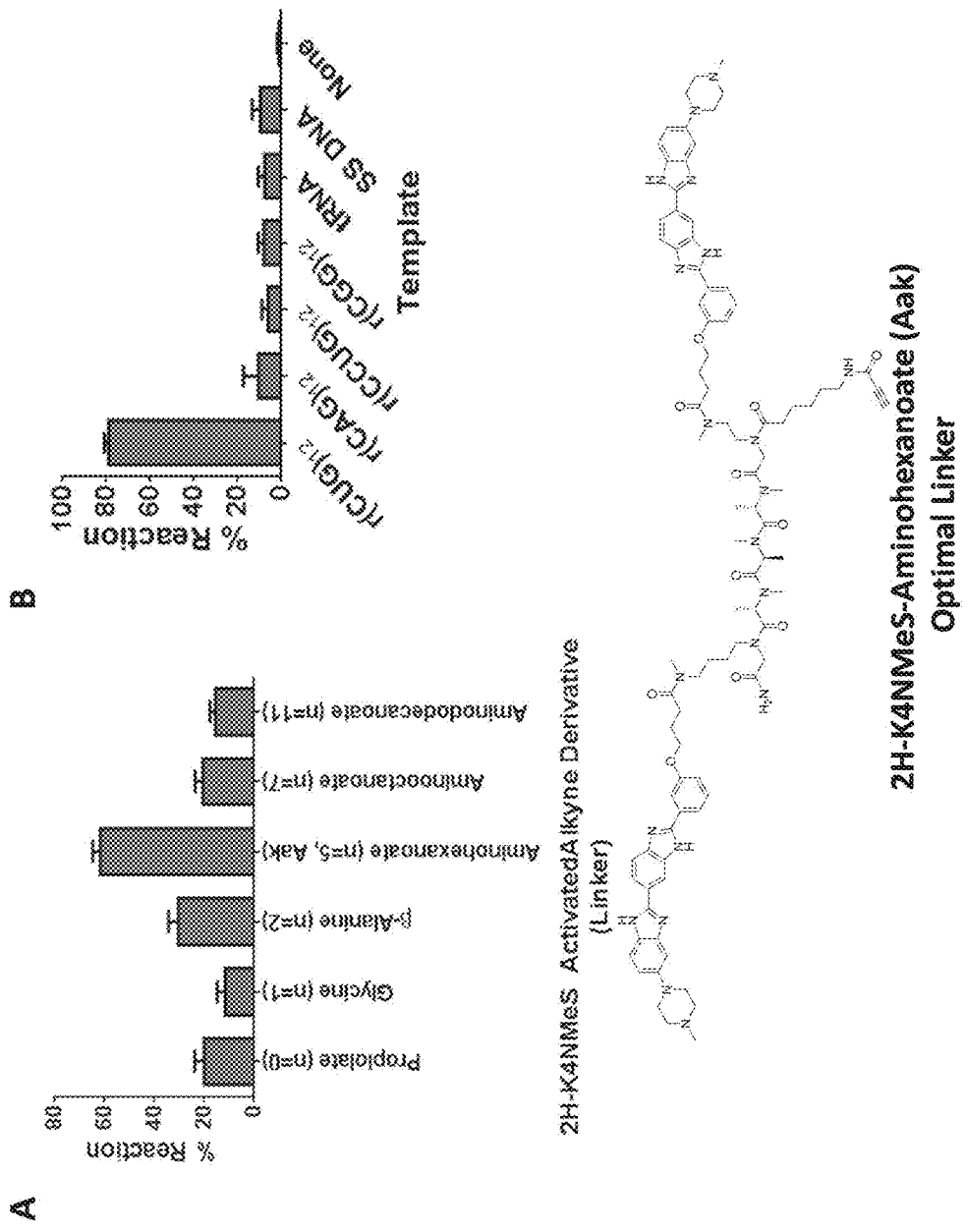

FIG. 27. Data for the in vitro oligomeric drug synthesis by using nucleic acids as catalysts. A, Results of probing linker length to determine the optimal distance for reaction; B Evaluation of in vitro drug synthesis between $N_3$-2H-K4NMeS and 2H-K4NMeS-Aminohexanoate Aak in the presence of various RNAs.

Figure 28:
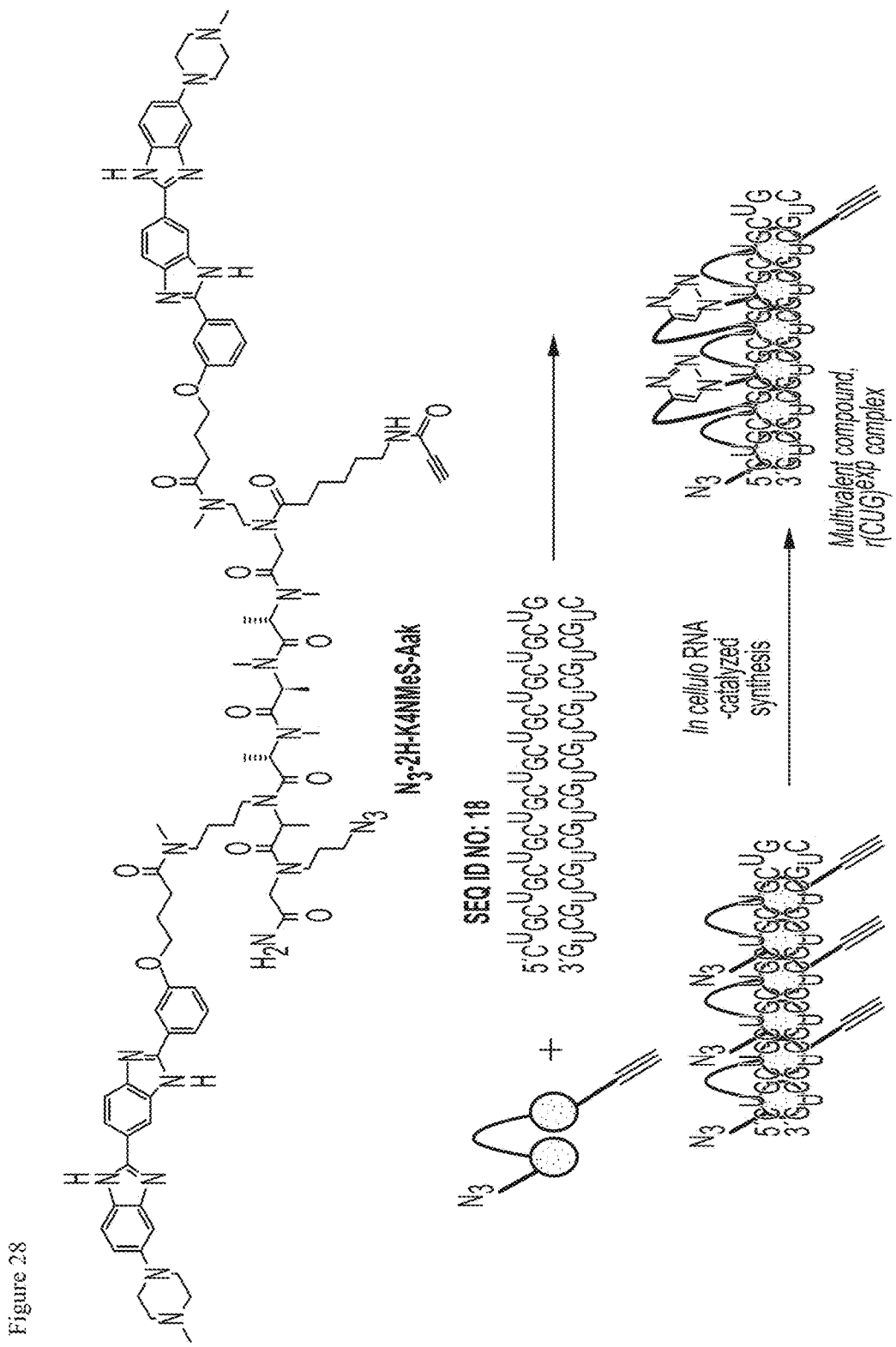

FIG. 28. The designer compound $N_3$-2H-K4NMeS-Aak that can form oligomeric species that has a azide and alkyne site on a single $r(CUG)^{exp}$ binding ligand.

Figure 29:
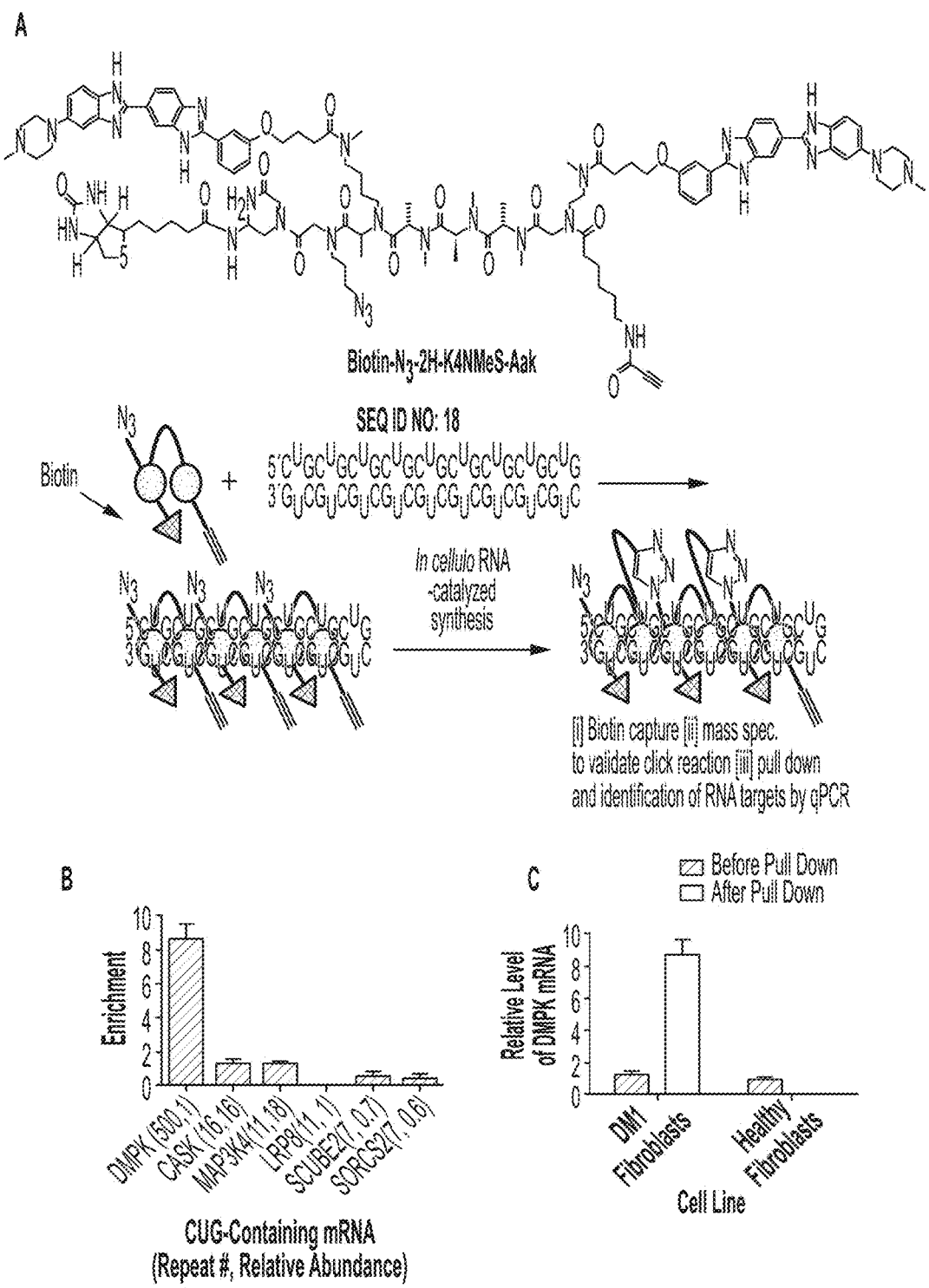

FIG. 29. In cellulo click chemistry by using $N_3$-2H-K4NMeS-Aak (FIG. 28) and scheme of Chem-React-BIP to pull down and quantify targets.

Figure 30:
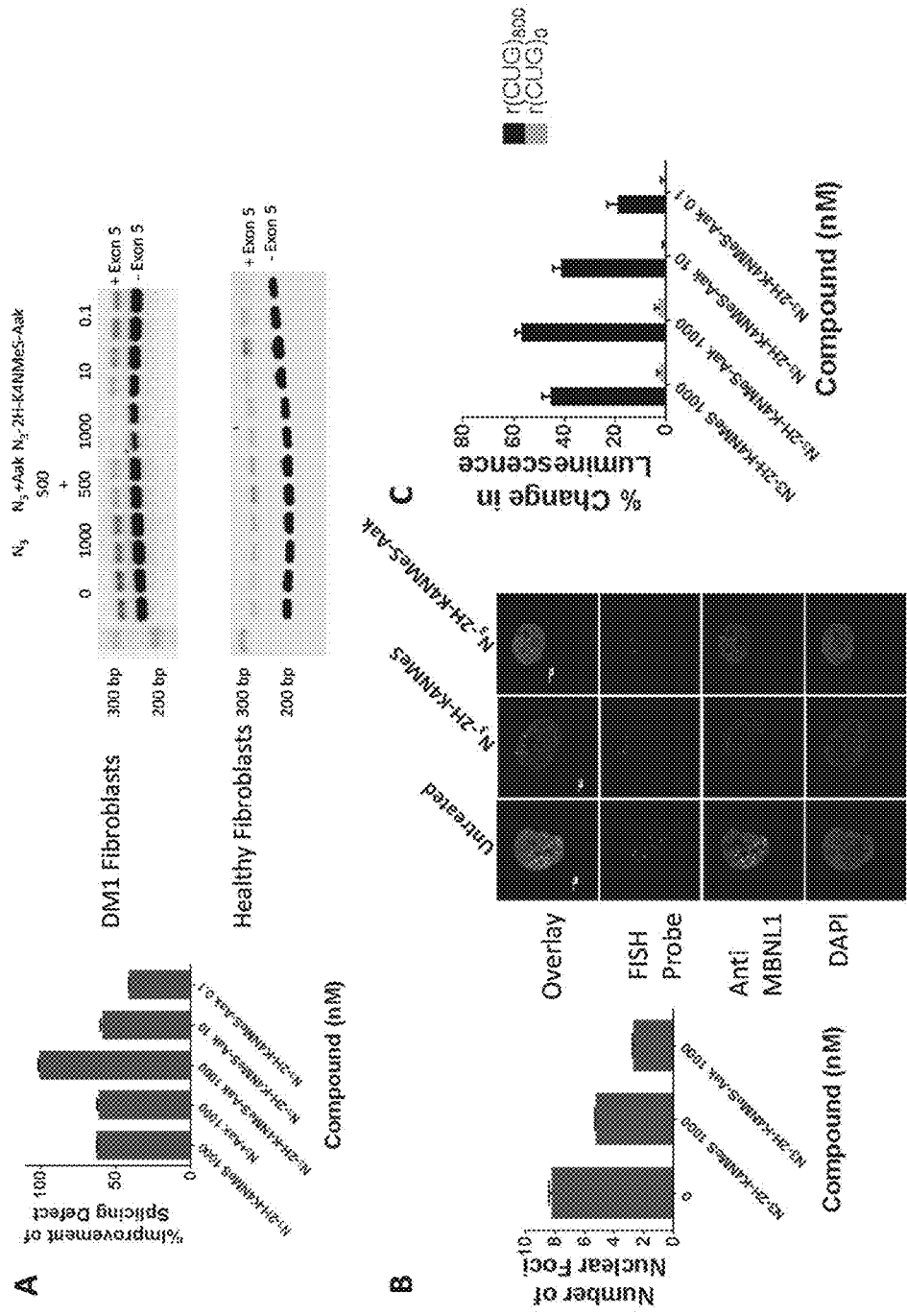

FIG. 30. Ability of in cellulo click compounds to improve A, Pre-mRNA splicing, B, Nuclear foci, and C, A translational defect that is associated with DM1.

Figure 31:
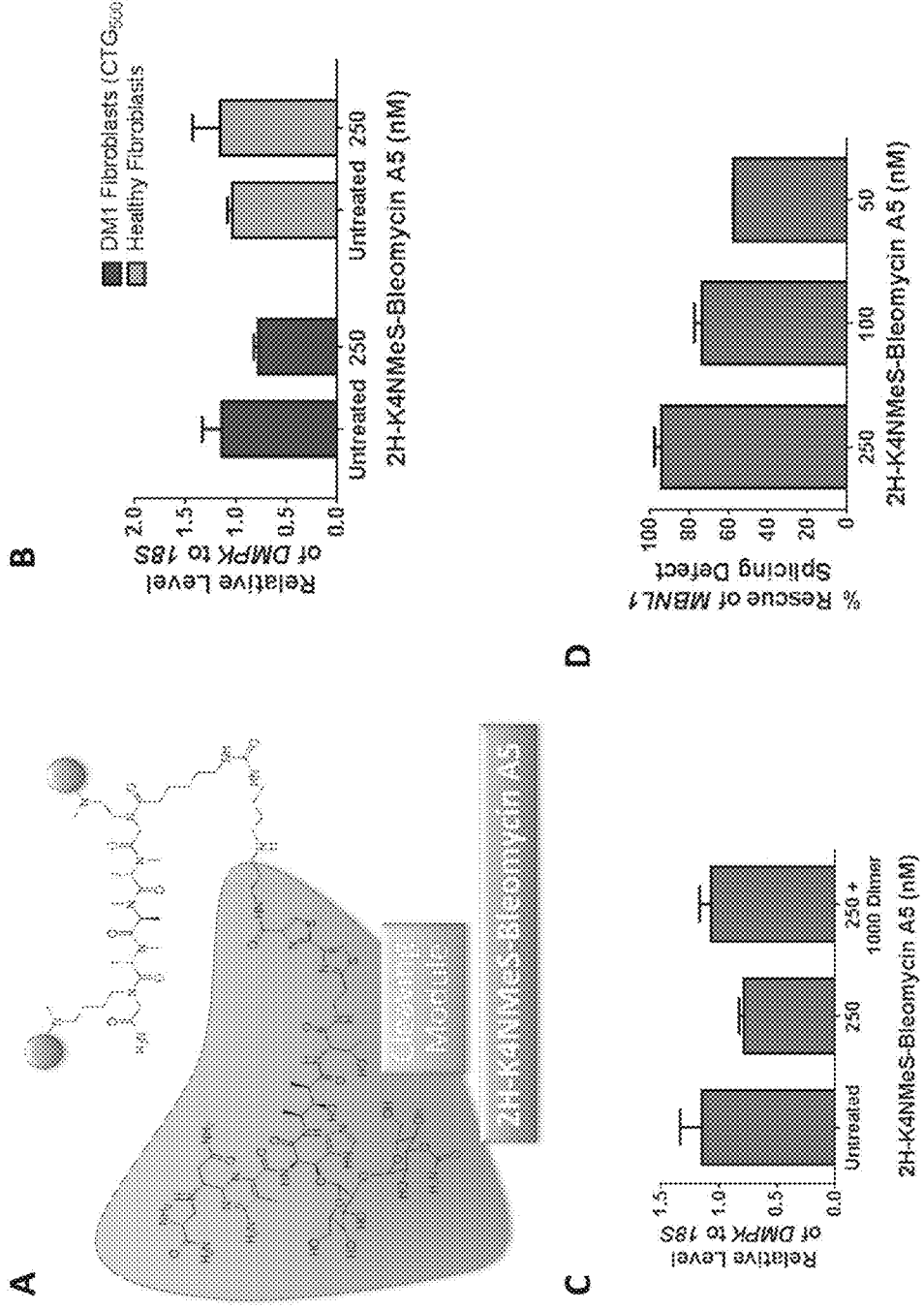

FIG. 31. A 2H-K4NMeS derivative that is conjugated to bleomycin to allow for the targeted cleavage of $r(CUG)^{exp}$ in DM1 patient-derived cells. A, structure of the compound; B, qRT-PCR data to show that the target is cleaved; C, competitive cleaving data in which 2H-K4NMeS-Bleomycin A5 and 2H-K4NMeS are co-added to cells showing that 2H-K4NMeS can inhibit targeted $r(CUG)^{exp}$ cleavage. D, Improvement of downstream DM1-associated pre-mRNA splicing defects.

Figure 32:
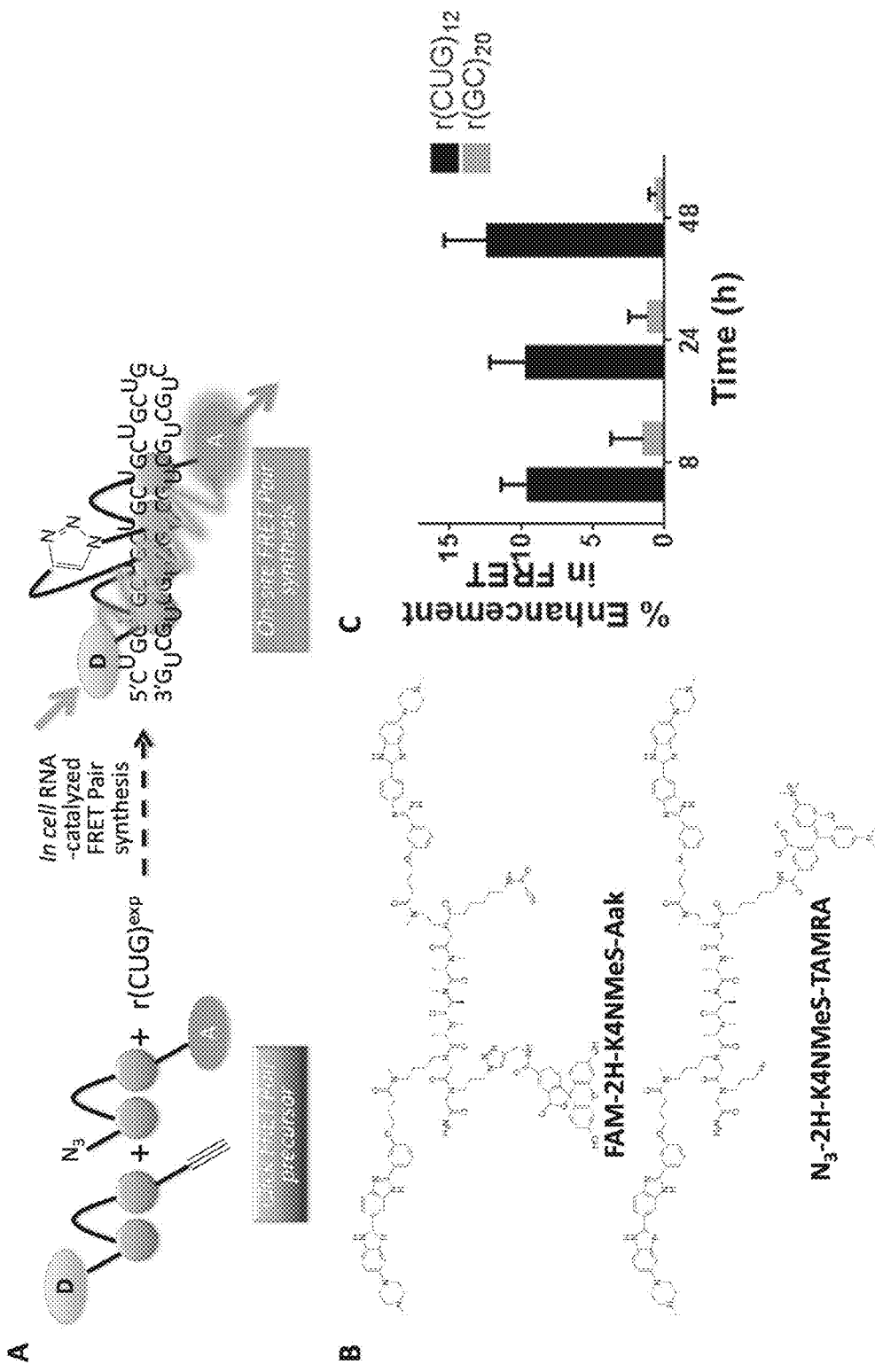

FIG. 32. Scheme of the fluorescence resonance energy transfer (FRET) experiment to synthesize a FRET sensor by using $r(CUG)^{exp}$ as a catalyst. A, A schematic of the approach. B, Compounds used in these experiments. C, Representative data.

Figure 33:
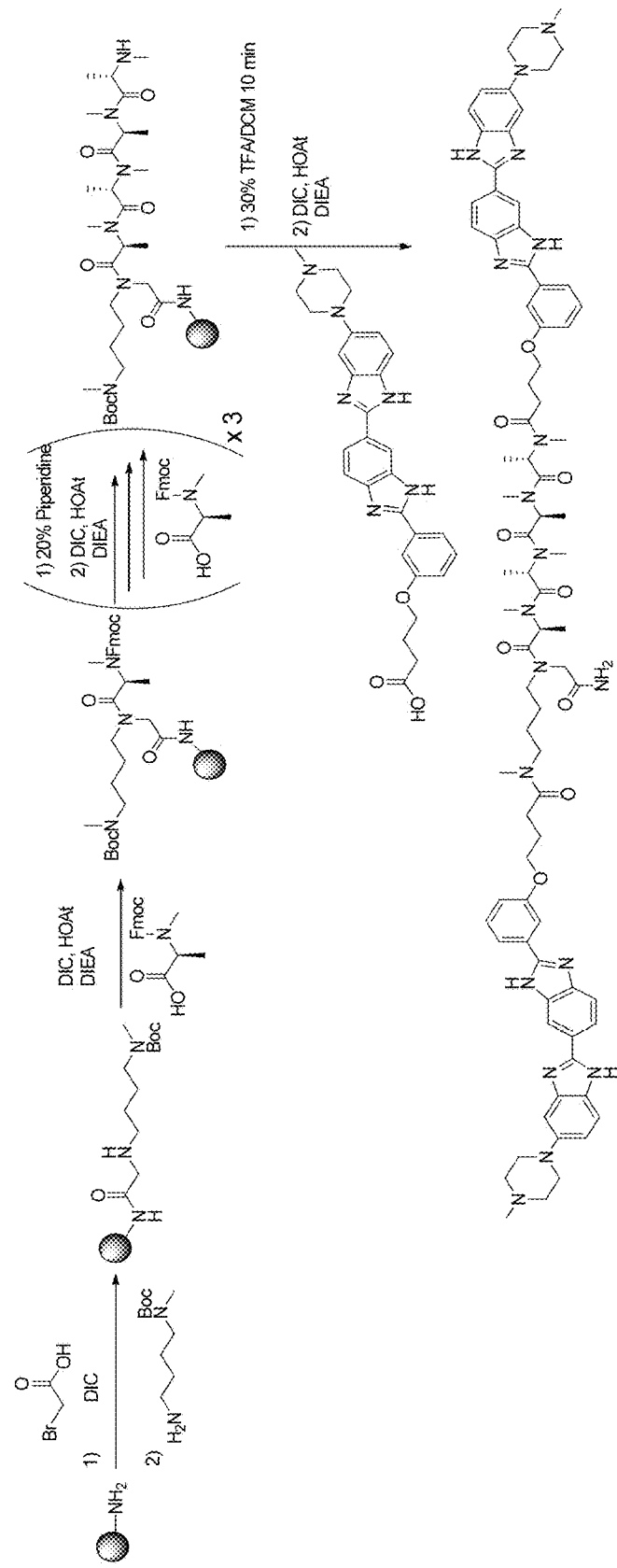

FIG. 33. Synthetic scheme for 2H-K4NMeS.

Figure 34:
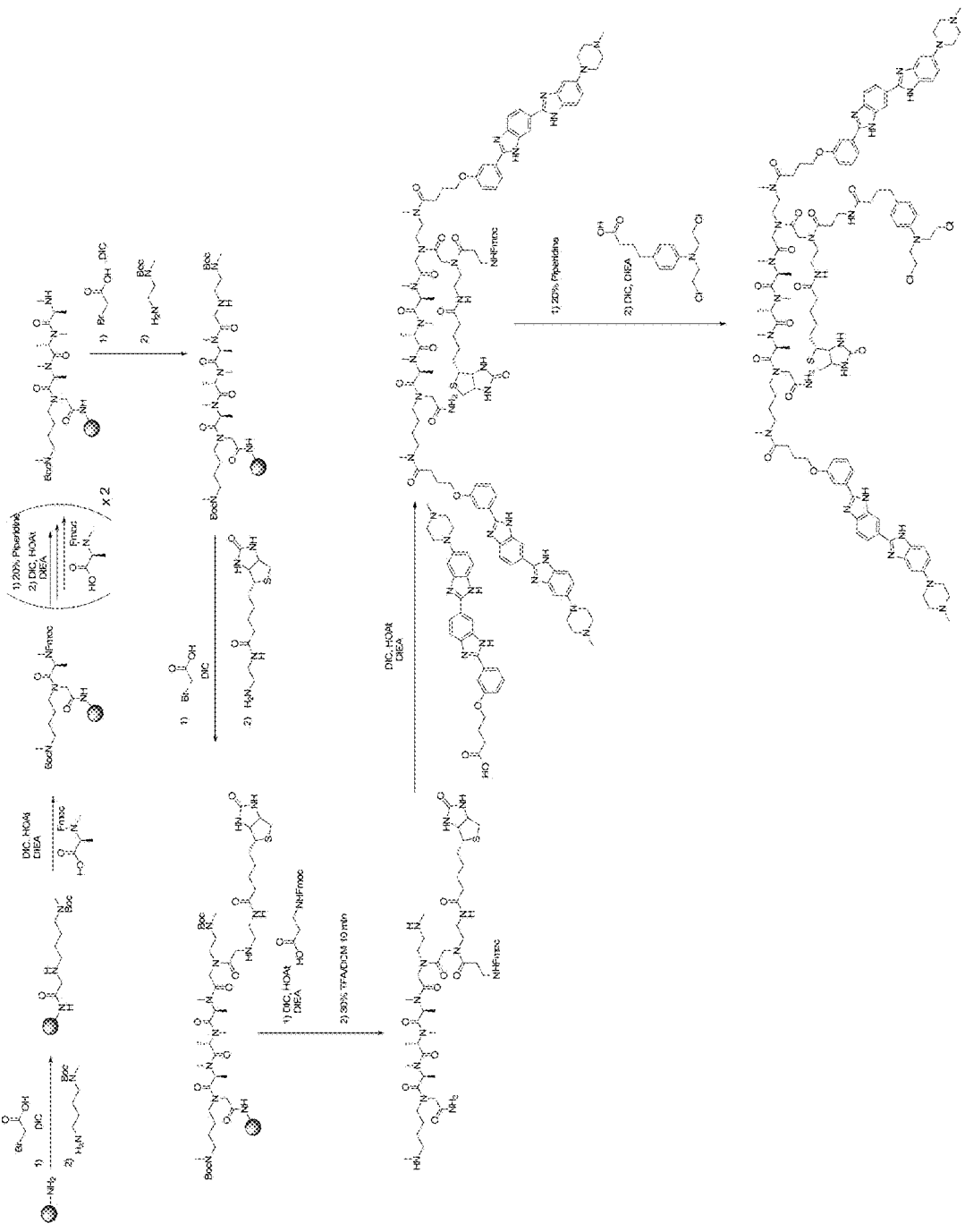

FIG. 34. Synthetic scheme for 2H-K4NMeS-CA-Biotin.

Figure 35:
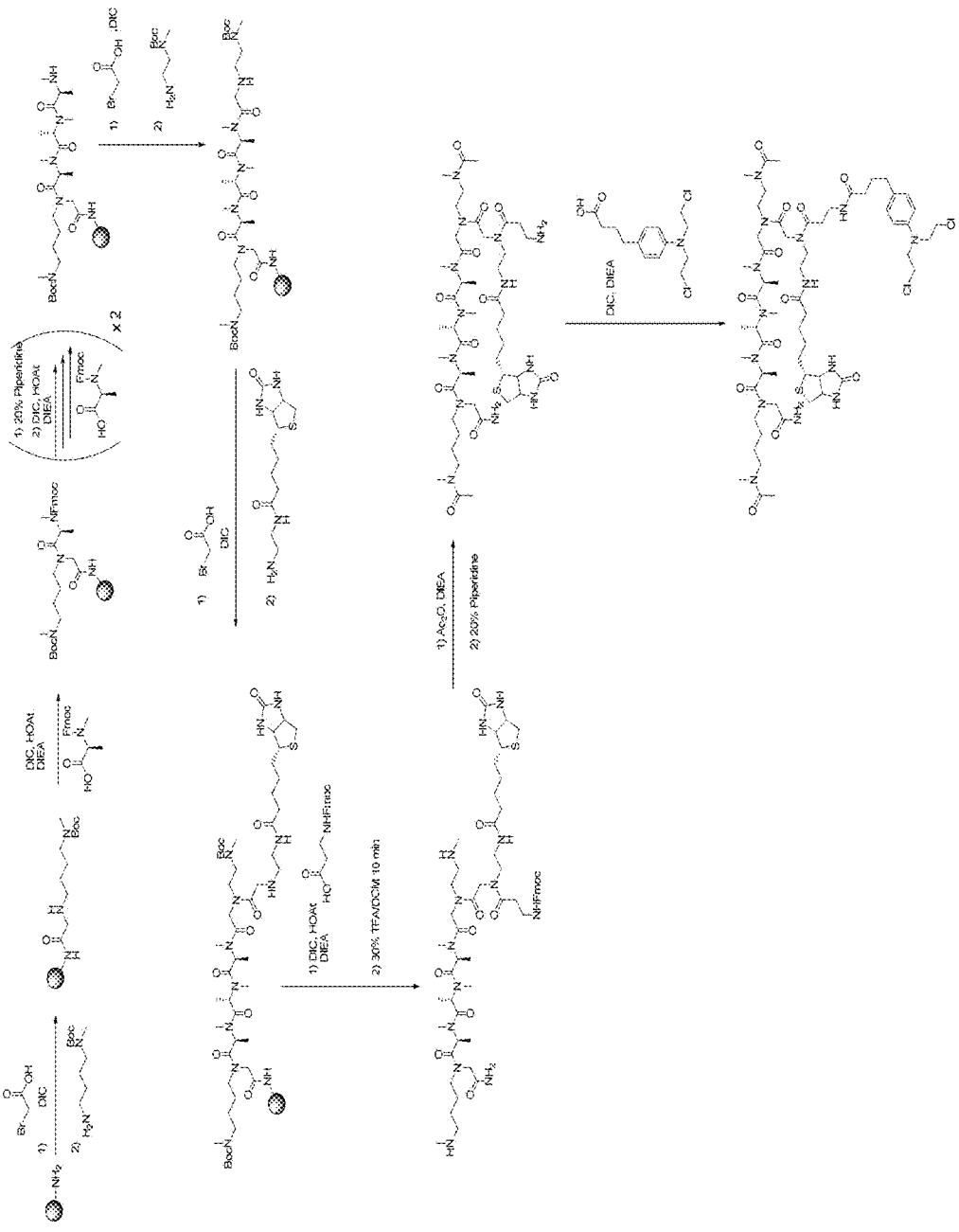

FIG. 35. Synthetic scheme for 2NAc-K4NMeS-CA-Biotin.

Figure 36:
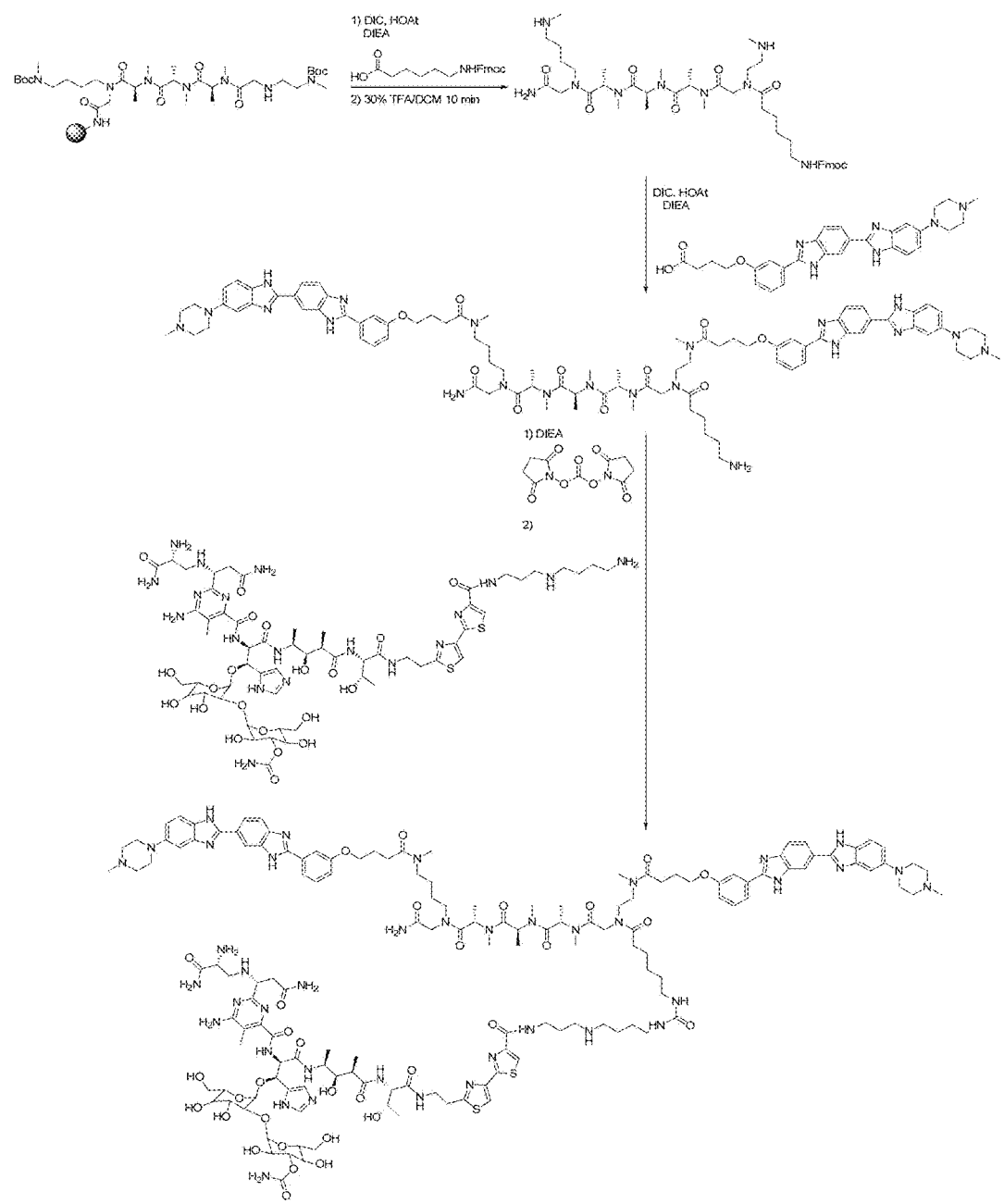

FIG. 36. Synthetic scheme for 2H-K4NMeS-Bleomycin A5.

Figure 37:
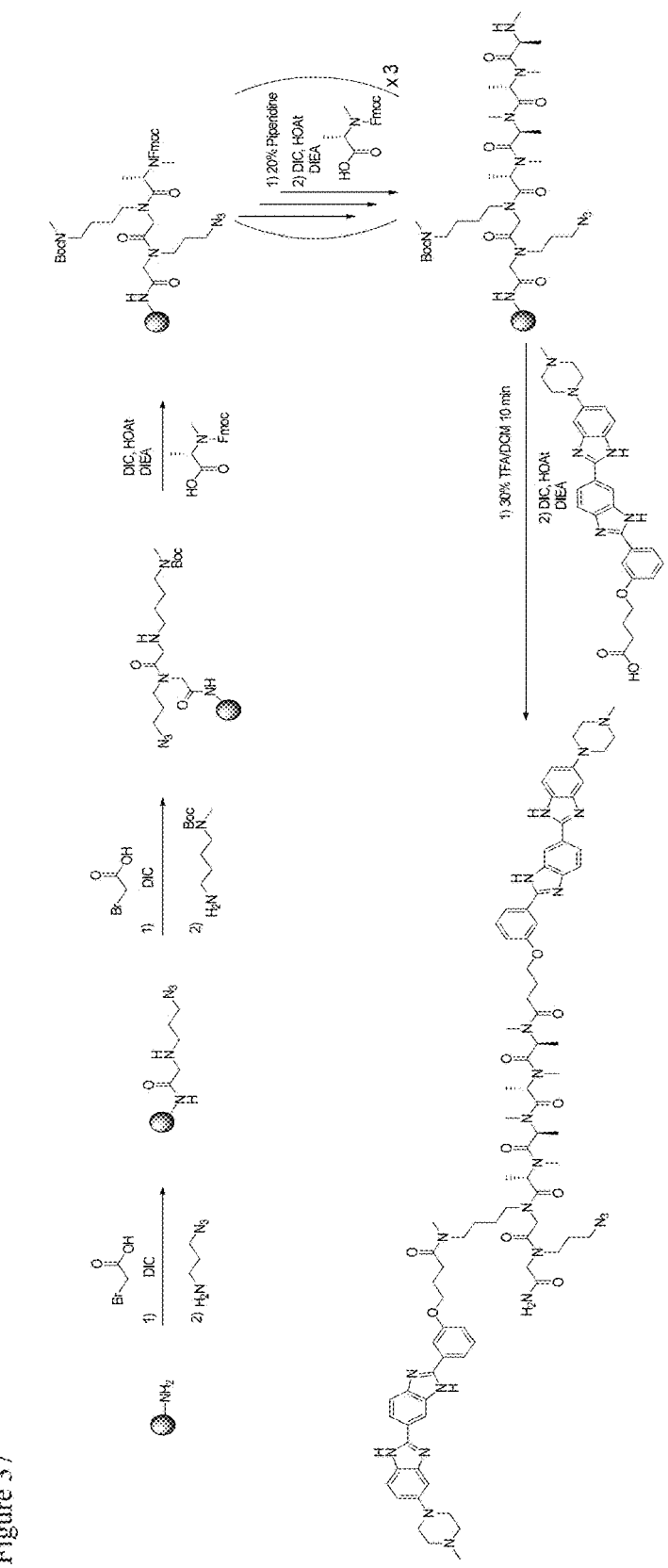

FIG. 37. Synthetic scheme for $N_3$-2H-K4NMeS.

Figure 38:
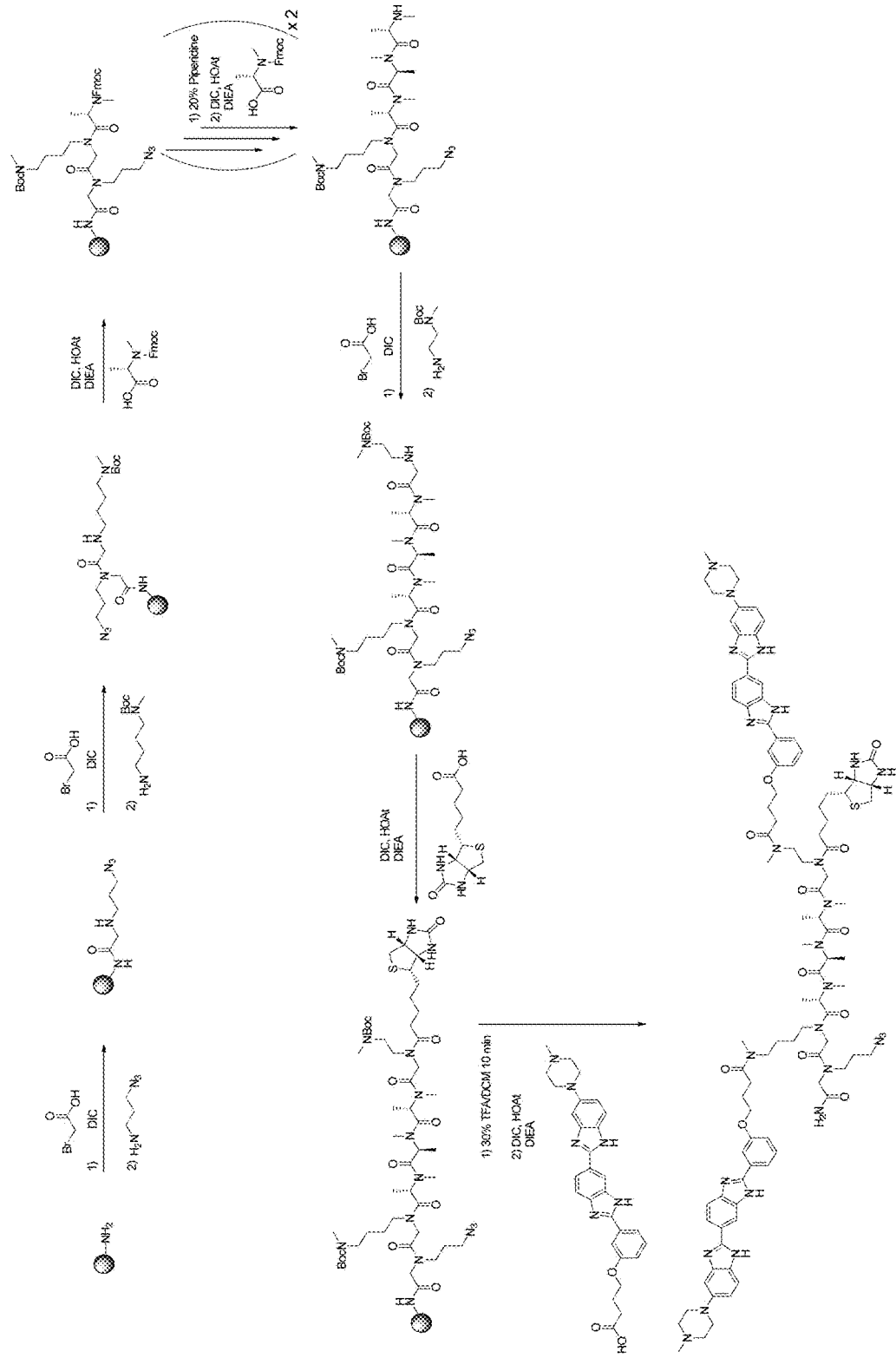

FIG. 38. Synthetic scheme for $N_3$-2H-K4NMeS-Biotin.

Figure 39:
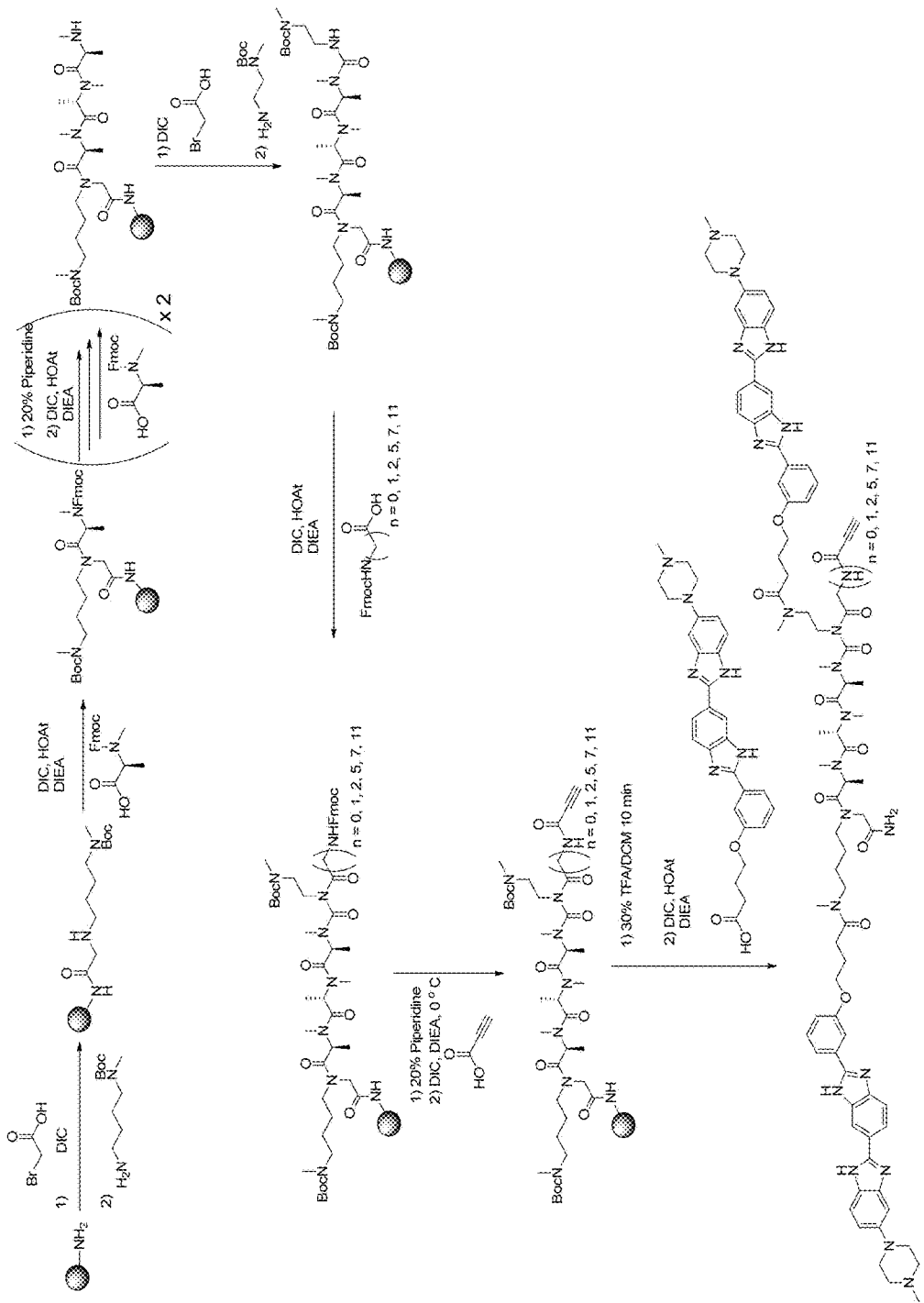

FIG. 39. Synthetic scheme for 2H-K4NMeS Activated Alkynes.

Figure 40:
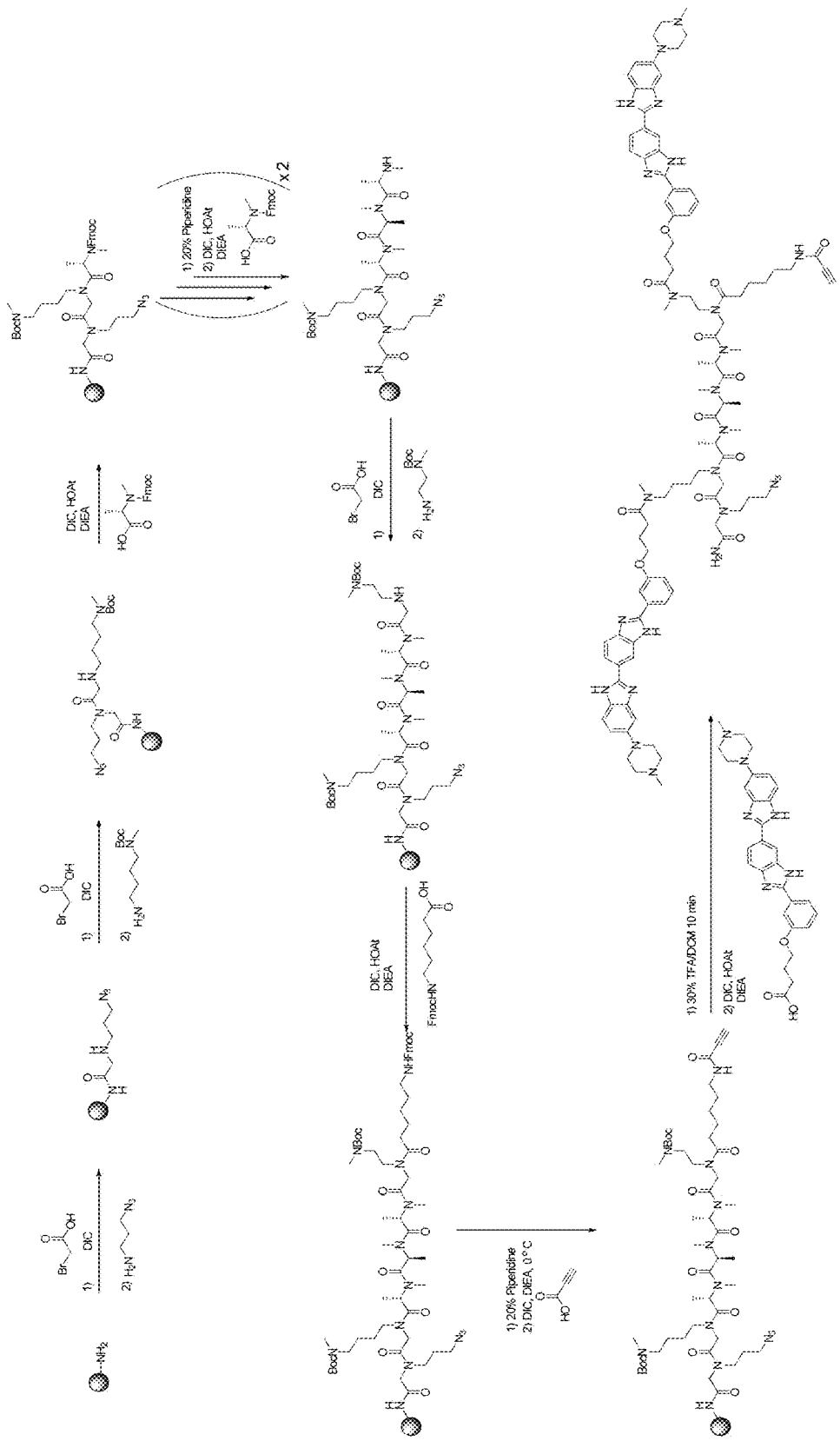

FIG. 40. Synthetic scheme for $N_3$-2H-K4NMeS-Aak.

Figure 41:
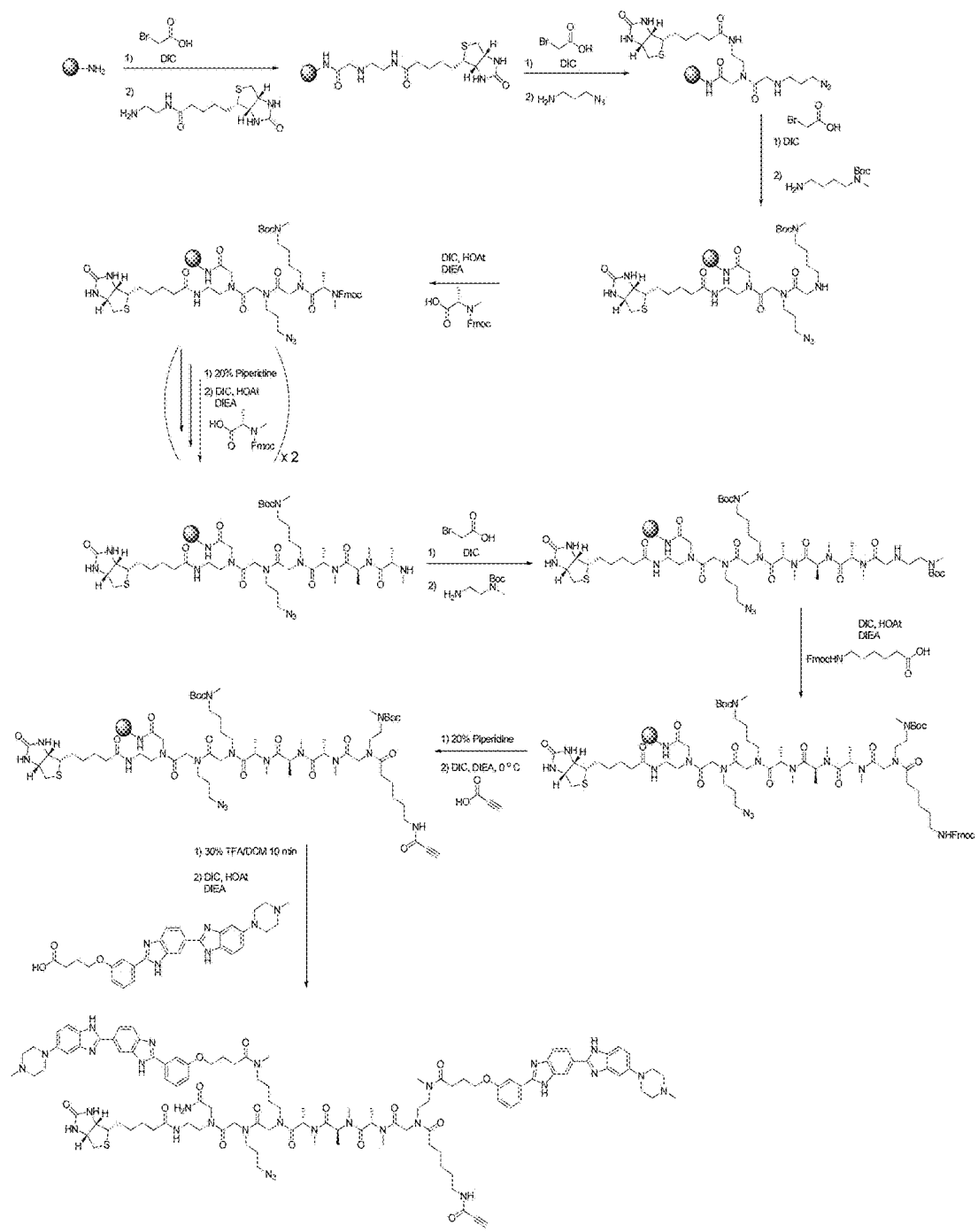

FIG. 41. Synthetic scheme for Biotin $N_3$-2H-K4NMeS-Aak.

Figure 42:
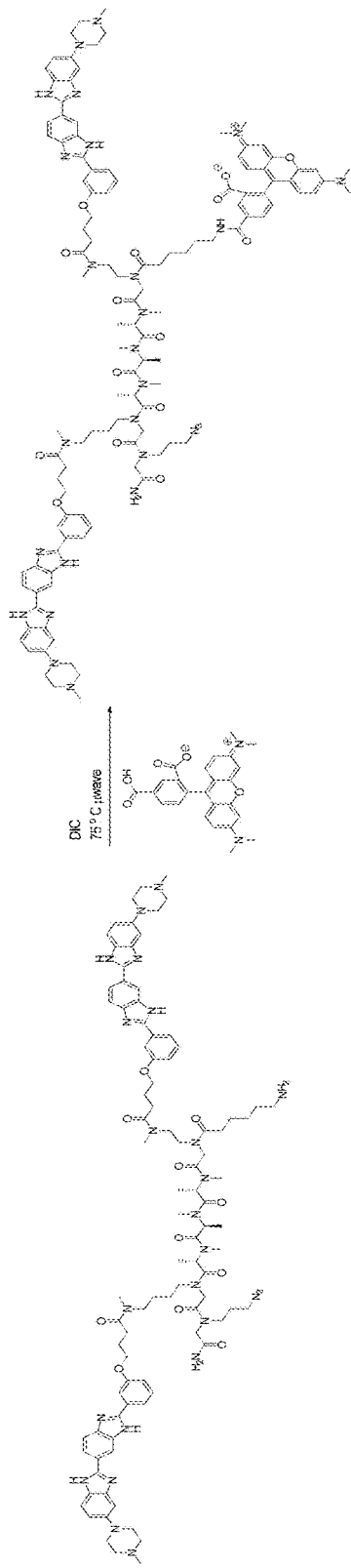

FIG. 42. Synthetic scheme for $N_3$-2H-K4NMeS-TAMRA.

Figure 43:
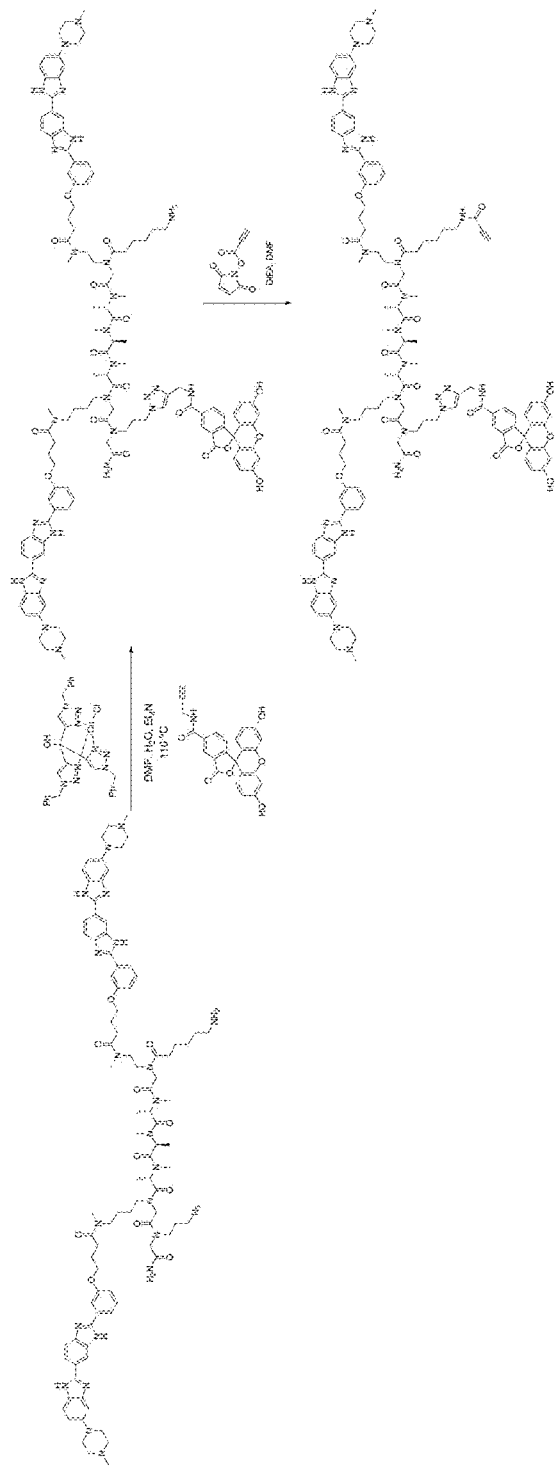

FIG. 43. Synthetic scheme for FAM-2H-K4NMeS-Aak.

DETAILED DESCRIPTION

Given the above considerations, we sought to develop a strategy to target RNA repeat expansions that could exploit the cellular permeability of the small molecule "modules" and the potency and selectivity of higher molecular weight, multivalent compounds. In situ click chemistry, via a 1,3 Huisgen dipolar cycloaddition reaction (HDCR), could provide such a strategy. That is, two modules would bind adjacent sites in the target, bringing otherwise unreactive groups into close proximity to form a covalent bond; in particular, azide and alkyne moieties react to form a stable triazole.[10] Indeed, this approach has been used in vitro to target acetylcholine esterase and the DNA minor groove.[10-11] Translating such an approach to cellular systems could be highly impactful, enabling the development of highly selective chemical biology probes yet this has not been previously demonstrated. Expanded repeating RNAs are perhaps ideal targets for this approach because they are modular like the compounds they will template (FIG. 1A).

The development of an in cellulo, in situ click approach for $r(CCUG)^{exp}$ was enabled by using a model of the binding of dimeric 6'-N-acylated kanamycin A compound (2K-4) to r(CCUG) repeats.[6a] Analysis of this model showed that an azido group at 6" position ($N_3$-K) and an alkyne group at 6' position (K-Ak) could be within close enough proximity to react upon binding to adjacent 2×2 nucleotide internal loops in r(CCUG)$^{exp}$ (FIG. 1B). Thus, when N$_3$-K and K-Ak are mixed in equal amounts, a dimer could be formed; likewise, a derivative that displays both a 6" azide and a 6' alkyne (N$_3$-K-Ak; FIG. 1B) could form an oligomer. We also synthesized a compound with an activated, electron deficient alkyne, N$_3$-K-Aak (FIG. 1A), which was employed by the Dervan group to assemble polyamides using DNA as a template.[11b] All compounds were synthesized by using variations of known routes (see Examples section).

Figure 4:
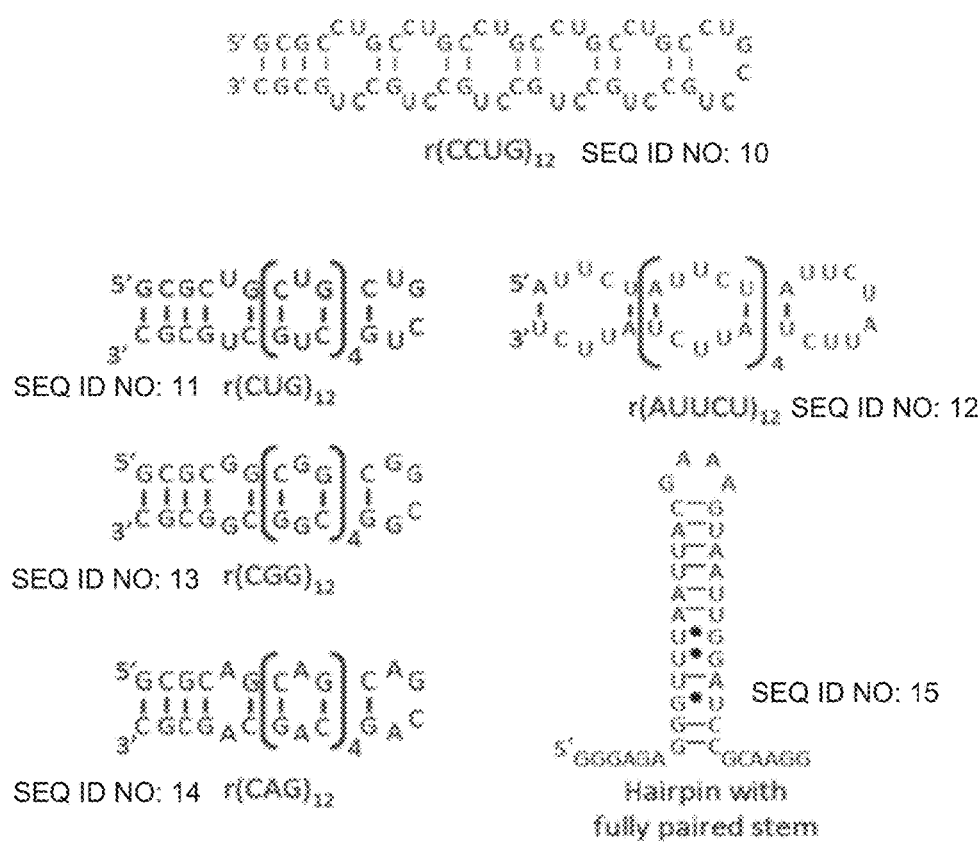
FIG. 4. Secondary structures of RNAs used for in vitro click reactions with $N_3$-K and K-Ak.
Figure 5:
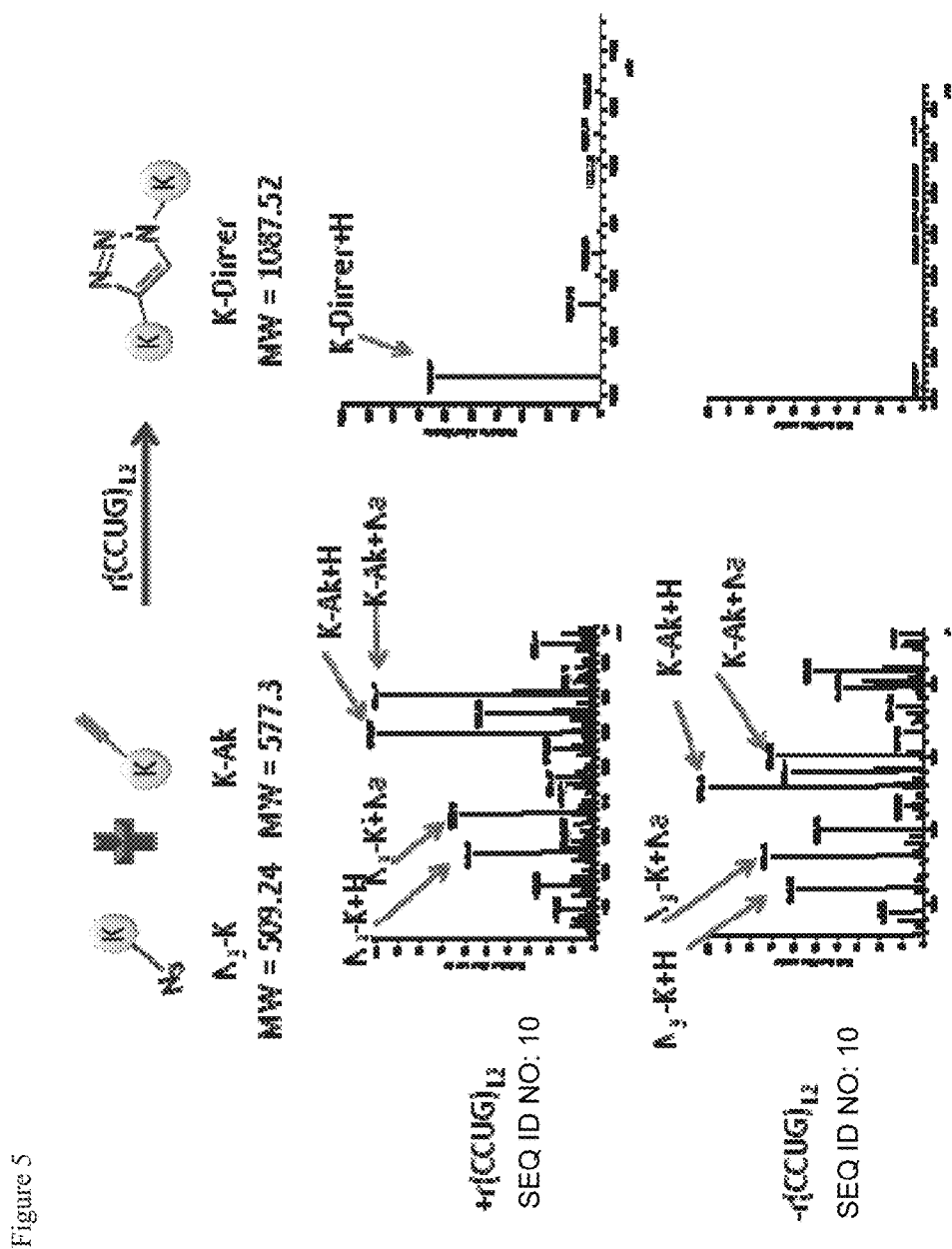
FIG. 5. Results of LC-MS analysis of in vitro click reactions between $N_3$-K and K-Ak in the presence and absence of r(CCUG)$_{12}$. These data show that a K dimer is formed in the presence of r(CCUG)$_{12}$ but not in its absence.
Figure 6:
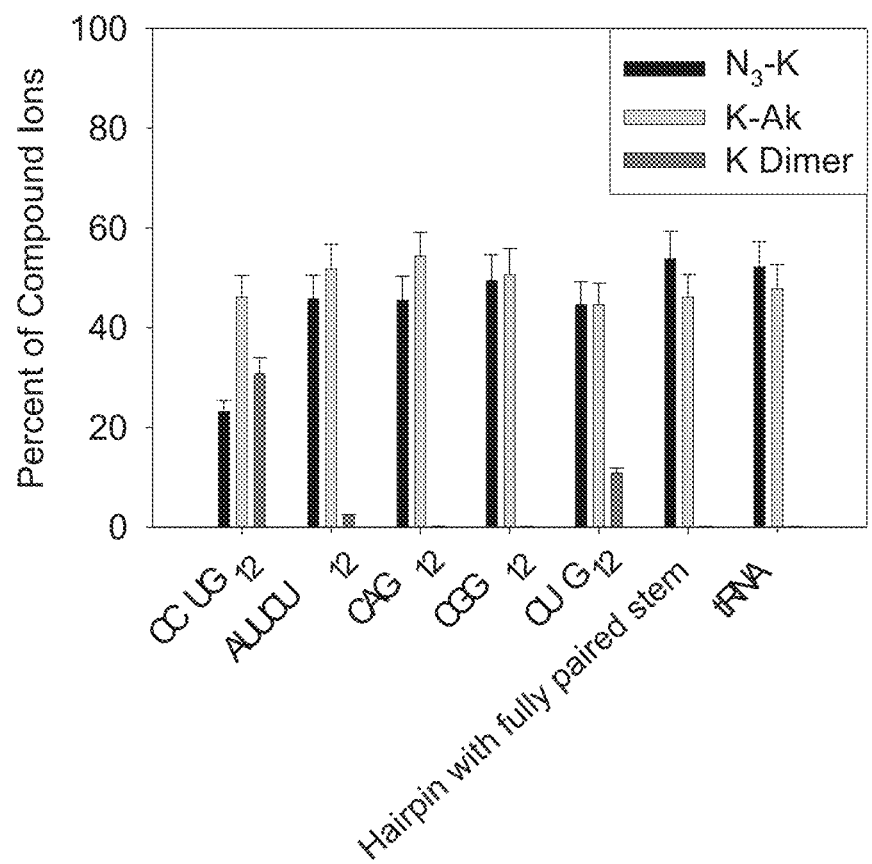
FIG. 6. Results of LC-MS analysis of in vitro click reactions between $N_3$-K and K-Ak in the presence and absence of r(CCUG)$_{12}$, r(AUUCU)$_{12}$, r(CAG)$_{12}$, r(CGG)$_{12}$, r(CUG)$_{12}$, an RNA hairpin with a fully paired stem, and brewer's yeast tRNA. These data show that the formation of a K dimer is selectively catalyzed by r(CCUG)$_{12}$ (n=3).

We first tested the ability of r(CCUG)$_{12}$ (FIG. 4) to template assembly of K oligomers in vitro. After incubation, reaction products were analyzed by mass spectrometry. Indeed, higher valency compounds were formed in the presence of r(CCUG)$_{12}$ but not in its absence (FIG. 5). To determine if this templated reaction was specific to r(CCUG)$_{12}$, we studied the abilities of other RNAs to catalyze oligomer formation including r(CUG)$_{12}$, r(AUUCU)$_{12}$, r(CGG)$_{12}$, r(CAG)$_{12}$, an RNA hairpin with a fully paired stem, and tRNA (FIG. 4). Importantly, no significant reaction products were observed for all RNAs, except for r(CUG)$_{12}$ in which a small amount of dimer was observed (<10%; FIG. 6). It is not surprising that r(CUG)$_{12}$ templated a small amount of dimer as it binds K, albeit with a much lower affinity than r(CCUG)$_{12}$.[13] Further, the optimal distance that separates K RNA-binding modules in a multivalent compound is much shorter for r(CUG)$_{12}$ than r(CCUG)$_{12}$.[13] Taken together, these studies illustrate that the templated reaction is selective for r(CCUG)$_{12}$ and is controlled by the positioning of functional groups, the RNA binding module, and the RNA target (FIG. 6). These studies provided impetus for testing this approach in cellular systems and to study the biological impact of the templated compounds on DM2-associated defects, which include alternative pre-mRNA splicing defects and formation of nuclear foci.[3a]

Figure 7:
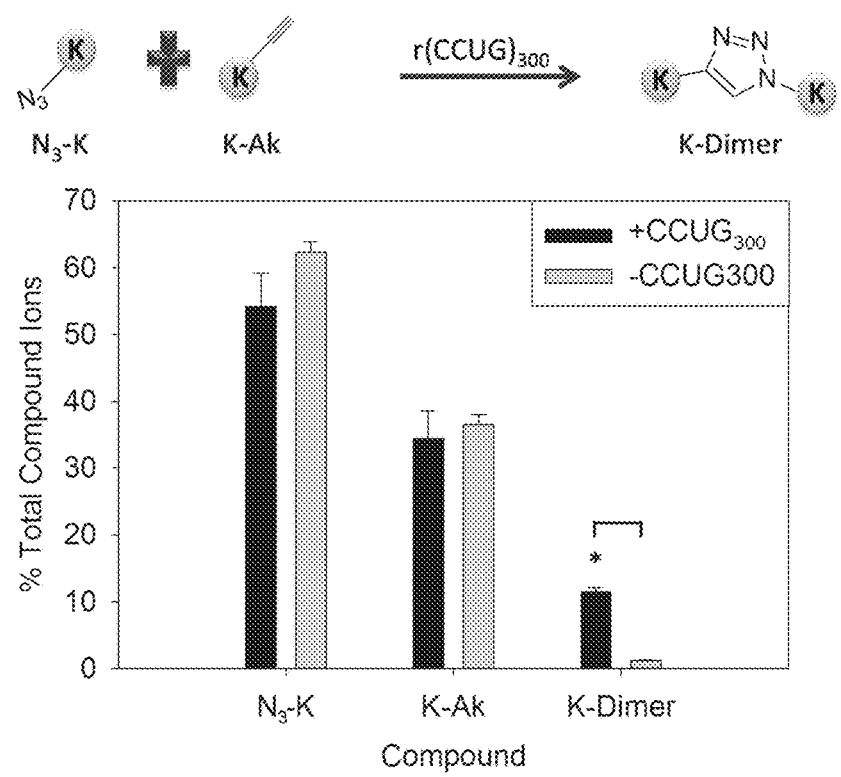
FIG. 7. Results of LC-MS analysis of in cellulo click reactions between $N_3$-K and K-Ak in the presence and absence of r(CCUG)$_{300}$. These data show that a K dimer is formed in the presence of r(CCUG)$_{300}$ but not in its absence. "*" indicates $p<0.05$ as determined by a two-tailed Student t-test (n=3).
Figure 8:
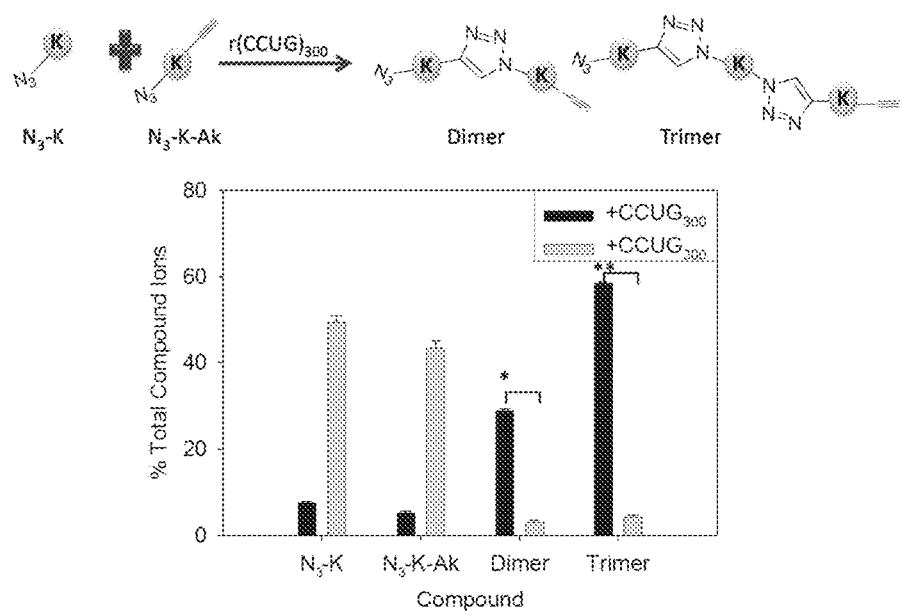
FIG. 8. Results of LC-MS analysis of in cellulo click reactions between $N_3$-K and $N_3$-K-Ak in the presence and absence of r(CCUG)$_{300}$. These data show that a dimer and a trimer are formed in the presence of r(CCUG)$_{300}$ but not in its absence. $N_3$-K was used to limit the extent of polymerization to facilitate LC-MS analysis (see "Identification of in cellulo clicked products by mass spectrometry"). "*" indicates $p<0.05$; "**" indicates $p<0.01$ as determined by a two-tailed Student t-test (n=3).
Figure 9:
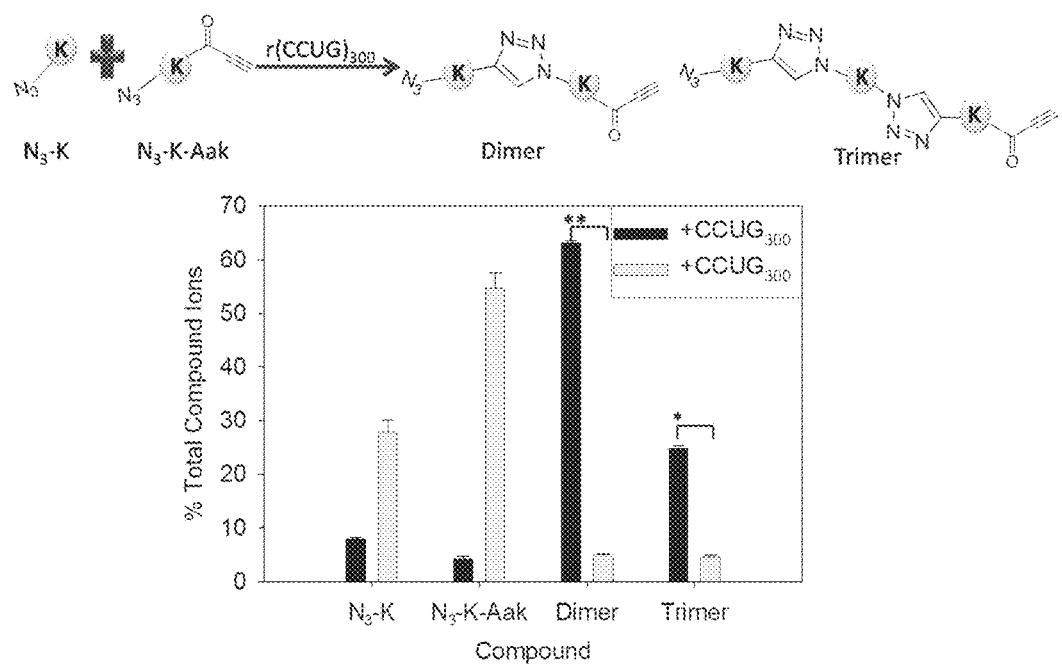
FIG. 9. Results of LC-MS analysis of in cellulo click reactions between $N_3$-K and $N_3$-K-Aak in the presence and absence of r(CCUG)$_{300}$. These data show that a dimer and a trimer are formed in the presence of r(CCUG)$_{300}$ but not in its absence. $N_3$-K was used to limit the extent of polymerization to facilitate LC-MS analysis (see "Identification of in cellulo clicked products by mass spectrometry"). "*" indicates $p<0.05$; "**" indicates $p<0.01$ as determined by a two-tailed Student t-test (n=3).
Figure 10:
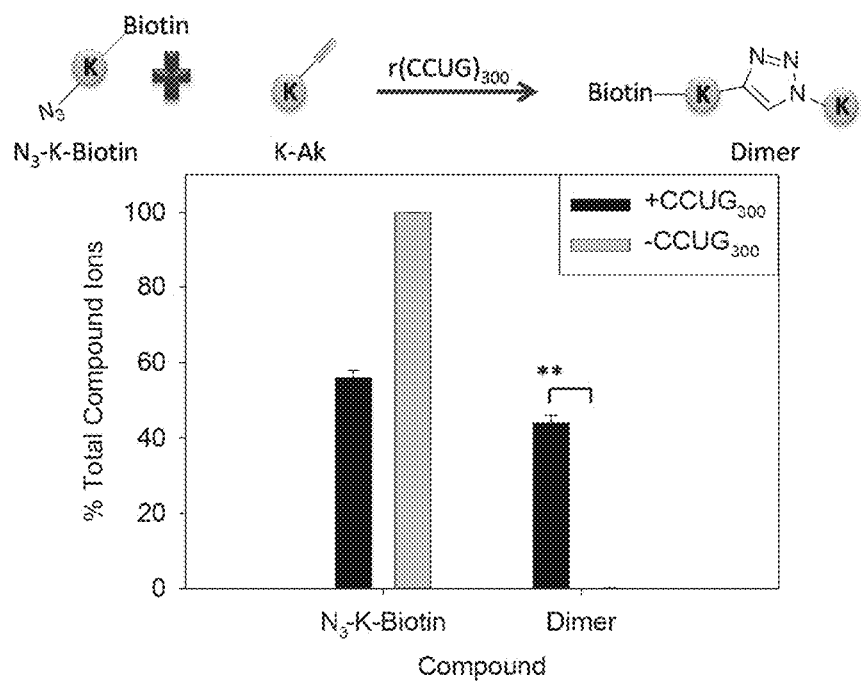
FIG. 10. Results of LC-MS analysis of pulled-down, biotin-tagged compounds from in cellulo click reactions between $N_3$-K-Biotin and K-Ak in the presence and absence of r(CCUG)$_{300}$. These data show that a biotinylated K dimer is formed in the presence of r(CCUG)$_{300}$ but not in its absence. "**" indicates $p<0.01$ as determined by a two-tailed Student t-test (n=3).
Figure 11:
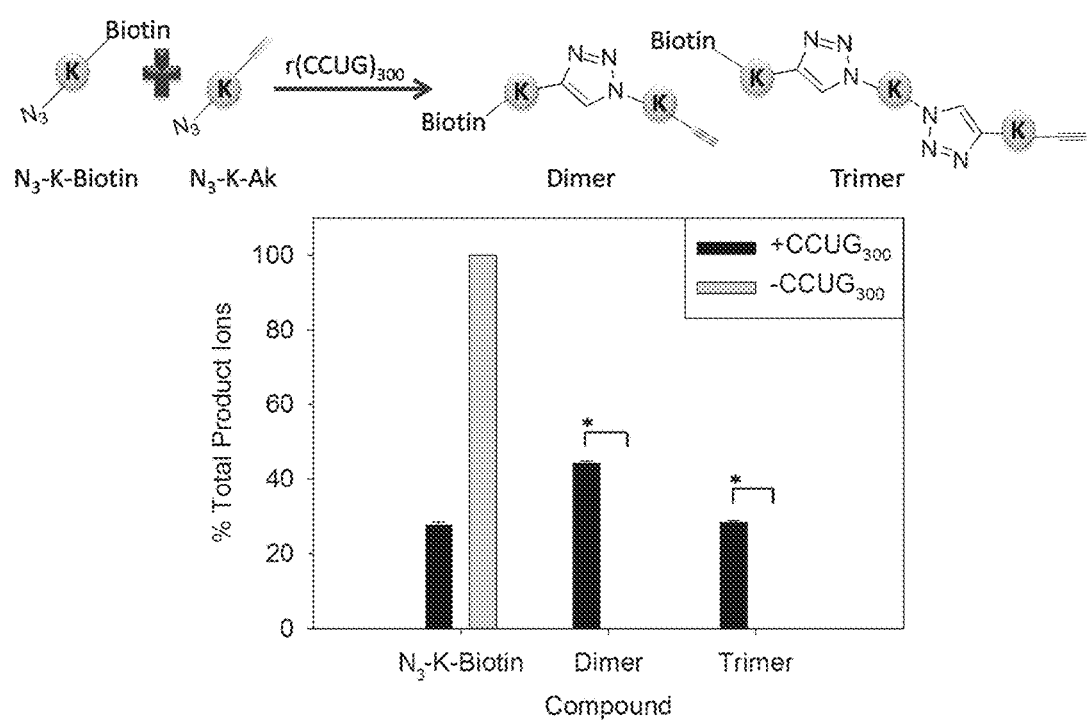
FIG. 11. Results of LC-MS analysis of pulled-down, biotin-tagged compounds from in cellulo click reactions between $N_3$-K-Biotin and $N_3$-K-Ak in the presence and absence of r(CCUG)$_{300}$. These data show that a dimer and a trimer are formed in the presence of r(CCUG)$_{300}$ but not in its absence. $N_3$-K-Biotin was used to limit the extent of polymer formation and facilitate LC-MS analysis (see "Identification of in cellulo clicked products by mass spectrometry"). "*" indicates $p<0.05$ as determined by a two-tailed Student t-test (n=3).
Figure 12:
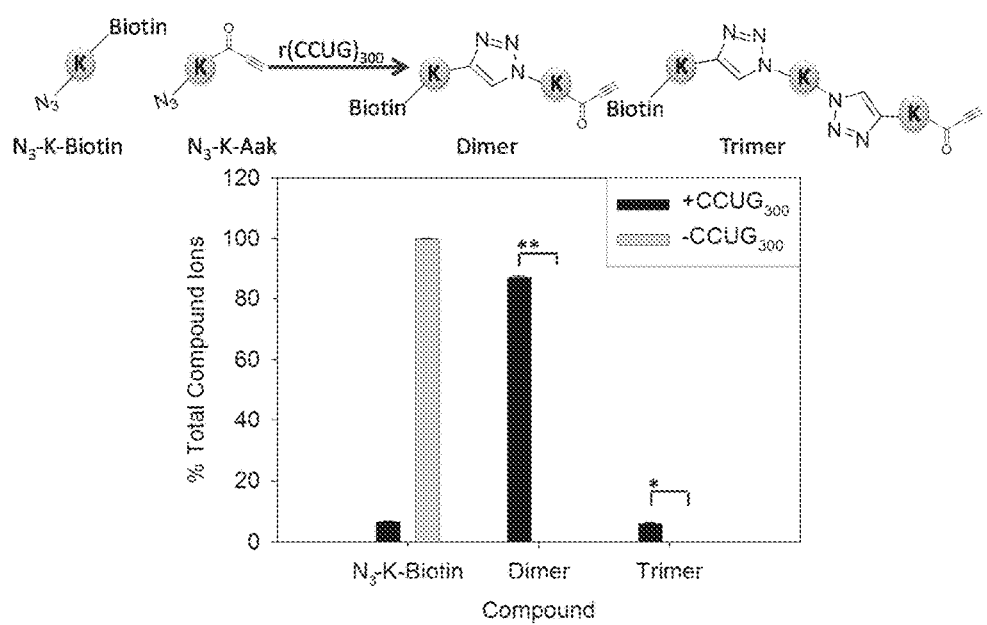
FIG. 12. Results of LC-MS analysis of pulled-down, biotin-tagged compounds from in cellulo click reactions between $N_3$-K-Biotin and $N_3$-K-Aak in the presence and absence of r(CCUG)$_{300}$. These data show that a dimer and a trimer are formed in the presence of r(CCUG)$_{300}$ but not in its absence. $N_3$-K-Biotin was used to limit the extent of polymer formation and facilitate LC-MS analysis (see "Identification of in cellulo clicked products by mass spectrometry"). "*" indicates $p<0.05$; "**" indicates $p<0.01$ as determined by a two-tailed Student t-test (n=3).
Figure 13:
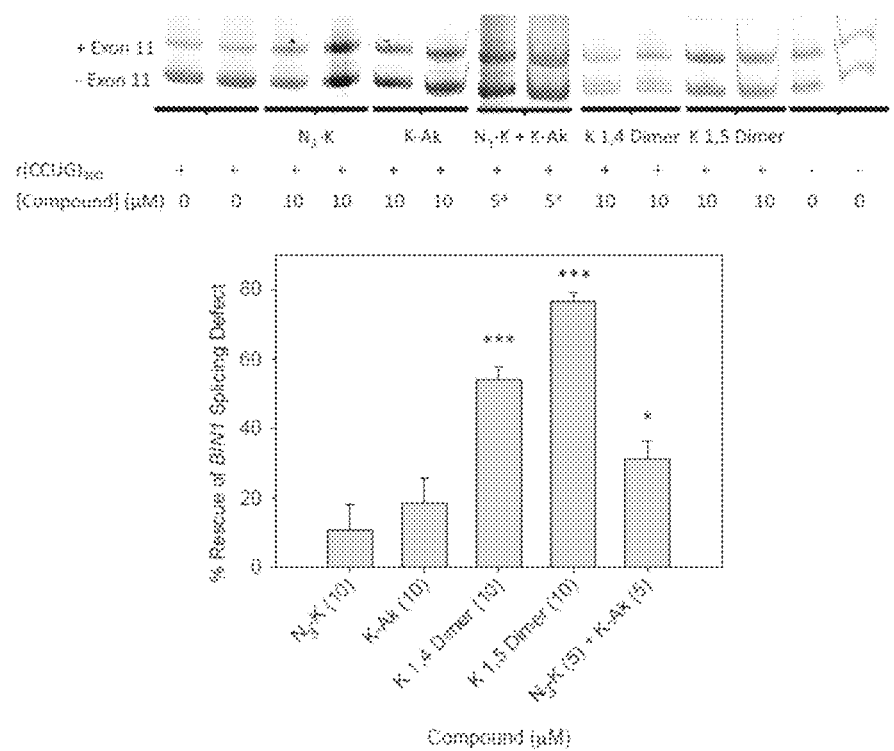
FIG. 13. Top, Representative gel images demonstrating the effect of K derivatives on BIN1 alternative splicing patterns. A 1:1 mixture of $N_3$-K and K-Ak improves BIN1 patterns to a similar extent as pre-synthesized dimers. Bottom, Quantification of BIN1 alternative splicing patterns in treated and untreated cells. The activities of monomers $N_3$-K and K-Ak were compared to pre-synthesized dimers as well as an equimolar mixture of each monomer. The pre-synthesized dimers improved splicing to the greatest extent while a mixture of azide and alkyne monomers improved splicing to a greater extent than each monomer alone. "*" indicates $p<0.05$; "***" indicates $p<0.001$ as determined by a two-tailed Student t-test (n≥3).
Figure 14:
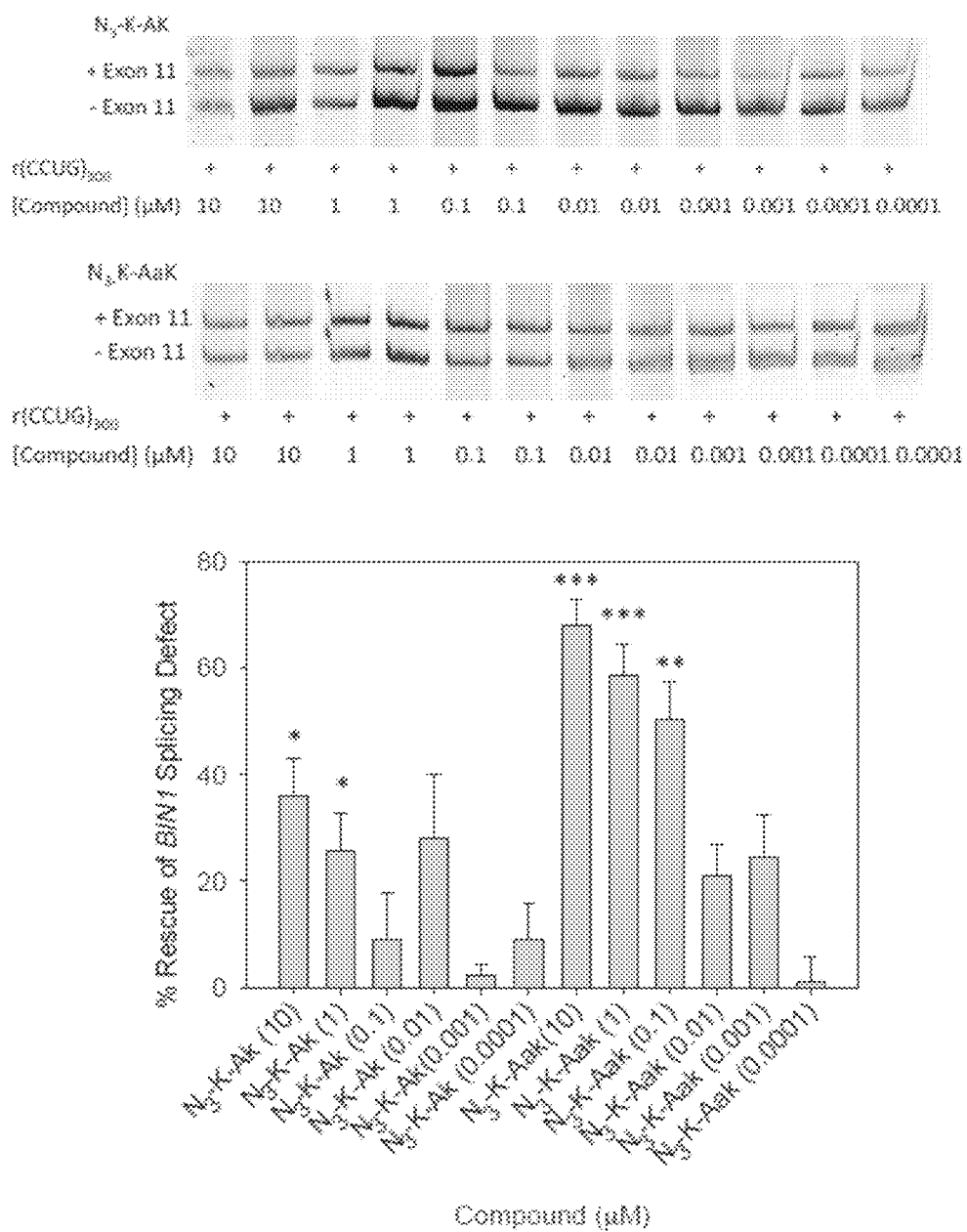
FIG. 14. Top, Representative gel images of BIN1 splicing patterns in cells treated with $N_3$-K-Ak. Improvement in splicing patterns was observed when cells were treated with 10 and 1 μM $N_3$-K-Ak. Middle, Representative gel images of BIN1 splicing patterns in cells treated with $N_3$-K-Aak. Improvement in splicing patterns was observed when cells were treated with 10 μM, 1 μM, and 100 nM $N_3$-K-Ak. Bottom, Quantification of BIN1 splicing patterns in untreated cells and cells treated with oligomerizable K compounds. $N_3$-K-Aak was the most potent compound evaluated. It significantly improves BIN1 pre-mRNA splicing defects at nanomolar concentrations and is 1000 times more potent than K monomers. "*" indicates $p<0.05$; "**"

To confirm that multivalent compounds are indeed templated in cellulo, a cellular model system in which r(CCUG)$_{300}$ is expressed was employed.[14] Cells were co-treated with N$_3$-K and N$_3$-K-Ak or N$_3$-K-Aak. N$_3$-K was used to poison the reaction in order to limit the molecular weight of the products, allowing for mass spectral analysis. After treatment, reaction products were partially purified from cell lysates by precipitating cellular material and proteins with organic solvent. Mass spectral analysis of purified fractions showed that oligomerization occurred in cells expressing r(CCUG)$_{300}$ as both dimeric and trimeric reaction products are observed when cells were treated with N$_3$-K-Ak or N$_3$-K-Aak (FIGS. 7-9). Importantly, oligomerization is not observed in cells that do not express the RNA (FIGS. 7-9). Thus, templated synthesis only occurs in disease-affected cells, suggesting that r(CCUG)$_{300}$ catalyzes the synthesis of its own inhibitor.

To confirm the extent of templated reaction and that r(CCUG)$_{300}$ was indeed the catalyst for oligomerization, we developed and implemented an approach termed ChemReactBIP (Chemical Reactivity and Binding Isolated by Pull Down; FIG. 2A). Cells were treated with K-Ak, N$_3$-K-Ak, or N$_3$-K-Aak in the presence of a kanamycin analogue that contains a biotin moiety at the 6' position (N$_3$-K-Biotin; FIGS. 20 & 10-12). N$_3$-K-Biotin terminates the polymerization reaction in cellulo and allows oligomerized compounds and their bound cellular targets to be captured with streptavidin beads after gentle lysis. (FIGS. 2B & C). In agreement with studies completed with N$_3$-K described above, oligomerized products were only formed in cells that express r(CCUG)$_{300}$ and that the conversion of monomer to products was greater with N$_3$-K-Aak than N$_3$-K-Ak, as expected.[11b] ChemReactBIP also allowed us to identify the cellular targets of the templated reaction. A qRT-PCR analysis of the pulled down fraction confirmed that r(CCUG)$_{300}$ is a major target of the products of N$_3$-K-Biotin and K-Ak, N$_3$-K-Ak, or N$_3$-K-Aak (FIG. 2C). The amount of r(CCUG)$_{300}$ target pulled down increases as a function of potency: N$_3$-K+K-Ak<N$_3$-K-Ak<N$_3$-K-Aak, vide infra. As observed in our other experiments, multivalent compounds were only observed when cells expressed r(CCUG)$_{300}$ (FIG. 2C).

As observed in other microsatellite disorders, the binding of various proteins to r(CCUG)$^{exp}$ causes formation of nuclear foci.[3a] Fluorescence in situ hybridization (FISH) with a dye-labeled oligonucleotide was employed to determine if our compounds inhibit formation of r(CCUG)$^{exp}$-containing nuclear foci (FIG. 3A). In untreated cells, the average number of foci per cell is 9±2. Treatment with N$_3$-K or K-Ak reduces the average number of foci per cell to 6±2 and 6±1, respectively. Treatment with an equimolar mixture of K-Ak and N$_3$-K (K-Ak+N$_3$-K) reduced foci to 1±1 per cell, similar to pre-synthesized dimers that mimic the reaction products of K-Ak and N$_3$-K (K 1,4 dimer and K 1,5 dimer; FIGS. 16 and 17). N$_3$-K-Ak and N$_3$-K-Aak, derivatives that click to self-oligomerize in cellulo, are even more potent, with <<1 foci per cell observed. Thus, the potential extent of oligomerization correlates with bioactivity.

Figure 2:
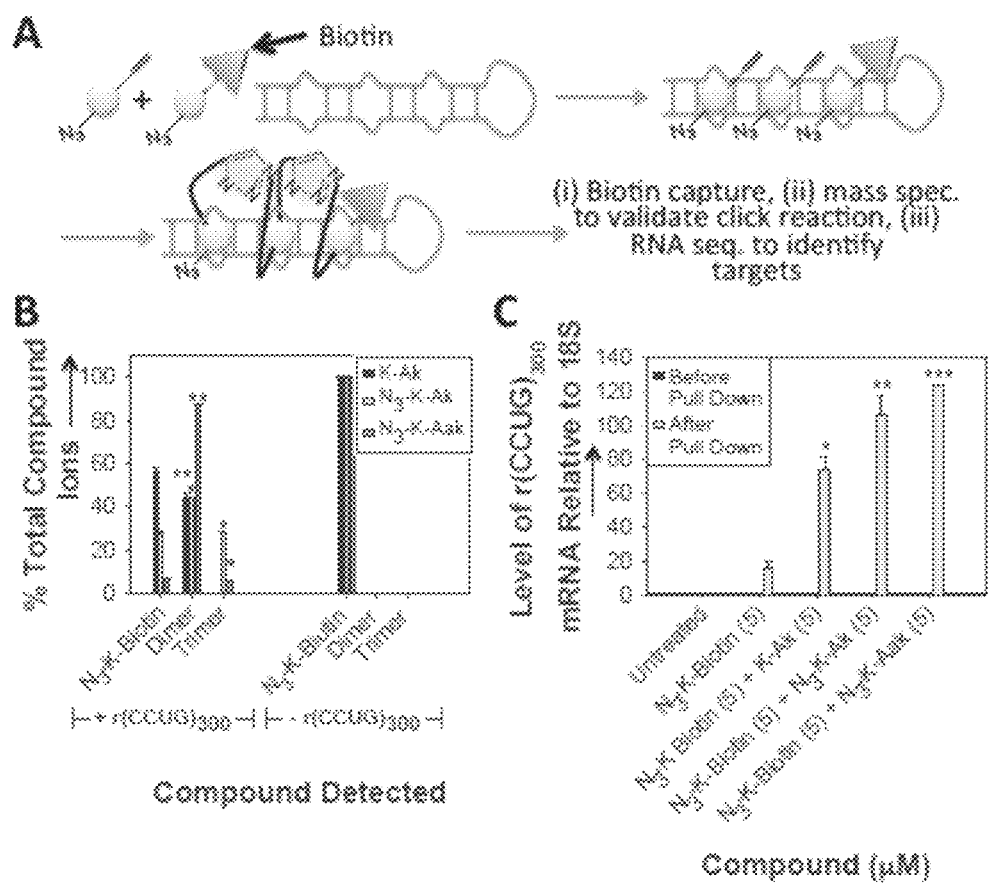
FIG. 2. Identifying the extent of in cellulo click reactions and the targets of clickable small molecules. A, Schematic of ChemReactBIP, an approach to identify the cellular targets of small molecules. Studies were enabled by using a biotinylated monomer with a single $N_3$ group to participate in the click reaction, or $N_3$-K-Biotin, which allows isolation of the clicked oligomer and bound RNA targets by passing cell lysates over streptavidin resin. B, Results of ChemReactBIP mass spectral analysis of pulled down, templated small molecule products that are only synthesized in cells expressing r(CCUG)$_{300}$. C, Results of ChemReactBIP in which the RNA targets of the clicked products were isolated and analyzed via qRT-PCR. "*" indicates $p<0.05$; "" indicates $p<0.01$; "*" indicates $p<0.001$ as determined by a two-tailed Student t-test (n=3).
Figure 3:
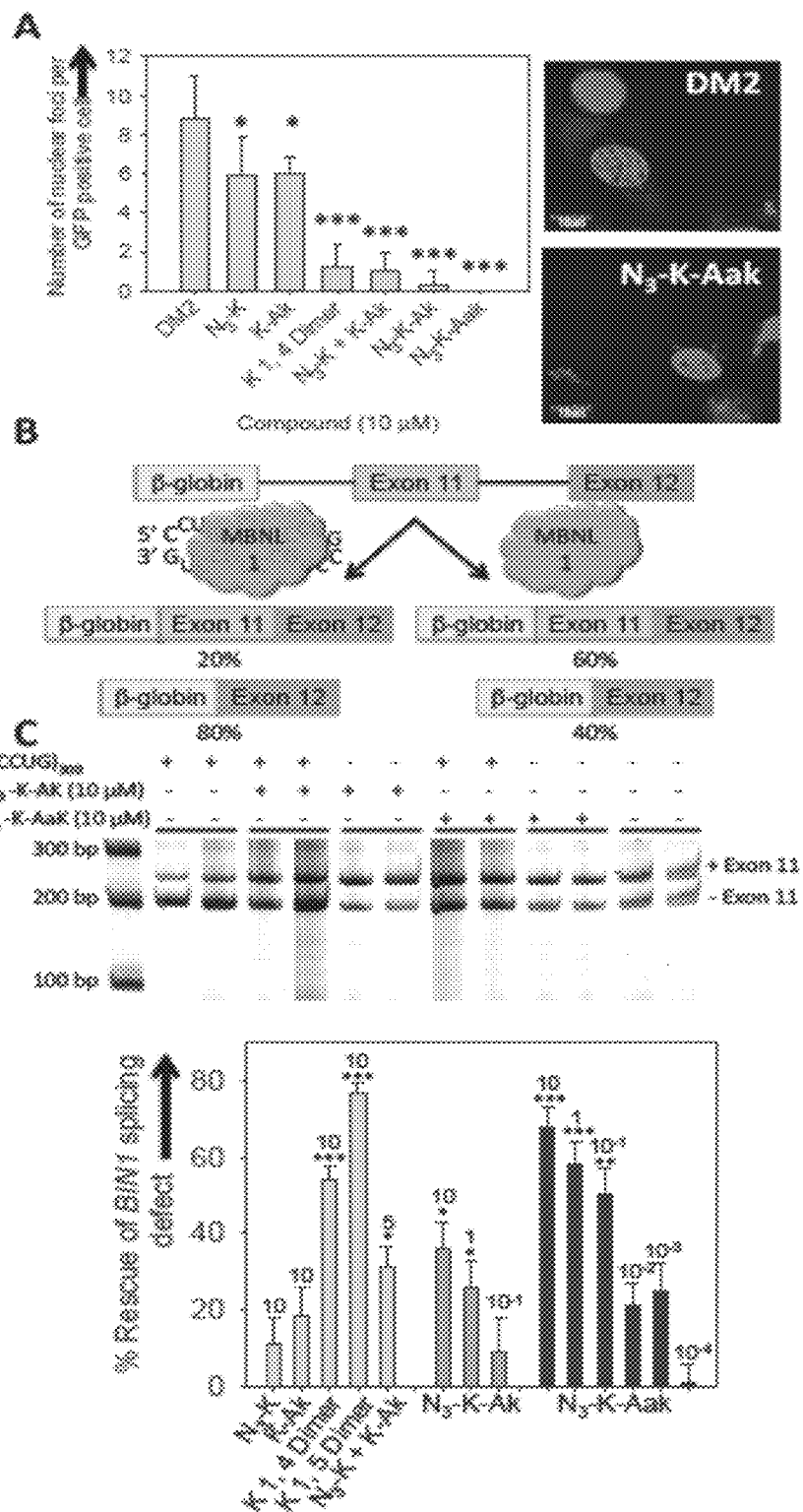
FIG. 3. Results of cellular studies evaluating the effect of in cellulo, in situ click on DM2-associated defects. A, Evaluation of click compounds for inhibiting formation of nuclear foci of r(CCUG)$_{300}$ upon treatment with various compounds. B, Schematic of the alternative splicing of bridging integrator 1 (BIN1) pre-mRNA exon 11 in healthy cells and cells that express r(CCUG)$_{300}$. C, Rescue of the BIN1 splicing defect by templated click reactions. Top, Representative gel image of BIN1 splicing products in the presence and absence of r(CCUG)$_{300}$. Bottom, quantification of BIN1 splicing patterns in treated and untreated cells. The concentration of each compound is indicated above the corresponding bar in μM. For $N_3$-K+K-Ak, 5 μM indicates the concentration of each compound. "*" indicates $p<0.05$; "" indicates $p<0.01$; "*" indicates $p<0.001$ as determined by a two-tailed Student t-test (n≥3).

Disruption of nuclear foci suggests that proteins sequestered by r(CCUG)$^{exp}$ are being freed. Thus, it is likely that the compounds also improve alternative pre-mRNA splicing defects caused by sequestration of MBNL1 in foci.[3a] We studied the ability of our compounds to improve dysregulation of the bridging integrator 1 (BIN1) pre-mRNA (FIGS. 3B-C, 13, and 14) [14] When r(CCUG)$_{300}$ is present in cells, exon 11 is skipped too frequently, resulting in an inclusion rate of ~20% in the mature mRNA. In contrast, the exon 11 inclusion rate is ~60% in unaffected cells. Interestingly, the trend observed for compound potency as measured by disruption of foci is mirrored by our results for improvement of the BIN1 alternative splicing defect (FIGS. 2 & 3). For example, pre-synthesized dimers and N$_3$-K+K-Ak improve BIN1 alternative splicing patterns to a similar extent while N$_3$-K-Ak and N$_3$-K-Aak are more potent (FIG. 3C). Notably, N$_3$-K-Aak retains the ability to improve the splicing defect at nanomolar concentrations, a >100-fold improvement over our first generation modularly assembled compound[6a] and >1000-fold better than monomers N$_3$-K and K-Ak. Importantly, compounds do not affect BIN1 splicing patterns in cells that do not express r(CCUG)$_{300}$ (FIG. 15). Collectively, our compounds that participate in a templated click reaction are the most potent non-covalent compounds that improve DM2-associated spliceopathy known to date. Furthermore, improvements in pre-mRNA splicing are due to binding r(CCUG)$_{300}$ and not to a non-specific effect.

In summary, these studies establish that an HDCR can be used to template the synthesis of an RNA inhibitor in cellulo and only in disease-affected cells. There may be numerous applications of this technology, as has been previously articulated by Sharpless and colleagues.[10] RNA repeating disorders may be a particularly attractive application. The nature of the target, which could have thousands of repeating units, could produce high yields of templated products. Moreover, many RNA gain-of-function disorders such as ALS, DM1, and DM2 cause brain dysfunction, making it important to develop low molecular weight compounds that have potential to cross the blood-brain barrier. Taken together, the click reaction could engender highly permeable low molecular weight monomers with potencies of multivalent compounds in both cellular and tissue models of disease.

This approach was also applied to target the causative agent of DM1 (r(CUG)$^{exp}$), which has a similar disease mechanism as observed for DM2. DM1 is caused by r(CUG)$^{exp}$ located in the 3' UTR of DMPK, which also binds to and sequesters proteins that are involved in RNA biogenesis such as MBNL1 (FIG. 21).

We previously described a dimeric compound that contain a H RNA binding module displayed on a N-methyl peptide backbone, 2H-K4NMe, that binds r(CUG)$^{exp}$ and ameliorates DM1 dysfunction in cells and a DM1 mouse model. (FIG. 22; Rzuczek S G, Gao Y, Tang Z Z, Thornton C A, Kodadek T, Disney M D. ACS Chem Biol. 2013 Oct. 18; 8(10):2312-21). After exposure to rat microsomes for 2 h, only 35% of the compound was intact. Inspection of the compound suggested that the amide bond could be a metabolic liability; thus the amide was replaced with an N-methyl amide to produce 2H-K4NMeS, which was found to be stable to rat microsomes (FIG. 22).

This stable compound, 2H-K4NMeS, was tested for improving pre-mRNA splicing defects in DM1 patient-derived fibroblasts (see: Konieczny, P.; Stepniak-Konieczna, E.; Sobczak, K. Nucleic Acids Research 2014, 42, 10873.) and found to rescue >50% of the defect at concentrations greater than 100 nM (FIG. 23). 2H-K4NMeS (metabolically stable) and 2H-K4NMe (metabolically unstable) were next tested for improving pre-mRNA splicing defects in the HSA$^{LR}$ mouse model (see: Mankodi, A., Logigian, E., Callahan, L., McClain, C., White, R., Henderson, D., Krym, M., and Thornton, C. A. (2000) Myotonic dystrophy in transgenic mice expressing an expanded CUG repeat. Science 289, 1769-1773.). Results show that the 2H-K4NMeS is >7-fold more potent at improving a Clcn1 pre-mRNA splicing defect in the mouse model compared to 2H-K4NMe (FIG. 23).

Given the good activity of 2H-K4NMeS, the cellular targets of this molecule were probed by using chemical cross-linking and isolation by pull down (Chem-CLIP). In this approach, a reactive derivative of the parent compound 2H-K4NMeS-CA-Biotin that contains a reactive module (CA) and a purification tag (Biotin). The structure of the Chem-CLIP probe is shown in FIG. 24A. Testing of this compounds for in vitro reaction with RNA targets was completed and showed that the compound most effectively reacted with r(CUG)$_{109}$ (FIG. 24B).

Application of this compound to DM1 patient-derived fibroblasts was next completed to profile the RNA targets of the compound. After compound exposure and cell lysis, the total RNA was captured onto streptavidin resin. The bound, biotinylated materials were released from the resin and quantified by using qRT-PCR. These studies showed that DMPK mRNA, which contained r(CUG)$^{exp}$ in the 3'UTR is enriched significantly in the pull down (FIG. 24C). Addition of unreactive and excess of 2H-K4NMeS over 2H-K4NMeS-CA-Biotin and repeating Chem-CLIP—this experiment is termed competitive chemical cross-linking and isolation by pull down (C-Chem-CLIP_shows that the unreactive compound depletes the amount of DMPK in the pulled down fraction (FIG. 24D).

Next, Chemical Crosslinking and Isolation by Pull Down to Map Ligand Binding Sites (Chem-CLIP-Map) was performed to identify the binding site for 2H-K4NMeS-CA-Biotin in the DMPK mRNA (Yang, W.-Y., Wilson, H. D., Velagapudi, S. P., and Disney, M. D. (2015) Inhibition of non-ATG translational events in cells via covalent small molecules targeting RNA, J. Am. Chem. Soc. 137, 5336-5345.). This was completed by precisely cleaving the DMPK mRNA pulled down by 2H-K4NMeS-CA-Biotin with antisense oligonucleotides and RNase H. The cleaved fragments that were biotinylated by reaction with 2H-K4NMeS-CA-Biotin were captured onto streptavidin resin and purified. Quantification showed that the 3' UTR r(CUG)$^{exp}$-containing fragment of the DMPK mRNA was significantly enriched in the pulled-down fraction, validating the expected binding site of the compound.

Next, a derivative of 2H-K4NMeS was synthesized such that it could be used in a cellular click reaction to synthesize dimeric compounds targeting r(CUG)$^{exp}$ on-site, by analogy to the experiments presented herein for the DM2 RNA. A series of compounds were synthesized in which: (i) a single azide was displayed (N$_3$-2H-K4NMeS); and (ii) activated alkynes were displayed at varying distances from the N-methyl backbone (2H-K4NMeS-Activated Alkynes). These structures are shown in FIG. 26.

Initially, we studied if r(CUG)$_{12}$ could catalyze oligomerization of the structures shown in FIG. 26 via an HDCR between two compounds bound to adjacent sites. Results show that 2H-K4NMeS-Aak provided the best alkyne spacer unit to react with N$_3$-2H-K4NMeS in the presence of r(CUG)$_{12}$ (FIG. 27A). The optimal compounds were then tested for their union being catalyzed by using other nucleic acids (FIG. 27B) and it was shown that only r(CUG)$_{12}$ provided significant reaction yield.

Next, the lessons in spacing developed above were used to design a small molecule that had reactive azide and alkyne moieties in a single small molecule. The compound N$_3$-2H-K4NMeS-Aak was thus synthesized (FIG. 28). This compound should be capable of forming larger oligomers in the presence of r(CUG)$^{exp}$ than a mixture of the corresponding azide and alkyne tagged compounds.

The extent of N$_3$-2H-K4NMeS-Aak oligomerization in patient-derived cells was tested by using ChemReactBIP. In this approach, a version of N$_3$-2H-K4NMeS-Aak was synthesized (Biotin-N$_3$-2H-K4NMeS-Aak, FIG. 29A) that allowed for both starting materials and products of a reaction to be purified from cells via streptavidin capture (FIG. 29B). These studies showed that the oligomeric product was only observed in DM1-derived fibroblasts (FIG. 29C) Since the above data showed that on-site drug synthesis for DM1 was viable (FIG. 29), the biological activity of this compound (N$_3$-2H-K4NMeS-Aak) was assessed. Addition of the N$_3$-2H-K4NMeS-Aak improved DM1-associated pre-mRNA splicing defects by >50% at 10 nM dosage, much more potent than treatment with N$_3$-2H-K4NMeS alone or co-treatment of N$_3$-2H-K4NMeS and 2H-K4NMeS-Aak (FIG. 30A). Next, the effects of the compounds on RNA foci were measured, showing that far fewer foci are observed when the clickable compound N$_3$-2H-K4NMeS-Aak is added to cells (FIG. 30B). Lastly, r(CUG)$^{exp}$-containing DMPK mRNA is translated at much lower levels as it is retained in the nucleus (Childs-Disney, J. L.; Hoskins, J.; Rzuczek, S. G.; Thornton, C. A.; Disney, M. D. ACS Chemical Biology 2012.). Thus, N$_3$-2H-K4NMeS-Aak may alter in the subcellular localization of DMPK by alleviating sequestration in foci and stimulate translation. Addition of N$_3$-2H-K4NMeS-Aak improved the DMPK translational defect at nanomolar concentrations in cells with long, toxic r(CUG) repeats, but has no effect on cells that did not have pathogenic repeats.

In summary, these data show that lead optimization of compounds can be completed by varying the backbone to make them more stable. Equipping these compounds with azide and alkyne moieties allows for on-site drug synthesis in DM1 patient-derived cells and affords very high potency.

Next, an approach to cleave r(CUG)$^{exp}$ was developed. It has been shown that the natural product bleomycin can cleave DNA but has also been shown to cleave RNA targets in vitro (Carter, B. J.; de Vroom, E.; Long, E. C.; van der Marel, G. A.; van Boom, J. H.; Hecht, S. M. *Proceedings of the National Academy of Sciences* 1990, 87, 9373.). Thus appendage of bleomycin to 2H-K4NMeS could equip these compounds with the ability to cleave r(CUG)$^{exp}$ in patient-derived cells. Synthesis of 2H-K4NMeS-Bleomcyin A5 was thus completed (FIG. 31A). Application of this compound to DM1 patient-derived fibroblasts results in reduced levels of DMPK mRNA as assessed by qRT-PCR but has no effect on DMPK mRNA levels in healthy fibroblasts (FIG. 31B). To further test the ability of the compound to selectively cleave DMPK mRNA, 4-fold excess of 2H-K4NMeS vs. 2H-K4NMeS-Bleomcyin A5 was added to cells. As expected, the unreactive compound competed with the reactive compound for binding, reducing the amount of cleavage and suggesting selectivity (FIG. 31C). These cleavage experiments also correlated with improvement of pre-mRNA splicing defects (FIG. 31D).

Fluorescent reporters were also synthesized on-site based on the RNA-catalyzed click reaction. In this approach, compounds that can undergo a click reaction are tagged with FRET pairs (FIG. 32A) such that FRET can be observed upon a click reaction. FAM (fluorescein) and TAMARA (5-Carboxytetramethylrhodamine) FRET dye pairs were used, affording FAM-2H-K4NMeS-Aak and N$_3$-2H-K4NMeS-TAMARA. Addition of the compounds showed enhancement in FRET only in the presence of r(CUG)$_{12}$. Thus, the approach allows for the on-site synthesis of FRET reporters that will have broad applicability.

DOCUMENTS CITED

[1] M. L. Yeung, Y. Bennasser, K. T. Jeang, *Curr. Med. Chem.* 2007, 14, 191-197.

[2] M. E. MacDonald, J. F. Gusella, *Curr. Opin. Neurobiol.* 1996, 6, 638-643.

[3] a) A. Mankodi, P. Teng-Umnuay, M. Krym, D. Henderson, M. Swanson, C. A. Thornton, *Ann. Neurol.* 2003, 54, 760-768; b) H. T. Orr, H. Y. Zoghbi, *Annu. Rev. Neurosci.* 2007, 30, 575-621.

[4] a) J. R. Thomas, P. J. Hergenrother, *Chem. Rev.* 2008, 108, 1171-1224; b) L. Guan, M. D. Disney, *ACS Chem. Biol.* 2012, 7, 73-86.

[5] J. R. Brouwer, R. Willemsen, B. A. Oostra, *BioEssays* 2009, 31, 71-83.

[6] a) J. L. Childs-Disney, I. Yildirim, H. Park, J. R. Lohman, L. Guan, T. Tran, P. Sarkar, G. C. Schatz, M. D. Disney, *ACS Chem. Biol.* 2014, 9, 538-550; b) M. D. Disney, L. P. Labuda, D. J. Paul, S. G. Poplawski, A. Pushechnikov, T. Tran, S. P. Velagapudi, M. Wu, J. L. Childs-Disney, *J. Am. Chem. Soc.* 2008, 130, 11185-11194.

[7] C. L. Liquori, K. Ricker, M. L. Moseley, J. F. Jacobsen, W. Kress, S. L. Naylor, J. W. Day, L. P. Ranum, *Science* 2001, 293, 864-867.

[8] B. Llano-Sotelo, E. F. Azucena, Jr., L. P. Kotra, S. Mobashery, C. S. Chow, *Chem. Biol.* 2002, 9, 455-463.

[9] J. L. Childs-Disney, J. Hoskins, S. G. Rzuczek, C. A. Thornton, M. D. Disney, *ACS Chem. Biol.* 2012, 7, 856-862.

[10] W. G. Lewis, L. G. Green, F. Grynszpan, Z. Radic, P. R. Carlier, P. Taylor, M. G. Finn, K. B. Sharpless, *Angew. Chem. Int. Ed. Engl.* 2002, 41, 1053-1057.

[11] a) A. Krasinski, Z. Radic, R. Manetsch, J. Raushel, P. Taylor, K. B. Sharpless, H. C. Kolb, *J. Am. Chem. Soc.* 2005, 127, 6686-6692; b) A. T. Poulin-Kerstien, P. B. Dervan, *J. Am. Chem. Soc.* 2003, 125, 15811-15821.

[12] M. D. Disney, J. L. Childs-Disney, *Chembiochem* 2007, 8, 649-656.

[13] M. M. Lee, J. L. Childs-Disney, A. Pushechnikov, J. M. French, K. Sobczak, C. A. Thornton, M. D. Disney, *J. Am. Chem. Soc.* 2009, 131, 17464-17472.

[14] C. Fugier, A. F. Klein, C. Hammer, S. Vassilopoulos, Y. Ivarsson, A. Toussaint, V. Tosch, A. Vignaud, A. Ferry, N. Messaddeq, Y. Kokunai, R. Tsuburaya, P. de la Grange, D. Dembele, V. Francois, G. Precigout, C. Boulade-Ladame, M. C. Hummel, A. L. de Munain, N. Sergeant, A. Laquerriere, C. Thibault, F. Deryckere, D. Auboeuf, L. Garcia, P. Zimmermann, B. Udd, B. Schoser, M. P. Takahashi, I. Nishino, G. Bassez, J. Laporte, D. Furling, N. Charlet-Berguerand, *Nat. Med.* 2011, 17, 720-725.

EXAMPLES

Methods for Computational Analysis

Figure 1:
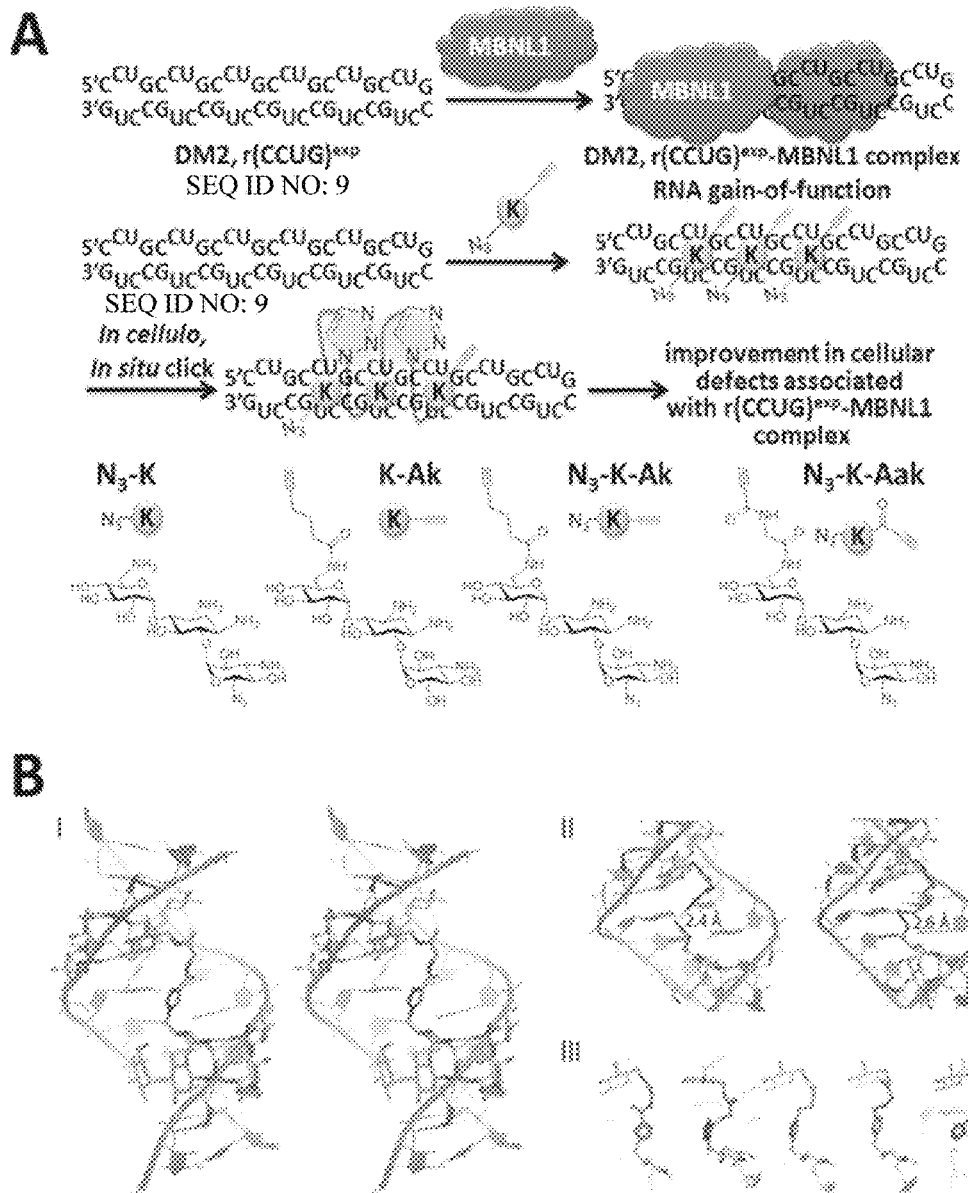
FIG. 1. In cellulo, in situ click chemistry to synthesize potent inhibitors of the RNA that causes DM2. A, DM2 is caused by a r(CCUG) repeat that binds and sequesters muscleblind-like 1 protein (MBNL1). Small molecules that contain azide and alkyne functional groups ($N_3$-K, K-Ak, $N_3$-K-Ak, and $N_3$-K-AaK) bind adjacent sites in r(CCUG)$^{exp}$ and undergo a Huisgen dipolar cycloaddition reaction. B, Molecular dynamics (MD) simulation models of clickable modules binding to a mimic of r(CCUG)$^{exp}$. BI, Conformational searching reveals close proximity between azide and alkyne groups presented by K modules bound to adjacent sites. BII, A low energy state in MD simulation of 1,4-triazole adduct from $N_3$-K and K-Aak is shown in stereoview. Hydrogen bonds between the RNA and K are shown in dashed lines. BIII, Low energy snapshot of MD simulations showing other linker models.

We previously published a model of the binding of 2K-4, two K RNA-binding modules linked by a peptoid, to an RNA containing two 5'C̲CUG/3'GUC̲C loops[1]. The peptoid was removed and the K RNA-binding modules were edited to include linkers: (i) the C6' of ring I in one K contained either hex-5-ynamide or N-(2-amino-2-oxoethyl) propiolamide; and (ii) an azido group was added to C6" of ring III of the other K. Conformational scanning of the linkers was conducted to check whether the reactive termini of the two Ks come within close proximity of each other. The exhaustive non-redundant conformational scanning was conducted with MacroModel (Schrödinger, LLC) using the OPLS_2005 force field[2]. The result showed multiple conformations bring the two reactive groups in close proximity with the shortest ethynyl C to azido N distances of 2.61 Å and 2.37 Å in hex-5-ynamide and N-(2-amino-2-oxoethyl) propiolamide linkers, respectively (FIG. 1, BI).

The linker sets with the closest reactive groups in each structure were used to generate models for cycloaddition end products, K 1,4-dimer and K 1,5-dimer. The K 1,5-dimer for each linker combination (hex-5-ynamide+N$_3$ or N-(2-amino-2-oxoethyl)propiolamide+N$_3$) has one conformation. The K 1,4-dimer for each linker combination showed two major conformations were possible, either the triazole ring C$_5$H pointing toward solvent (C$_5$H-out) or toward RNA major groove (C$_5$H-in). A total of six models were thus produced (FIG. 1, BII & BIII). Each structure was briefly energy minimized followed by molecular dynamics (MD) simulations in order to observe the stability of the complex and the effects of the linkers on the bound Ks. MD simulations were conducted using Desmond[3] with the OPLS_2005 force field[2]. Each model structure was solvated in an orthorhombic box with TIP3 water and 150 mM NaCl, which buffers 10 Å in each direction. Additional ions were added to neutralize the system. Before MD simulations, the systems were pre-equilibrated using the NPT relaxation protocol, which consists of restrained/unrestrained minimizations and short simulations with isothermal and isobaric ensemble. The 10 ns MD simulations were performed at constant temperature (300K) and pressure (1.01325 bar). Positional restraints were applied to the RNA throughout the simulation. Short- and long-range Coulombic interactions were set to Cutoff method with 9 Å radius (short) and smooth particle mesh Ewald tolerance method with a tolerance o 1×10⁻⁹ (long). Analyses of the simulations were completed with Maestro graphics interface.

No significant fluctuations of system volume, pressure, temperature and potential energy were observed. Total energies of the systems were stabilized after about ~4-6 ns in most of the simulations except in two cases where the value continuously increased. However, the slopes were less than 0.05 kcal/ps during the simulation periods. Hydrogen bonds between K moieties and the RNA were preserved throughout the simulations. Figures were prepared using PyMol (Schrödinger, LLC).

Methods for Compound Synthesis & Compound Characterization

Abbreviations.

DIC, N,N'-Diisopropylcarbodiimide; DIEA, N,N-Diisopropylethylamine; DMF, N,N-dimethylformamide; HPLC, high performance liquid chromatography; HRMS, high resolution mass spectrometry; LC-MS, liquid chromatography-mass spectrometry; MeOH, methanol; MALDI ToF/ToF, matrix-assisted laser desorption/ionization time of flight/time of flight; MS, mass spectrometry; NBD, 7-nitrobenz-2-oxa-1,3-diazole-4-yl; TFA, trifluoroacetic acid Synthesis.

Fmoc-Rink amide resin (0.59 mmol/g) was purchased from Advanced ChemTech. N, N-dimethylformamide (DMF, anhydrous) was purchased from EMD and used without further purification. Piperidine, trifluoroacetic acid (TFA), N, N-diisopropylethyl amine (DIEA), and 2-bromoacetic acid were purchased from Sigma Aldrich. N, N'-diisopropylcarbodiimide (DIC), 1-1-hydroxy-7-azabenzotriazole (HOAt), and Fmoc-β-alanine were purchased from Advanced ChemTech. Fmoc-N-methyl-L-alanine and N-(4-aminobutyl)-N-methyl carbamic acid tert-butyl ester were purchased from Combi-Blocks. N-(4-aminoethyl)-N-methyl carbamic acid tert-butyl ester was purchased from Oakwood Products. Chlorambucil was purchased from MP Biomedicals. Bleomycin A5 was purchased from LKT Laboratories. Hoechst carboxylate (Pushechnikov A, Lee M M, Childs-Disney J L, Sobczak K, French J M, Thornton C A, Disney M D. *J Am Chem Soc.* 2009 Jul. 22; 131(28):9767-79), 2H-K4NMe (Rzuczek S G, Gao Y, Tang Z Z, Thornton C A, Kodadek T, Disney M D. *ACS Chem Biol.* 2013 Oct. 18; 8(10):2312-21), and biotin amine (Yamada, M.; Harada, K.; Maeda, Y.; Hasegawa, T. *New Journal of Chemistry* 2013, 37, 3762.) were synthesized as reported previously. N-methyl peptides were synthesized using a Biotage Initiator+ SP Wave microwave.

Compound Purification and Analysis.

Preparative HPLC was performed using a Waters 1525 Binary HPLC pump equipped with a Waters 2487 dual absorbance detector system and a Waters Sunfire C18 OBD 5 μm 19×150 mm column. Absorbance was monitored at 280 and 220 nm. A gradient of 0-100% MeOH in $H_2O$ with 0.1% TFA over 60 min was used for compound purification. Analytical HPLC was performed using a Waters Symmetry C18 5 μm 4.6×150 mm column. All compounds evaluated had ≥95% purity as determined by analytical HPLC. Mass spectrometry was performed with an Applied Biosystems MALDI ToF/ToF Analyzer 4800 Plus using an α-hydroxycinnamic acid matrix. All microwave reactions were performed using a Biotage initiator+ SP Wave microwave. High resolution mass spectral analysis was performed by the University of Illinois Urbana-Champaign School of Chemical Sciences Mass Spectrometry Center.

Synthesis of K 1, 4 Dimer. See FIG. 16.

$N_3$-K (50 mg, 50 μmol) and K-Ak (45 mg, 50 μmol) were dissolved in a 1:1 mixture of DMF and water (3 mL) and treated with polytriazole Cu(I) catalyst (10 mg, 16 μmol)[4] and $Et_3N$ (500 μL, 3.6 mmol). The reaction mixture was microwaved at 100° C. for 2.5 h, after which the reaction mixture was concentrated and purified by reverse phase HPLC as described above. Yield: 11%; 6.2 mg of white solid as a TFA salt. $H^1$NMR (700 mHz, $D_2O$, TSP): δ 4.31 (m, 2H), 3.99 (m, 2H), 3.92 (m, 2H), 3.75 (m, 9H), 3.54 (m, 7H), 3.41 (t, 2H, J=10 Hz), 3.31 (m, 2H), 3.24 (dd, 2H, J=7, 13), 2.73 (t, 2H, J=8 Hz), 2.52 (m, 2H), 2.34 (t, 2H, J=8 Hz), 1.92 (m, 4H), 1.25 (m, 4H); $C^{13}$NMR (175 mHz, $D_2O$, TSP): —6=179.8, 166.2, 166.0, 165.8, 165.6, 150.3, 132.1, 127.8, 121.8, 120.1, 118.4, 116.8, 103.7, 103.5, 101.2, 100.3, 86.6, 82.4, 81.7, 76.0, 75.7, 75.0, 74.9, 74.1, 74.0, 73.7, 73.6, 72.9, 72.5, 71.6, 71.1, 70.9, 69.5, 68.2, 62.6, 57.9, 53.1, 52.9, 52.6, 51.2, 50.9, 43.2, 42.1, 38.0, 31.2, 30.7, 30.6, 28.1, 27.0 ppm; HRMS (ESI) m/z calculated for $C_{42}H_{79}N_{12}O_{11}$ (M+H) 1087.5483; found 1087.5453.

Synthesis of K 1,5 Dimer. See FIG. 17.

Boc-$N_3$-K (20 mg, 20 μmol) and Boc-K-Ak (23 mg, 20 μmol) were dissolved in toluene (2 mL) and placed under argon. The sample was treated with pentamethylcyclopentadienylbis(triphenylphosphine)ruthenium(II) chloride (6 mg, 0.8 μmol) and microwaved at 130° C. for 3 h. The reaction mixture was then filtered and concentrated. The residue was treated with a 1:1 mixture of TFA in $CH_2Cl_2$ at 0° C. for 2 h. The reaction mixture was concentrated and purified by reverse phase HPLC as described above. Yield: 0.5%; 1 mg of white solid as a TFA salt. $^1$HNMR (700 mHz, $D_2O$, TSP): δ 7.66 (s, 1H), 3.52 (m, 32H), 2.53 (m, 2H), 2.37 (m, 2H), 2.24 (m, 2H), 1.98, (m, 2H), 1.87 (m, 4H), 1.34 (m, 4H); $^{13}$CNMR (175 mHz, $D_2O$, TSP): δ=179.8, 166.2, 166.0, 165.8, 165.6, 121.8, 120.1, 118.4, 116.8, 103.5, 103.4, 101.0, 98.4, 87.6, 86.5, 82.3, 81.2, 76.0, 75.9, 75.8, 75.7, 75.1, 74.1, 74.0, 73.6, 73.0, 72.9, 71.7, 71.6, 71.1, 68.2, 62.6, 57.9, 57.3, 52.6, 51.1, 51.0, 50.8, 50.5, 45.5, 43.2, 42.1, 37.5. 30.9, 30.6, 27.0, 20.6, 19.9, 19.2, 15.1 ppm; HRMS (ESI) m/z calculated for $C_{42}H_{78}N_{11}O_{22}$ (M+H) 1088.5323; found 1088.5316.

Synthesis of $N_3$-K-Ak. See FIG. 18.

$N_3$-K (25 mg, 49 μmol) was dissolved in a 1:1 mixture of acetone and water (2 mL) and NBD-activated 6-aminohexynoic acid (6 mg, 49 μmol) was added. The reaction was stirred at room temperature overnight and then the solvent was removed in vacuo. The resulting residue was purified by reverse phase HPLC as described above. Yield: 20%; 5 mg of white solid as a TFA salt. $^1$HNMR (700 mHz, $D_2O$, TSP): δ=4.05 (m, 1H), 3.91 (m, 4H), 3.78 (t, 2H, J=9), 3.74 (dd, 2H, J=4, 14), 3.70 (m, 4H), 3.66 (m, 2H), 3.61 (dd, 1H, J=5, 15), 3.55 (dd, 2H, J=5, 12), 3.48 (m, 2H), 3.34 (t, 1H, J=10), 2.71 (s, 1H), 2.50 (d, 2H, J=12), 1.86 (m, 2H), 1.44 (t, 1H, J=7); $^{13}$CNMR (175 mHz, $D_2O$, TSP): δ=166.2, 166.0, 165.8, 165.6, 162.2, 121.8, 120.1, 119.6, 118.4, 118.0, 116.8, 103.6, 102.0, 86.5, 76.1, 75.2, 74.3, 73.9, 73.5, 71.1, 69.1, 57.7, 53.3, 52.9, 43.2, 41.6, 19.4, 19.0 ppm; HRMS (ESI) m/z calculated for $C_{24}H_{42}N_7O_{11}$ (M+H) 604.2942; found 604.2938.

Synthesis of $N_3$-K-Aak. See FIG. 19.

2-Propiolamidoacetic acid (175 mg, 1.36 mmol) was dissolved in anhydrous DMF and was treated with DIC (213 μL, 1.4 mmol), N-hydroxy-5-norborene-2,3-dicarboximide (243 mg, 1.36 mmol), and DIEA (600 μL, 3.4 mmol). The reaction mixture was stirred under argon at room temperature overnight. Next, $N_3$-K (20 mg, 40 mol) was dissolved in a 1:1 mixture of acetone and water (2 mL), and 500 μL of the NBD-activated acid was added gradually over 4 h. The solvent was then removed in vacuo, and the resulting residue was purified by reverse phase HPLC as described above. Yield: 2%, 600 µmol. $^1$HNMR (700 mHz, D$_2$O, TSP): δ=4.06 (m, 1H), 3.98 (d, 1H, J=5), 3.94 (dd, 1H, J=3, 11), 3.83 (t, 2H, J=10), 3.52 (m, 14H), 2.43 (d, 2H, J=11), 1.73 (m, 2H); $^{13}$CNMR (175 mHz, D$_2$O, TSP): δ=169.8, 166.3, 166.0, 165.8, 165.6, 131.9, 126.0, 121.8, 120.1, 118.4, 116.8, 103.4, 76.5, 75.2, 74.2, 74.2, 74.1, 73.8, 73.7, 73.4, 71.6, 71.2, 69.4, 69.2, 57.7, 53.6, 53.3, 53.2, 53.0, 51.5, 45.5, 43.2, 42.7 ppm; HRMS (ESI) m/z calculated for C$_{23}$H$_{39}$N$_8$O$_{12}$ (M+H) 619.2687; found 619.2680.

Synthesis of N$_3$-K-Biotin. See FIG. 20.

N$_3$-K (17 mg, 30 µmol) was dissolved in a 1:1 mixture of acetone and water (2 mL) and NBD-biotin (12 mg, 30 µmol) was added. The reaction was stirred at room temperature overnight and then the solvent was removed in vacuo. The resulting residue was purified by reverse phase HPLC as described above. Yield: 7%; 1.6 mg of white solid as a TFA salt. $^1$HNMR (700 mHz, D$_2$O, TSP): δ=4.60 (m 1H), 4.41 (m, 1H), 4.05 (m, 1H), 3.91 (dd, 2H, J=4, 11), 3.83 (m, 2H), 3.67 (m, 5H), 3.55 (dd, 2H, J=5, 14), 3.45 (m, 2H), 3.31 (m, 2H), 3.19 (m, 1H), 2.98 (dd, 1H, J=8, 13), 2.77 (d, 1H, J=13), 2.38 (m, 1H), 2.28 (t, 2H, J=7), 1.65 (m, 5H), 1.39 (m, 2H), 1.32 (m, 2H); $^{13}$CNMR (175 mHz, D$_2$O, TSP): δ=177.4, 177.0, 165.3, 163.3, 162.9, 162.5, 162.2, 134.3, 120.5, 117.6, 114.7, 111.8, 100.5, 98.3, 83.4, 79.9, 73.0, 72.2, 71.4, 71.2, 71.1, 70.1, 68.1, 66.2, 62.0, 60.2, 55.4, 54.7, 51.1, 50.4, 49.8, 48.1, 44.3, 42.6, 39.6, 39.1, 35.3, 27.8, 27.6, 25.1 ppm; HRMS (ESI) m/z calculated for C$_{28}$H$_{50}$N$_9$O$_{12}$S (M+H) 736.3300; found 736.3297.

Synthesis of Small Molecule Dimers.

Synthesis of 2H-K4NMeS. See FIG. 33.

Rink amide resin (500 mg, 0.3 mmol) was swollen in DMF at room temperature for 10 min and then deprotected with a solution of 20% piperidine in DMF (5 mL, 2×20 min). The resin was washed with DMF (3×5 mL) and reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of N-(4-aminobutyl)-N-methyl carbamic acid tert-butyl ester (121 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL). Then a solution of Fmoc-N-methyl-L-alanine (264 mg, 0.81 mmol), DIC (250 µL, 1.6 mmol), HOAt (110 mg, 0.81 mmol), and DIEA (141 µL, 0.81 mmol) in DMF (4 mL) was added and the reaction was heated via microwave to 75° C. for 30 min. The resin was washed with DMF and the Fmoc was removed with 20% piperidine/DMF (2×10 min). This cycle was repeated a total of four times. Next the resin was washed with DMF and DCM and then treated with 30% TFA/DCM (5 mL) for 10 min. The solution was concentrated in vacuo and azeotroped with toluene three times. The resulting pale yellow oil was treated with a solution of Hoechst carboxylate (80 mg, 0.16 mmol), HOAt (22 mg, 0.16 mmol), DIC (25 µL, 0.16 mmol) and DIEA (100 µL) in DMF (2 mL) and heated via microwave to 75° C. for 1.5 h. The solution was then concentrated in vacuo and purified using reverse phase HPLC with 20-100% MeOH/H$_2$O+ 0.1% (v/v) TFA over 1 h. Isolated 640 nanomoles of 2H-K4NMeS; 0.2%. 2H-K4NMeS (C$_{81}$H$_{101}$N$_{19}$O$_9$) MS calculated (M+H) 1484.81, MS found 1484.93 (M+H); t$_R$=32 min.

Synthesis of 2H-K4NMeS Intermediate for Functionalization.

Rink amide resin (500 mg, 0.3 mmol) was swollen in DMF at room temperature for 10 min and then deprotected with a solution of 20% piperidine in DMF (5 mL, 2×20 min). The resin was washed with DMF (3×5 mL) and reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of N-(4-aminobutyl)-N-methyl carbamic acid tert-butyl ester (121 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL). Then a solution of Fmoc-N-methyl-L-alanine (264 mg, 0.81 mmol), DIC (250 µL, 1.6 mmol), HOAt (110 mg, 0.81 mmol), and DIEA (141 µL, 0.81 mmol) in DMF (4 mL) was added and the reaction was heated via microwave to 75° C. for 30 min. The resin was washed with DMF and the Fmoc was removed with 20% piperidine/DMF (2×10 min). This cycle was repeated a total of three times. The resin was washed with DMF (3×5 mL) and reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of N-(4-aminoethyl)-N-methyl carbamic acid tert-butyl ester (105 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL).

Synthesis of 2H-K4NMeS-CA-Biotin. See FIG. 34.

The 2H-K4NMeS intermediate resin prepared above was reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of biotin amine (200 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL). Then a solution of Fmoc-β-alanine (252 mg, 0.81 mmol), DIC (250 µL, 1.6 mmol), HOAt (110 mg, 0.81 mmol), and DIEA (141 µL, 0.81 mmol) in DMF (4 mL) was added and the reaction was heated via microwave to 75° C. for 30 min. The resin was washed with DMF and DCM and then treated with 30% TFA/DCM (5 mL) for 10 min. The solution was concentrated in vacuo and azeotroped with toluene three times. The resulting pale yellow oil was treated with a solution of Hoechst carboxylate (80 mg, 0.16 mmol), HOAt (22 mg, 0.16 mmol), DIC (25 µL, 0.16 mmol) and DIEA (100 µL) in DMF (2 mL) and heated via microwave to 75° C. for 1.5 h. The solution was then concentrated in vacuo and purified using reverse phase HPLC with 20-100% MeOH/H$_2$O+0.1% (v/v) TFA over 1 h. Then the Fmoc was removed with 20% piperidine/DMF (1×10 min) and then concentrated in vacuo. Isolated 143 nanomoles (0.05%) of free amine dimer which was treated with a solution of chlorambucil (1 mg, 3 µmoles), DIC (25 µL, 0.16 mmol) and DIEA (25 µL) in DMF (200 µL) at room temperature for 3 h. The solution was then concentrated in vacuo and purified using reverse phase HPLC with 20-100% MeOH/H$_2$O+0.1% (v/v) TFA over 1 h. Isolated 119 nanomoles of 2H-K4NMeS-CA-Biotin; 0.04%. 2H-K4NMeS-CA-Biotin (C$_{113}$H$_{149}$Cl$_2$N$_{26}$O$_{14}$S) MS calculated 2196.08 (M+H), MS found 2195.96 (M+H); t$_R$=30 min.

Synthesis of 2NAc-K4NMeS-CA-Biotin. See FIG. 35.

Synthesized as described above for 2H-K4NMeS-CA-Biotin but instead of coupling with Hoechst carboxylate the peptide was treated with a 1:1 solution of acetic anhydride and DIEA (400 µL total volume) at room temperature for 1 h. Isolated 800 nanomoles of 2NAc-K4NMeS; 0.3%). 2NAc-K4NMeS ($C_{59}H_{96}Cl_2N_{14}O_{12}SNa$) MS calculated 1317.63 (M+Na), MS found 1317.28 (M+Na); $t_R$=18 min.

Synthesis of 2H-K4NMeS-Bleomycin A5. See FIG. 36.

The 2H-K4NMeS intermediate resin prepared above was reacted with a solution of 6-(Fmoc-amino)hexanoic acid (286 mg, 0.81 mmol) DIC (250 µL, 1.6 mmol), HOAt (110 mg, 0.81 mmol), and DIEA (141 µL, 0.81 mmol) in DMF (4 mL) was added and the reaction was heated via microwave to 75° C. for 30 min. The resin was washed with DMF and DCM and then treated with 30% TFA/DCM (5 mL) for 10 min. The solution was concentrated in vacuo and azeotroped with toluene three times. The resulting pale yellow oil was treated with a solution of Hoechst carboxylate (80 mg, 0.16 mmol), HOAt (22 mg, 0.16 mmol), DIC (25 µL, 0.16 mmol) and DIEA (100 µL) in DMF (2 mL) and heated via microwave to 75° C. for 1.5 h. The solution was then concentrated in vacuo and purified using reverse phase HPLC with 20-100% MeOH/$H_2O$+0.1% (v/v) TFA over 1 h. Then the Fmoc was removed with 20% piperidine/DMF (1×10 min) and then concentrated in vacuo. Isolated 450 nmol (0.2%) of free amine dimer which was treated with a solution of N,N'-disuccinimidyl carbonate (450 nmol, LKT Labs) and DIEA (10 µL) in dry DMF (50 µL). The reaction stirred at room temperature and additional, N,N'-disuccinimidyl carbonate was added periodically until 80-90% of the starting material was consumed. Then a solution of bleomycin A5-copper complex (450 nmol) in dry DMF was added and the reaction stirred at room temperature overnight. The solution was then concentrated in vacuo and purified using reverse phase HPLC by first using 0.1 mM EDTA in water (pH 6.3) for 15 min and then 0-100% $CH_3CN/H_2O$+0.1% TFA over 1 h. Isolated 52 nanomoles of 2H-K4NMeS-Bleomycin A5 (0.02%). 2H-K4NMeS-Bleomycin A5 ($C_{146}H_{203}N_{40}O_{32}S_2$) MS calculated 3092.49 (M+H), MS found 3092.18 (M+H); $t_R$=35 min.

Synthesis of $N_3$-2H-K4NMeS. See FIG. 37.

Rink amide resin (200 mg, 0.12 mmol) was swollen in DMF at room temperature for 10 min and then deprotected with a solution of 20% piperidine in DMF (3 mL, 2×20 min). The resin was washed with DMF (3×3 mL) and reacted twice with a solution of 1M bromoacetic acid (2 mL) in DMF and DIC (125 µL, 0.8 mmol) via microwave irradiation (3×15 s) using a 700 W microwave set to 10% power. The resin was washed with DMF (3×3 mL) and reacted with a solution of 3-azidopropylamine (60 mg, 0.6 mmol) in DMF (2 mL) via microwave irradiation (3×15 s) using a 700 W microwave set to 10% power. The resin was shaken with this solution at room temperature for 1 h and then washed with DMF (3×3 mL). The resin was again reacted twice with a solution of 1M bromoacetic acid (2 mL) in DMF and DIC (125 µL, 0.8 mmol) via microwave irradiation (3×15 s) using a 700 W microwave set to 10% power. The resin was washed with DMF (3×3 mL) and reacted with a solution of N-(4-aminobutyl)-N-methyl carbamic acid tert-butyl ester (60 mg, 0.3 mmol) in DMF (2 mL) via microwave irradiation (3×15 s) using a 700 W microwave set to 10% power. The resin was shaken with this solution at room temperature for 1 h and then washed with DMF (3×3 mL). Then a solution of Fmoc-N-methyl-L-alanine (132 mg, 0.4 mmol), DIC (125 µL, 0.8 mmol), HOAt (55 mg, 0.4 mmol), and DIEA (70 µL, 0.4 mmol) in DMF (2 mL) was added and the reaction was heated via microwave to 75° C. for 30 min. The resin was washed with DMF and the Fmoc was removed with 20% piperidine/DMF (2×10 min). This cycle was repeated a total of four times. Next the resin was washed with DMF and DCM and then treated with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/$H_2O$+0.1% (v/v) TFA over 1 h. Isolated 640 nanomoles of $N_3$-2H-K4NMeS; 0.5%. $N_3$-2H-K4NMeS ($C_{85}H_{108}N_{23}O_{10}$) MS calculated (M+H) 1610.87, MS found 1610.96 (M+H); $t_R$=34 min.

Synthesis of $N_3$-2H-K4NMeS Biotin. See FIG. 38.

Rink amide resin (500 mg, 0.3 mmol) was swollen in DMF at room temperature for 10 min and then deprotected with a solution of 20% piperidine in DMF (3 mL, 2×20 min). The resin was washed with DMF (3×5 mL) and reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of 3-azidopropylamine (120 mg, 1.2 mmol) in DMF (5 mL) via microwave irradiation (3×15 s) using a 700 W microwave set to 10% power. The resin was shaken with this solution at room temperature for 1 h and then washed with DMF (3×5 mL). The resin was again reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of N-(4-aminobutyl)-N-methyl carbamic acid tert-butyl ester (121 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL). Then a solution of Fmoc-N-methyl-L-alanine (264 mg, 0.81 mmol), DIC (250 µL, 1.6 mmol), HOAt (110 mg, 0.81 mmol), and DIEA (140 µL, 0.81 mmol) in DMF (5 mL) was added and the reaction was heated via microwave to 75° C. for 30 min. The resin was washed with DMF and the Fmoc was removed with 20% piperidine/DMF (2×10 min). This cycle was repeated a total of three times. The resin was washed with DMF (3×5 mL) and reacted twice with a solution of 1M bromoacetic acid (4 mL) in DMF and DIC (250 µL, 1.6 mmol) via microwave irradiation (3×15 s) using a 700 W microwave set to 10% power. The resin was washed with DMF (3×5 mL) and reacted with a solution of N-(4-aminoethyl)-N-methyl carbamic acid tert-butyl ester (105 mg, 0.6 mmol) in DMF (4 mL) via microwave irradiation (3×15 s) using a 700 W microwave set to 10% power. The resin was shaken with this solution at room temperature for 1 h and then washed with DMF (3×5 mL). Next the resin was treated with a solution of D-biotin (195 mg, 0.81 mmol), DIC (250 µL, 1.6 mmol), HOAt (110 mg, 0.81 mmol), and DIEA (140 µL, 0.81 mmol) in DMF (5 mL) was added and the reaction was heated via microwave to 75° C. for 30 min. Next the resin was washed with DMF and DCM and then treated with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/$H_2O$+0.1% (v/v) TFA over 1 h. Isolated 640 nanomoles of $N_3$-2H-K4NMeS-Biotin; 0.2%. $N_3$-2H-K4NMeS-Biotin ($C_{97}H_{127}N_{26}O_{12}S$) MS calculated (M+H) 1879.98, MS found 1879.87 (M+H); $t_R$=31 min.

Synthesis of 2H-K4NMeS Activated Alkynes. See FIG. 39.

For each alkyne derivative 300 mg of resin (0.18 mmol) with 2H-K4NMeS intermediate was treated with a solution of N-Fmoc carboxylate linker (0.6 mmol), DIC (125 µL, 0.8 mmol), HOAt (72 mg, 0.6 mmol), and DIEA (80 µL, 0.6 mmol) in DMF (2 mL) was added and the reaction was heated via microwave to 75° C. for 30 min. The resin was washed with DMF and the Fmoc was removed with 20% piperidine/DMF (2×10 min). Then the resin was washed with DMF and then suspended in 2 mL of DMF with DIEA (80 µL, 0.6 mmol). The suspension was flushed with argon and cooled to 0° C. Then DIC (125 µL, 0.8 mmol) was added followed by slow addition of a solution of propiolic acid (37 µL, 0.6 mmol) in DMF (500 µL). The reaction stirred at low temperature for 1 h and then was washed with DMF and DCM. The resin was then treated with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/$H_2O$+0.1% (v/v) TFA over 1 h. 2H-K4NMeS Propiolate (n=0) 900 nmoles (0.5%) ($C_{85}H_{105}N_{20}O_{10}$) MS calculated (M+H) 1565.83, MS found 1565.61 (M+H); $t_R$=31 min. 2H-K4NMeS Glycine (n=1) 600 nmoles (0.3%) ($C_{87}H_{108}N_{21}O_{11}$) MS calculated (M+H) 1622.854, MS found 1622.854 (M+H); $t_R$=30 min. 2H-K4NMeS β-Alanine (n=2) 750 nmoles (0.4%) ($C_{88}H_{110}N_{21}O_{11}$) MS calculated (M+H) 1636.87, MS found 1636.7 (M+H); $t_R$=31 min. 2H-K4NMeS Aminohexanoate (n=5, Aak) 4.93 moles (3%)($C_{91}H_{116}N_{21}O_{11}$) MS calculated (M+H) 1678.92, MS found 1678.7 (M+H); $t_R$=31 min. 2H-K4NMeS Aminooctanoate (n=7) 1.6 moles (0.9%) ($C_{93}H_{120}N_{21}O_{11}$) MS calculated (M+H) 1706.95, MS found 1707.0 (M+H); $t_R$=33 min. 2H-K4NMeS Aminododecanoate (n=11) 4.49 µmoles (3%) ($C_{97}H_{128}N_{21}O_{11}$) MS calculated (M+H) 1763.01, MS found 1763.2 (M+H); $t_R$=34 min.

Synthesis of $N_3$-2H-K4NMeS-Aak. See FIG. 40.

Rink amide resin (800 mg, 0.47 mmol) was swollen in DMF at room temperature for 10 min and then deprotected with a solution of 20% piperidine in DMF (5 mL, 2×20 min). The resin was washed with DMF (3×5 mL) and reacted twice with a solution of 1M bromoacetic acid (5 mL) in DMF and DIC (500 µL, 3.2 mmol) via microwave irradiation (3×15 s) using a 700 W microwave set to 10% power. The resin was washed with DMF (3×5 mL) and reacted with a solution of 3-azidopropylamine (300 mg, 3 mmol) in DMF (5 mL) via microwave irradiation (3×15 s) using a 700 W microwave set to 10% power. The resin was shaken with this solution at room temperature for 1 h and then washed with DMF (3×5 mL). The resin was again reacted twice with a solution of 1M bromoacetic acid (5 mL) in DMF and DIC (500 µL, 3.2 mmol) via microwave irradiation (3×15 s) using a 700 W microwave set to 10% power. The resin was washed with DMF (3×5 mL) and reacted with a solution of N-(4-aminobutyl)-N-methyl carbamic acid tert-butyl ester (240 mg, 1.2 mmol) in DMF (5 mL) via microwave irradiation (3×15 s) using a 700 W microwave set to 10% power. The resin was shaken with this solution at room temperature for 1 h and then washed with DMF (3×5 mL). Then a solution of Fmoc-N-methyl-L-alanine (528 mg, 1.6 mmol), DIC (500 µL, 3.2 mmol), HOAt (220 mg, 1.6 mmol), and DIEA (280 µL, 1.6 mmol) in DMF (5 mL) was added and the reaction was heated via microwave to 75° C. for 30 min. The resin was washed with DMF and the Fmoc was removed with 20% piperidine/DMF (2×10 min). This cycle was repeated a total of three times. The resin was washed with DMF (3×5 mL) and reacted twice with a solution of 1M bromoacetic acid (5 mL) in DMF and DIC (500 µL, 3.2 mmol) via microwave irradiation (3×15 s) using a 700 W microwave set to 10% power. The resin was washed with DMF (3×5 mL) and reacted with a solution of N-(4-aminoethyl)-N-methyl carbamic acid tert-butyl ester (210 mg, 1.2 mmol) in DMF (5 mL) via microwave irradiation (3×15 s) using a 700 W microwave set to 10% power. The resin was shaken with this solution at room temperature for 1 h and then washed with DMF (3×5 mL). Then the resin was treated with a solution of N-Fmoc aminohexanoic acid (565 mg, 1.6 mmol), DIC (500 µL, 3.2 mmol), HOAt (220 mg, 1.6 mmol), and DIEA (280 µL, 1.6 mmol) in DMF (5 mL) was added and the reaction was heated via microwave to 75° C. for 30 min. The resin was washed with DMF and the Fmoc was removed with 20% piperidine/DMF (2×10 min). Then the resin was washed with DMF and then suspended in 5 mL of DMF with DIEA (280 µL, 1.6 mmol). The suspension was flushed with argon and cooled to 0° C. Then DIC (500 µL, 3.2 mmol) was added followed by slow addition of a solution of propiolic acid (148 µL, 3.2 mmol) in DMF (500 µL). The reaction stirred at low temperature for 1 h and then was washed with DMF and DCM. The resin was then treated with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/$H_2O$+0.1% (v/v) TFA over 1 h. Isolated 523 nmoles (0.1%) of $N_3$-2H-K4NMeS-Aak. $N_3$-2H-K4NMeS Aak ($C_{96}H_{124}N_{25}O_{12}$) MS calculated (M+H) 1818.9861, MS found 1819.0081 (M+H); $t_R$=32 min.

Synthesis of Biotin-$N_3$-2H-K4NMeS-Aak. See FIG. 41.

Rink amide resin (250 mg, 0.15 mmol) was swollen in DMF at room temperature for 10 min and then deprotected with a solution of 20% piperidine in DMF (3 mL, 2×20 min). The resin was washed with DMF (3×3 mL) and reacted twice with a solution of 1M bromoacetic acid (2 mL) in DMF and DIC (125 µL, 0.8 mmol) via microwave irradiation (3×15 s) using a 700 W microwave set to 10% power. The resin was washed with DMF (3×3 mL) and reacted with a solution of N-[2-(D-Biotinylamino)ethyl]amine[3] (100 mg, 0.3 mmol) in DMF (3 mL) via microwave irradiation (3×15 s) using a 700 W microwave set to 10% power. The resin was shaken with this solution at room temperature for 1 h and then washed with DMF (3×5 mL). The remaining synthesis was conducted as described above for $N_3$-2H-K4NMeS-Aak. Isolated 230 nmoles of Biotin-$N_3$-2H-K4NMeS-Aak; 0.2%). Biotin-$N_3$-2H-K4NMeS-Aak ($C_{110}H_{146}N_{29}O_{15}S$) MS calculated (M+H) 2145.13, MS found 2145.07 (M+H); $t_R$=34 min.

Synthesis of $N_3$-2H-K4NMeS-TAMRA (Carboxytetramethylrhodamine). See FIG. 42.

250 mg of resin containing $N_3$-2H-K4NMeS with the Fmoc 6-amino hexanoate was cleaved from the beads with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/ H$_2$O+0.1% (v/v) TFA over 1 h. 2.95 µmoles of product was isolated and the Fmoc was removed by treating with 1 mL of 20% piperidine/DMF for 20 min at room temperature and the solution was concentrated in vacuo. The residue was again purified by reverse phase HPLC using the above conditions. A portion of the dimer (315 nmol) was coupled with 5-TAMRA (0.4 mg, 0.95 µmol) with DIC (25 µL, 0.16 mmol) in DMF (500 µL) by heating to 75° C. for 1.5 h with microwave irradiation. The reaction mixture was concentrated and purified as described above to afford 216 nmoles of N$_3$-2H-K4NMeS-TAMRA; (0.1%). N$_3$-2H-K4NMeS-TAMRA (C$_{118}$H$_{144}$N$_{27}$O$_{15}$) MS calculated (M+H) 2179.1335, MS found 2179.0483 (M+H); $t_R$=34 min.

Synthesis of FAM-2H-K4NMeS-Aak (Fluorescein). See FIG. 43.

500 mg of resin containing N$_3$-2H-K4NMeS with the Fmoc 6-amino hexanoate was cleaved from the beads with 30% TFA/DCM (5 mL) for 10 min. The solution was concentrated in vacuo and azeotroped with toluene three times. The resulting pale yellow oil was treated with a solution of Hoechst carboxylate (40 mg, 0.08 mmol), HOAt (11 mg, 0.08 mmol), DIC (25 µL, 0.16 mmol) and DIEA (50 µL) in DMF (1 mL) and heated via microwave to 75° C. for 1.5 h. The solution was then concentrated in vacuo and purified using reverse phase HPLC with 20-100% MeOH/ H$_2$O+0.1% (v/v) TFA over 1 h. The product was isolated and the Fmoc was removed by treating with 1 mL of 20% piperidine/DMF for 20 min at room temperature and the solution was concentrated in vacuo. The residue was again purified by reverse phase HPLC using the above conditions to give 8 µmoles of dimer. This was then clicked with FAM alkyne (25 mg, 6 µmol) and copper catalyst (1 mg, 1.6 µmol) by heating in DMF (2 mL) and H$_2$O (1 mL) with trimethylamine (250 µL) at 120° C. for 3 h. The reaction mixture was then concentrated and purified as described above to afford 550 nmoles of FAM dimer. This was azeotroped with toluene 3× and was then treated with a solution of propiolic acid succinimidyl ester[4] (1 mg, 6 µmol) and DIEA (25 µL) in DMF (250 µL). The reaction stirred at room temperature for 4 h and was then purified as described above. Isolated 5.9 nmoles of FAM-2H-K4NMeS-Aak; (0.002%). FAM-2H-K4NMeS-Aak (C$_{120}$H$_{139}$N$_{26}$O$_{18}$) MS calculated (M+H) 2232.0761, MS found 2232.0827 (M+H); $t_R$=35 min.

Methods for Biochemical & Cellular Assays

Evaluation of In Vitro Click by Liquid Chromatography-Mass Spectrometry (LC-MS).

In order to determine if the repeating RNA that causes DM2 serves as a template for oligomerization via HDCR, alkyne- and azide-containing compounds were incubated with an RNA containing 12 CCUG repeats. rCCUG$_{12}$ (50 µM final concentration) was folded in 1× Folding Buffer (8 mM Na$_2$HPO$_4$, pH 7.0, 185 mM NaCl, and 1 mM EDTA) at 60° C. for 5 min. After cooling to room temperature, N$_3$-K and K-Ak (500 µM final concentration each) were added and the reaction mixtures were incubated at 37° C. for 48 h. Each sample was analyzed by LC-MS using a Thermo Scientific LTQ-ETD mass spectrometer. A gradient of 0-100% acetonitrile in water plus 0.1% formic acid over 10 min was used for analysis. Total ion counts for each component were normalized to the percent ionization of each component as measured by using a control injection containing an equimolar mixture of N$_3$-K, K-Ak, and K 1,4 dimer. Control reactions using r(CUG)$_{12}$, r(AUUCU)$_{12}$, r(CAG)$_{12}$, r(CGG)$_{12}$, an RNA hairpin with a fully paired stem, and brewer's yeast tRNA (Roche) were also evaluated analogously.

Evaluation of DM2-Associated Pre-mRNA Splicing Defects in a DM2 Cell Culture Model.

In order to determine the effects of clickable compounds on DM2-associated alternative pre-mRNA splicing defects, a previously reported cell culture model was employed[5]. Briefly, C2Cl2 cells were maintained as monolayers in growth medium (1×DMEM, 10% FBS, and 1× Glutamax (Invitrogen)) at 37° C. and 5% CO$_2$. Once cells in 96-well plates reached 60-70% confluency, each sample was transfected with 200 ng of total plasmid using 1 µL of Lipofectamine 2000 (Invitrogen) according to the manufacturer's standard protocol. Equal amounts of plasmid expressing a DM2 mini-gene with 300 CCTG repeats[1] and a BIN1 reporter mini-gene were used[5]. After 5 h, the transfection cocktail was removed and replaced with differentiation medium (1×DMEM, 2% horse serum, and 1× Glutamax) containing the compound of interest. After 72 h, total RNA was harvested using a Zymo Quick RNA miniprep kit. Approximately 150 ng of total RNA was subjected to RT-PCR. The RT-PCR primers for the BIN1 mini-gene were 5'CATTCACCACATTGGTGTGC (SEQ ID NO: 1) (forward) and 5' AAGTGATCCTAGACTAGCCGCC (SEQ ID NO: 2) (reverse). RT-PCR products were separated using a denaturing 8% polyacrylamide gel run at 200 V for 90 min in 1×TBE buffer. The products were visualized by staining with SYBR Gold (Molecular Probes) and scanned using a Bio-Rad Gel Doc XR+ imaging system.

Evaluation of in Cellulo Click on the Disruption of Nuclear Foci by Fluorescence In Situ Hybridization (FISH).

FISH was utilized to determine the effects of clickable compounds on the formation of nuclear foci. C2Cl2 were sub-cultured into Mat-Tek 96-well glass bottom plates in growth medium. After the cells reached 60-70% confluency, each well was transfected with 200 ng of total plasmid using 1 µL of Lipofectamine 2000 according to the manufacturer's standard protocol. Equal amounts of plasmids expressing the DM2 mini-gene[1] and EGFP, used as a positive marker of transfection, were used. After 5 h, the transfection cocktail was removed and replaced with differentiation medium containing the compound of interest. The cells were treated with compound for 72 h followed by FISH as previously described using 1 ng/µL DY547-2'OMe-(CAGG)$_5$[6]. Cells were imaged in 1×DPBS using an Olympus FluoView 1000 confocal microscope at 100× magnification.

Identification of in Cellulo Clicked Products by Mass Spectrometry.

C2Cl2 cells were grown in T-75 dishes in growth medium. Once the cells reached 60-70% confluency, each dish was transfected with 10 µg of a plasmid expressing the DM2 mini-gene using Lipofectamine 2000 according to the manufacturer's standard protocol. After 5 h, the transfection cocktail was removed and replaced with differentiation medium containing the compounds of interest. Cells were treated with a mixture of 12.5 µM N$_3$-K and either 12.5 µM K-Ak, 12.5 µM N$_3$-K-Ak, or 12.5 µM N$_3$-K-Aak immediately after transfection. N$_3$-K was added to limit the molecular weight of the oligomeric products in order to enable detection by LC-MS. After 72 h, the cells were lysed by freezing and thawing with 10% water in acetonitrile. The thawed lysate was concentrated and re-suspended in 1 mL of 10% water in acetonitrile. Insoluble cellular debris was pelleted, and the supernatant was used for mass spectral analysis. Approximately 20 µL of each sample was analyzed by LC-MS using a Thermo Scientific LTQ-ETD mass spectrometer. A gradient of 0-100% acetonitrile in water plus 0.1% formic acid over 10 min was used for analysis. Total ion counts for each component were normalized to the percent ionization of each component in a control injection containing an equimolar mixture of $N_3$-K, K-Ak, and K 1,4 dimer.

Analysis of TargetPull-Down by qRT-PCR.

C2C12 cells were grown in T-25 flasks as monolayers in growth medium and were transfected at 60-70% confluency. Each dish was transfected with 3.4 µg of a plasmid expressing the DM2 mini-gene using Lipofectamine 2000 according to the manufacturer's standard protocol. After 5 h, the transfection cocktail was removed and replaced with differentiation medium containing the compounds of interest. Cells were treated with a mixture of 5 µM $N_3$-K-Biotin and either 5 µM K-Ak, 5 µM $N_3$-K-Ak, or 5 µM $N_3$-K-Aak immediately after transfection. $N_3$-K-Biotin was added to limit the molecular weight of the oligomeric products in order to enable detection by LC-MS. After 72 h, the cells were washed with 1×DPBS and trypsinized. The pelleted cells were lysed by treating with 500 µL of Lysis Buffer (2% Triton X-100, 2% NP40, 1/25 RNAsecure (Ambion), and 1 u/µL RQ1 DNAse (Promega))[7] for 5 min at room temperature and then incubated at 75° C. for 5 min.

Approximately 90% of the cell lysate was used for pull-down using 15 nmoles of streptavidin-agarose beads (Sigma, 15 µg/mL biotin loading). The lysate was incubated with the beads for 1 h at room temperature with shaking at 500 rpm. The solution was removed, and the beads were washed with 500 µL aliquots of 1×PBS. Bound material was released from the beads by heating at 95° C. for 5 min in 30 µL of 95% formamide containing 10 mM EDTA, pH 8.2.

Reverse transcription reactions were carried out using qScript cDNA synthesis kit by adding approximately 10% volume of either cell lysate or eluted material according to the manufacturer's protocol. Then, 30% of each cDNA sample was used for real time PCR (qPCR) analysis for each primer set. qPCR was performed on a 7900HT Fast Real-Time PCR System (Applied Biosystems) using SYBR Green I. The PCR primers for the $r(CCUG)^{exp}$-containing mRNA were 5' GTGAGTTTGGGGACCCTTGA (SEQ ID NO: 3) (forward) and 5' CACCCTGAAAACTTTGCCCC (SEQ ID NO: 4) (reverse). The PCR primers for 18S ribosomal RNA were 5' GTAACCCGTTGAACCCCATT (SEQ ID NO: 5) (forward) and 5' CCATCCAATCGGTAG-TAGCG (SEQ ID NO: 6) (reverse).

Analysis of Reaction Products Pulled Down by LC-MS.

In order to detect pulled down products, ~4 µL of eluted material was diluted in 5 volumes of water containing 0.1% TFA and analyzed by LC-MS using a Thermo Scientific LTQ-ETD mass spectrometer.

These samples were compared to pulled-down samples from compound-treated cells that did not express $r(CCUG)_{300}$. A gradient of 0-100% acetonitrile in water plus 0.1% formic acid over 10 min was used for analysis.

Evaluation of DM1 Splicing Defects in Patient Derived Fibroblasts.

Bioactivity of small molecule dimers was assessed by using DM1 patient derived fibroblasts containing 500 CTG repeats (GM03987) and healthy fibroblasts (GM07492). Cells were grown as monolayers in 12 well plates in growth medium (1×EMEM (Lonza), 10% FBS, 1× glutagro (Corning), 1×MEM non-essential amino acids (Corning) and 1× antibiotic/antimycotic (Corning)). Once cells were ~80% confluent, they were treated with growth medium containing the compound of interest (10, 1, 0.1 and 0.01 µM 2H-K4NMeS; 100, 10 and 1 nM 2H-K4NMeS-CA-Biotin; 1 µM $N_3$-2H-K4NMeS; 500 nM $N_3$-2H-K4NMeS+500 nM 2H-K4NMeS-Aminohexanoate; 1000, 10 and 0.1 nM $N_3$-2H-K4NMeS-Aak; 250, 100, and 50 nM 2H-K4NMeS-Bleomycin A5). After 48 h the cells were lysed and the total RNA was harvested using a Zymo Quick RNA miniprep kit. An on-column DNA digestion was completed per the manufacturer's recommended protocol. Approximately 150 ng of total RNA was reverse transcribed at 50° C. using 100 units of SuperScript III reverse transcriptase (Life Technologies). Then 20% of the RT reaction was subjected to PCR using GoTaq DNA polymerase (Promega). RT-PCR products were observed after 25 cycles of 95° C. for 30 s, 58° C. for 30 s, 72° C. for 1 min and a final extension at 72° C. for 1 min. The products were separated on an 2% agarose gel ran at 100 V for 1 h in 1×TAE buffer. The products were visualized by staining with ethidium bromide and scanned using a Bio-Rad Gel Doc XR+ imaging system. The RT-PCR primers for the MBNL1 were 5'GCTGCCCAATACCAGGTCAAC (SEQ ID NO: 7) (forward) and 5'TGGTGGGAGAAAT-GCTGTATG (SEQ ID NO: 8) (reverse).

Evaluation of Splicing Defects Using a DM1 Mouse Model.

All experimental procedures, mouse handling, and husbandry were completed in accordance with the Association for Assessment and Accreditation of Laboratory Animal Care. A mouse model for DM1[8], $HSA^{LR}$ in line 20b, was used. $HSA^{LR}$ mice express human skeletal actin RNA with 250 CUG repeats in the 3' UTR. Age- and gender-matched $HSA^{LR}$ mice were injected intraperitoneally with either 100 mg/kg 2H-K4NMe in water or 13.3 mg/kg 2H-K4NMeS for treatment and 0.9% NaCl for control once per day for 7 days. Mice were sacrificed one day after the last injection, and the vastus muscle was obtained. RNA was extracted from the vastus tissue, and cDNA was synthesized as previously described.

In Vitro Reaction and Pull Down of Small Molecule Dimers with RNA by Using Compounds to Target $r(CUG)^{exp}$.

Growth medium ((1×EMEM (Lonza), 10% FBS, 1× glutagro (Corning), 1×MEM non-essential amino acids (Corning) and 1× antibiotic/antimycotic (Corning) 2 mL) was heat inactivated at 95° C. for 15 min and then slowly cooled to room temperature. Then ~10,000 counts of γ $^{32}P$ labeled RNA ($rCUG_{109}$, GC-based paired RNA and tRNA) was added and folded at 95° C. for 1 min. Then 2-fold dilutions of compound (800, 400, 200 and 100 nM final concentrations) were prepared in 50 µL of RNA solution and incubated at 37° C. overnight. Then a 400 µL slurry of streptavidin-agarose beads (Sigma) were washed with 1×PBS and then resuspended in 2 mL of 1×PBS. Then 30 µL of this slurry were added to each sample and incubated at room temperature for 1 h. Then the samples were centrifuged and the supernatant was transferred to a separate tube. The beads were then washed with 1×PBST and centrifuged. The supernatant was transferred to the tube containing the unbound RNA. The total radioactive counts of bound and unbound RNA were measured by scintillation counting.

Target Identification and Pull Down by Chem-CLIP by Using the DM1 System.

Target identification of small molecule dimers was assessed using DM1 patient derived fibroblasts containing 500 CTG repeats (GM03987) and healthy fibroblasts (GM07492). Cells were grown as monolayers in 100 mm² in growth medium (1×EMEM (Lonza), 10% FBS, 1× glutagro (Corning), 1×MEM non-essential amino acids (Corning) and 1× antibiotic/antimycotic (Corning)). Once cells were ~80% confluent, they were treated with growth medium containing the compound of interest (100 nM 2H-K4NMeS- CA-Biotin). After 48 h the cells were lysed and the total RNA was harvested using Trizol reagent (Life Technologies). Approximately 10 µg of total RNA was incubated with streptavidin-agarose beads (100 µL, Sigma) for 1 h at room temperature. Then the beads were washed with 1×PBS and the bound RNA was eluted by adding 100 µL of 95% formamide, 10 mM EDTA pH 8.2 for 10 min at 60° C. The bound RNA was cleaned up using a Zymo Quick RNA miniprep kit. Approximately 100 ng of RNA was used for RT qScript cDNA synthesis kit (Quanta BioSciences). 10% of the RT reaction was used for real time PCR (qPCR) with SYBR green master mix (Life Technologies) performed on a 7900HT Fast Real-Time PCR System (Applied Biosystems). Monitored rCUG-containing mRNAs DMPK (500 repeats), SUPT20HL1 (17 repeats), CASK (16 repeats), LRP8 (11 repeats), MAP3K4 (11 repeats), SCUBE (7 repeats) and SORCS2 (7 repeats). Quantified by $\Delta\Delta C_t$ relative to GAPDH Target Identification and Pull Down by Chem-CLIP-Map.

Target identification of the binding sites of small molecule dimers was assessed using DM1 patient derived fibroblasts containing 500 CTG repeats (GM03987). Cells were grown as monolayers in 100 mm$^2$ in growth medium (1×EMEM (Lonza), 10% FBS, 1× glutagro (Corning), 1×MEM non-essential amino acids (Corning) and 1× antibiotic/antimycotic (Corning)). Once cells were ~80% confluent, they were treated with growth medium containing the compound of interest (100 nM 2H-K4NMeS-CA-Biotin). After 48 h the cells were lysed and the total RNA was harvested using Trizol reagent (Life Technologies). Approximately 6 µg of total RNA was folded with 8 µM antisense oligonucleotide in 1× RNase H buffer by heating to 95° C. for 1 min and then cooling on ice. Next 5 units of RNase H (Life Technologies) were added and the reaction was incubated at 37° C. for 1.5 h followed by heat inactivation at 65° C. for 20 min. Then the cut RNA was treated with DNase at 37° C. for 30 min and then stop buffer was added and incubated at 65° C. for 10 min. The cut RNA solution was incubated with streptavidin-agarose beads (100 µL, Sigma) for 1 h at room temperature. Then the beads were washed with 1×PBS and the bound RNA was eluted by adding 100 µL of 95% formamide, 10 mM EDTA pH 8.2 for 10 min at 60° C. The bound RNA was cleaned up using a Zymo Quick RNA miniprep kit. Approximately 150 ng of RNA was used for RT qScript cDNA synthesis kit (Quanta BioSciences). 40% of the RT reaction was used for real time PCR (qPCR) with SYBR green master mix (Life Technologies) performed on a 7900HT Fast Real-Time PCR System (Applied Biosystems). Quantified by $\Delta\Delta C_t$ relative to GAPDH.

Evaluation of In Vitro Click by Liquid Chromatography-Mass Spectrometry (LC-MS).

In order to determine if the repeating RNA that causes DM1 serves as a template for oligomerization via HDCR, 2H-K4NMeS Azide and each 2H-K4NMeS Activated Alkyne derivative were incubated with an RNA containing 12 CUG repeats. rCUG$_{12}$ (100 µM final concentration was folded in 1× Folding Buffer (8 mM Na$_2$HPO$_4$, pH 7.0, 185 mM NaCl, and 1 mM EDTA) at 60° C. for 5 min. After cooling to room temperature, azide and alkyne dimers (25 µM final concentration each) were added and the reaction mixtures were incubated at 37° C. for 24 h. Each sample was analyzed by LC-MS using a Thermo Scientific LTQ-ETD mass spectrometer. A gradient of 0-100% acetonitrile in water plus 0.1% formic acid over 10 min was used for analysis. The alkyne which gave the most reaction with r(CUG)$_{12}$, 2H-K4NMeS-Aminohexanoate Aak, was next evaluated for selectivity by analyzing the amount of dimer formed in the presence of other RNA targets. Other RNAs evaluated were r(CCUG)$_{12}$, r(CAG)$_{12}$, r(CGG)$_{12}$, and brewer's yeast tRNA (Roche) each at 100 µM final concentration.

Identification of in Cellulo Clicked Products by Mass Spectrometry Using DM1 Fibroblasts.

In order to determine if the repeating RNA that causes DM1 serves as a template for oligomerization within cells DM1 patient derived fibroblasts containing 500 CTG repeats (GM03987) and healthy fibroblasts (GM07492) were grown to 80% confluence in growth medium (1×EMEM (Lonza), 10% FBS, 1× glutagro (Corning), 1×MEM non-essential amino acids (Corning) and 1× antibiotic/antimycotic (Corning)) in T25 dishes and treated with equimolar amounts of N$_3$-2H-K4NMeS Biotin and 2H-K4NMeS-Ahx Alkyne (500 nM each) for 2 days. The cells were washed with 1×DPBS and then trypsinized. Then quenched with growth medium and spun down. Cells were washed 2× with 1×DPBS and then lysed by adding 0.25 mL of lysis buffer (2 mL total=2% Triton X 100, 2% NP40, 80 uL RNAsecure (1/25) and 50 uL DNAse) for 5 min at room temperature and then heated to 75° C. for 5 min. 200 µL of lysate was incubated with streptavidin-agarose beads (100 µL, Sigma) for 1 h at room temperature. Then the beads were washed with 1×PBST and the bound RNA was eluted by adding 20 µL of 95% formamide, 10 mM EDTA pH 8.2 for 5 min at 60° C. Approximately 4 µL of each sample was diluted in 20 µL of water plus 0.1% formic acid and analyzed by LC-MS using a Thermo Scientific LTQ-ETD mass spectrometer. A gradient of 0-100% acetonitrile in water plus 0.1% formic acid over 10 min was used for analysis.

Evaluation of Nuclear Foci Using Fluorescence In Situ Hybridization (FISH).

FISH was utilized to determine the effects of small molecule dimers on the formation and disruption of nuclear foci. DM1 patient derived fibroblasts containing 500 CTG repeats (GM03987) were grown to ~80% confluence in a Mat-Tek 96-well glass bottom plate in growth medium. Cells were treated with the compound of interest for 48 h in growth medium followed by FISH as previously described[6] using 1 ng/µL DY547-2'OMe-(CAG)$_6$. Immunostaining of MBNL1 was completed as previously described[7] using the MB1a antibody (diluted 1:4), which was generously supplied by Prof Glenn E. Morris (Wolfson Centre for Inherited Neuromuscular Disease[9]. This was fluorescently labeled using a 1:200 dilution of goat anti-mouse IgG DyLight 488 conjugate. Untreated controls were stained using a 1 µg/µL solution of DAPI in 1×DPBS. Cells were imaged in 1×DPBS using an Olympus FluoView 1000 confocal microscope at 100× magnification.

Evaluation of Translational Defects Using a Luciferase Reporter Assay.

C2Cl2 cell lines expressing 800 or 0 CTG repeats in the 3' UTR of luciferase were grown as monolayers in 96-well plates in growth medium (1×DMEM, 10% FBS, 1× glutagro, (Corning) and 1× antibiotic/antimycotic (Corning))[10]. Once the cells were 70% confluent, the click functionalized dimers were added in 100 µL of growth medium (1000 nM N$_3$-2H-K4NMeS and 1000, 10 and 0.1 nM N$_3$-2H-K4NMeS-Aak). Cells were treated with compound for 48 h and then the cell count was normalized using WST-1 reagent (Roche). Then cells were washed with 1×DPBS and lysed by treating with 50 µL of PPBT lysis buffer at room temperature for 10 minutes. Then 50 µL of luciferase substrate was added and luminescence was measured.

Evaluation of In Vitro Click as Measured by FRET.

In order to determine if the repeating RNA that causes DM1 serves as a template for oligomerization via HDCR, FAM-2H-K4NMeS Aak and $N_3$-2H-K4NMeS Aak were incubated with an RNA containing 12 CUG repeats. $rCUG_{12}$ (80 μM final concentration) was folded in 1× Folding Buffer (20 mM HEPES, pH 7.5, 100 M KCl, and 10 mM NaCl). After cooling to room temperature, FAM-2H-K4NMeS Aak (60 nM final concentration) and $N_3$-2H-K4NMeS Aak (40 nM final concentration) were added and the reaction mixtures were incubated at 37° C. for a total of 48 h. FRET was measured by exciting at 485 nm and measuring emission at 590 nm. Enhancement in FRET was quantified by comparing to controls with FAM-2H-K4NMeS Aak (60 nM final concentration) and $N_3$-2H-K4NMeS Aak (40 nM final concentration) in the absence of RNA. Also FRET was measured using a base-paired control RNA ($r(GC)_{20}$) as a negative control.

DOCUMENTS CITED FOR EXAMPLES SECTION

[1] J. L. Childs-Disney, I. Yildirim, H. Park, J. R. Lohman, L. Guan, T. Tran, P. Sarkar, G. C. Schatz, M. D. Disney, *ACS Chem. Biol.* 2014, 9, 538-550.
[2] J. L. Banks, H. S. Beard, Y. Cao, A. E. Cho, W. Damm, R. Farid, A. K. Felts, T. A. Halgren, D. T. Mainz, J. R. Maple, R. Murphy, D. M. Philipp, M. P. Repasky, L. Y. Zhang, B. J. Berne, R. A. Friesner, E. Gallicchio, R. M. Levy, *J. Comput. Chem.* 2005, 26, 1752-1780.
[3] K. J. Bowers, E. Chow, H. Xu, R. O. Dror, M. P. Eastwood, B. A. Gregersen, J. L. Klepeis, I. Kolossváry, M. A. Moraes, F. D. Sacerdoti, J. K. Salmon, Y. Shan, D. E. Shaw, *Proceedings of the ACM/IEEE Conference on Supercomputing (SC06), Tampa, Fla.* 2006.
[4] T. R. Chan, R. Hilgraf, K. B. Sharpless, V. V. Fokin, *Org. Lett.* 2004, 6, 2853-2855.
[5] C. Fugier, A. F. Klein, C. Hammer, S. Vassilopoulos, Y. Ivarsson, A. Toussaint, V. Tosch, A. Vignaud, A. Ferry, N. Messaddeq, Y. Kokunai, R. Tsuburaya, P. de la Grange, D. Dembele, V. Francois, G. Precigout, C. Boulade-Ladame, M. C. Hummel, A. L. de Munain, N. Sergeant, A. Laquerriere, C. Thibault, F. Deryckere, D. Auboeuf, L. Garcia, P. Zimmermann, B. Udd, B. Schoser, M. P. Takahashi, I. Nishino, G. Bassez, J. Laporte, D. Furling, N. Charlet-Berguerand, *Nat. Med.* 2011, 17, 720-725.
[6] M. B. Warf, M. Nakamori, C. M. Matthys, C. A. Thornton, J. A. Berglund, *Proc. Natl. Acad. Sci. U.S.A* 2009, 106, 18551-18556.
[7] Y. K. Ho, W. T. Xu, H. P. Too, *PLoS ONE* 2013, 8, e72463.
[8] Mankodi, A., Logigian, E., Callahan, L., McClain, C., White, R., Henderson, D., Krym, M., and Thornton, C. A. (2000) Myotonicdystrophy in transgenic mice expressing an expanded CUG repeat. Science 289, 1769-1773.
[9] Holt, I.; Mittal, S.; Furling, D.; Butler-Browne, G. S.; David Brook, J.; Morris, G. E. *Genes to Cells* 2007, 12, 1035.
[10] Childs-Disney, J. L.; Hoskins, J.; Rzuczek, S. G.; Thornton, C. A.; Disney, M. D. *ACS Chemical Biology* 2012.

While the invention has been described and exemplified in sufficient detail for those skilled in this art to make and use it, various alternatives, modifications, and improvements will be apparent to those skilled in the art without departing from the spirit and scope of the claims.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A modulator of the function of a toxic disease-inducing RNA, wherein the disease is myotonic dystrophy type 2 (DM2) or myotonic dystrophy type 1 (DM1), wherein the RNA comprises expanded repeat sequences comprising adjacent internal loops formed by RNA expanded repeat sequences $r(CCUG)^{exp}$ or repeat $r(CUG)^{exp}$, respectively, the modulator comprising an RNA-binding oligomer that is formed in situ within a living cell from a condensation reaction of a cell-permeable RNA expanded repeat sequence binding module, wherein the cell-permeable module comprises both an alkyne and an azide moiety, or from a condensation of a pair of cell-permeable RNA expanded repeat sequence binding modules, wherein a first module comprises an alkyne moiety and a second module comprises an azide moiety, the condensation reaction taking place between the RNA expanded repeat bound modules via an a 1,3 Huisgen dipolar cycloaddition reaction between the alkyne and azide moieties, wherein the cell-permeable module is $N_3$-K-Ak, or is $N_3$-K-AaK, or a pair of cell-permeable modules used together are $N_3$-K and K-Ak.

2. A method of forming the modulator of claim 1 bound to the toxic RNA, comprising exposing the living cell comprising the toxic RNA to a cell-permeable RNA expanded repeat sequence binding module, wherein the cell-permeable module comprises both an alkyne and an azide moiety, or to a pair of cell-permeable RNA expanded repeat sequence binding modules, wherein a first module comprises an alkyne moiety and a second module comprises an azide moiety, wherein the cell-permeable module is $N_3$-K-Ak, or is $N_3$-K-AaK, or a pair of cell-permeable modules used together are $N_3$-K and K-Ak.

3. A method of cleaving a toxic disease-inducing RNA, wherein the RNA comprises expanded repeat sequences, the modulator comprising a modulator of claim 1 further comprising a nucleic acid cleaving moiety.

4. The method of claim 3 wherein the nucleic acid cleaving moiety is a derivative of bleomycin.

5. A method of treatment of myotonic dystrophy type 2 (DM2) in a patient wherein the disease is induced by the presence of a toxic RNA wherein the toxic RNA comprises $r(CCUG)^{exp}$ expanded repeat sequences, or of myotonic dystrophy type 1 (DM1), the toxic RNA comprises or $r(CUG)^{exp}$ expanded repeat sequences, comprising forming within the patient's cells a modulator of claim 1.

6. The method of claim 5, wherein the modulator further comprises a nucleic acid cleaving moiety.

* * * * *